United States Patent
Walker et al.

(10) Patent No.: US 8,629,276 B2
(45) Date of Patent: Jan. 14, 2014

(54) INHIBITORS OF HUMAN IMMUNODEFICIENCY VIRUS REPLICATION

(71) Applicant: Bristol-Myers Squibb Company, Princeton, NJ (US)

(72) Inventors: Michael A. Walker, Durham, CT (US); Margaret E. Sorenson, Meriden, CT (US); B. Narasimhulu Naidu, Durham, CT (US); Kevin Peese, Haddam, CT (US); Barry L. Johnson, Wallingford, CT (US); Manoj Patel, Berlin, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/766,587

(22) Filed: Feb. 13, 2013

(65) Prior Publication Data
US 2013/0210857 A1    Aug. 15, 2013

Related U.S. Application Data

(60) Provisional application No. 61/599,102, filed on Feb. 15, 2012.

(51) Int. Cl.
*A61K 31/44* (2006.01)
*C07D 471/02* (2006.01)

(52) U.S. Cl.
USPC .................................. 546/122; 514/300

(58) Field of Classification Search
None
See application file for complete search history.

(56) References Cited

U.S. PATENT DOCUMENTS

| | | |
|---|---|---|
| 2008/0221159 A1 | 9/2008 | Tsantrizos et al. |
| 2010/0292227 A1 | 11/2010 | Yoakim et al. |
| 2010/0305115 A1 | 12/2010 | Carson et al. |
| 2010/0311735 A1 | 12/2010 | Tsantrizos et al. |
| 2011/0028464 A1 | 2/2011 | Tsantrizos et al. |
| 2011/0118249 A1 | 5/2011 | Tsantrizos et al. |
| 2011/0207626 A1 | 8/2011 | Inazawa et al. |
| 2012/0129840 A1 | 5/2012 | Chalton et al. |
| 2012/0316161 A1 | 12/2012 | Carlens et al. |
| 2013/0203727 A1 | 8/2013 | Babaoglu et al. |
| 2013/0203748 A1 | 8/2013 | Naidu et al. |
| 2013/0210801 A1 | 8/2013 | Babaoglu et al. |

FOREIGN PATENT DOCUMENTS

| WO | WO2012/102985 | 8/2012 |
|---|---|---|
| WO | WO2012/140243 | 10/2012 |

OTHER PUBLICATIONS

U.S. Appl. No. 13/782,198, filed Mar. 1, 2013, Pendri et al.
U.S. Appl. No. 13/782,996, filed Mar. 1, 2013, Zheng et al.

*Primary Examiner* — Janet L Andres
*Assistant Examiner* — Heidi Reese
(74) *Attorney, Agent, or Firm* — James Epperson

(57) ABSTRACT

The disclosure generally relates to compounds of formula I, including compositions and methods for treating human immunodeficiency virus (HIV) infection. The disclosure provides novel inhibitors of HIV, pharmaceutical compositions containing such compounds, and methods for using these compounds in the treatment of HIV infection.

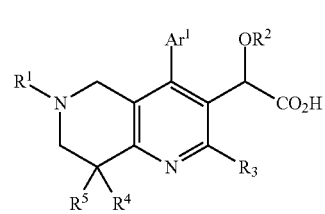

15 Claims, No Drawings

INHIBITORS OF HUMAN IMMUNODEFICIENCY VIRUS REPLICATION

CROSS-REFERENCE TO RELATED APPLICATIONS

This application claims the benefit of U.S. Provisional Application Ser. No. 61/599,102 filed Feb. 15, 2012.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that as many as 33 million people worldwide are infected with the virus (UNAIDS: Report on the Global HIV/AIDS Epidemic, December 1998). In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: however, the effect is only temporary as the virus readily develops resistance to all known agents used as monotherapy. However, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Further, J.; Satten, G. A.; Aschman, D. J.; Holmberg, S. D. N. Engl. J. Med. 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, and WO2009062308.

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

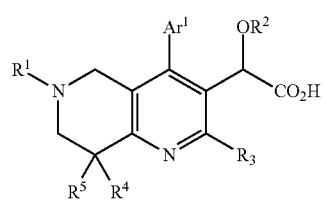

where:
$R^1$ is hydrogen, alkyl, cycloalkyl, haloalkyl, $(Ar^2)$alkyl, $(Ar^2)$cycloalkyl, $Ar^2$, alkylCO, cycloalkylCO, haloalkylCO, $(Ar^2)$alkylCO, $((Ar^2)$cycloalkyl)alkylCO, $(Ar^2)$cycloalkylCO, $Ar^2CO$, $(Ar^2)$alkylCOCO, $Ar^2COCO$, alkylCO$_2$, haloalkylCO$_2$, $(Ar^2)$alkylCO$_2$, $Ar^2CO_2$, alkylCONH, haloalkylCONH, $(Ar^2)$alkylCONH, $Ar^2CONH$, alkylSO$_2$, cycloalkylSO$_2$, haloalkylSO$_2$, and $Ar^2SO_2$;
or $R^1$ is (PhCH$_2$O)PhCH$_2$CO,

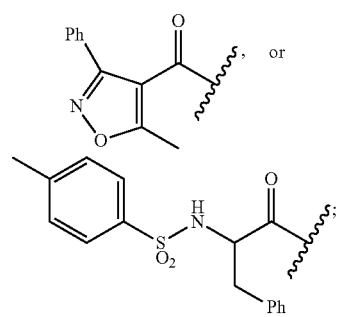

$R^2$ is alkyl or haloalkyl;
$R^3$ is alkyl;
$R^4$ is hydrogen or alkyl;
$R^5$ is hydrogen or alkyl;
$Ar^1$ is phenyl or chromanyl, and is substituted with 0-3 substituents selected from halo, alkyl, haloalkyl, alkoxy, and haloalkoxy; and Ar² is phenyl, biphenyl, or indolyl, and is substituted with 0-3 substituents selected from halo, alkyl, haloalkyl, cycloalkyl, halocycloalkyl, alkoxy, and haloalkoxy;
or a pharmaceutically acceptable salt thereof.

Another aspect of the invention is a compound of formula I where:
R¹ is hydrogen, alkyl, cycloalkyl, haloalkyl, (Ar²)alkyl, (Ar²)cycloalkyl, Ar², alkylCO, cycloalkylCO, haloalkylCO, (Ar²)alkylCO, (Ar²)cycloalkylCO, Ar²CO, (Ar²)alkylCOCO, Ar²COCO, alkylCO₂, haloalkylCO₂, (Ar²)alkylCO₂, Ar²CO₂, alkylCONH, haloalkylCONH, (Ar²)alkylCONH, Ar²CONH, alkylSO₂, cycloalkylSO₂, haloalkylSO₂, and Ar²SO₂;
or R¹ is (PhCH₂O)PhCH₂CO,

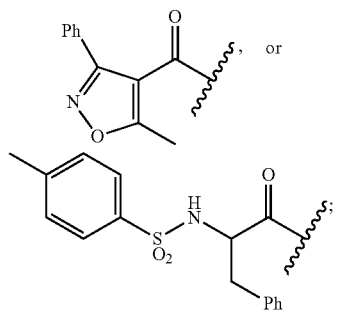

R² is alkyl or haloalkyl;
R³ is alkyl;
R⁴ is hydrogen or alkyl;
R⁵ is hydrogen or alkyl;
Ar¹ is phenyl or chromanyl, and is substituted with 0-3 substituents selected from halo, alkyl, haloalkyl, alkoxy, and haloalkoxy; and
Ar² is phenyl, biphenyl, or indolyl, and is substituted with 0-3 substituents selected from halo, alkyl, haloalkyl, cycloalkyl, and halocycloalkyl;
or a pharmaceutically acceptable salt thereof.

Another aspect of the invention is a compound of formula I where:
R¹ is hydrogen, (Ar²)alkyl, Ar², alkylCO, (Ar²)alkylCO, (Ar²)cycloalkylCO, Ar²CO, Ar²COCO, alkylO₂C, ((Ar²)alkoxyCO, (Ar²)alkylNHCO, and alkylSO₂;
or R¹ is (PhCH₂O)PhCH₂CO,

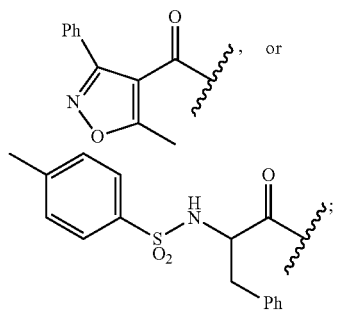

R² is alkyl;
R³ is alkyl;
R⁴ is hydrogen or alkyl;
R⁵ is hydrogen or alkyl;
Ar¹ is phenyl or chromanyl, and is substituted with 0-3 substituents selected from halo, alkyl, haloalkyl, alkoxy, and haloalkoxy; and Ar² is phenyl, biphenyl, or indolyl, and is substituted with 0-3 substituents selected from halo, alkyl, haloalkyl, cycloalkyl, and halocycloalkyl;
or a pharmaceutically acceptable salt thereof.

Another aspect of the invention is a compound of formula I where: R¹ is hydrogen, (Ar²)alkyl, Ar², alkylCO, (Ar²)alkylCO, (Ar²)cycloalkylCO, Ar²CO, Ar²COCO, alkylO₂C, ((Ar²)alkoxyCO, (Ar²)alkylNHCO, and alkylSO₂; R² is alkyl; R³ is alkyl; R⁴ is hydrogen or alkyl; R⁵ is hydrogen or alkyl; Ar¹ is phenyl substituted with 0-3 halo or alkyl substituents; and Ar² is phenyl, biphenyl, or indolyl, and is substituted with 0-3 halo substituents; or a pharmaceutically acceptable salt thereof.

Another aspect of the invention is a compound of formula I where R¹ is hydrogen, (Ar²)alkyl, Ar², alkylCO, (Ar²)alkylCO, (Ar²)cycloalkylCO, Ar²CO, Ar²COCO, alkylO₂C, ((Ar²)alkoxyCO, (Ar²)alkylNHCO, and alkylSO₂.

Another aspect of the invention is a compound of formula I where R² is alkyl.

Another aspect of the invention is a compound of formula I where R³ is alkyl.

Another aspect of the invention is a compound of formula I where R⁴ is hydrogen or alkyl.

Another aspect of the invention is a compound of formula I where R⁵ is hydrogen or alkyl.

Another aspect of the invention is a compound of formula I where Ar¹ is phenyl substituted with 0-3 halo substituents.

Another aspect of the invention is a compound of formula I where Ar² is phenyl, biphenyl, or indolyl, and is substituted with 0-3 halo substituents.

For a compound of Formula I, the scope of any instance of a variable substituent, including R¹, R², R³, R⁴, R⁵, Ar¹, and Ar², can be used independently with the scope of any other instance of a variable substituent. As such, the invention includes combinations of the different aspects.

Unless specified otherwise, these terms have the following meanings. "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. Parenthetic and multiparenthetic terms are intended to clarify bonding relationships to those skilled in the art. For example, a term such as ((R)alkyl) means an alkyl substituent further substituted with the substituent R.

"Chroman" means

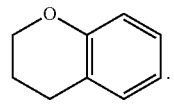

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV Replication.

A recombinant NL-Rluc virus was constructed in which a section of the nef gene from NL4-3 was replaced with the *Renilla* Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv in 293T cells using the LipofectAMINE PLUS kit from Invitrogen (Carlsbad, Calif.) according to the manufacturer, and the pseudotype virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. This provides a simple and easy method for quantitating the extent of virus growth and consequently, the antiviral activity of test compounds. Luciferase was quantitated using the Dual Luciferase kit from Promega (Madison, Wis.).

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)_m]$ (Johnson V A, Byington R T. Infectivity Assay. In *Techniques in HIV Research*. ed. Aldovini A, Walker B D. 71-76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in Table 1.

| Example | $EC_{50}\ \mu M$ |
|---|---|
| Example 2 | 10.020 |
| Example 3 | 6.788 |
| Example 4 | 3.161 |
| Example 5 | 5.134 |
| Example 6 | 0.185 |
| Example 7 | 7.538 |
| Example 8 | 6.717 |
| Example 9 | 6.708 |
| Example 10 | 0.777 |
| Example 11 | 4.122 |
| Example 12 | 7.128 |
| Example 13 | 2.012 |
| Example 14 | 10.190 |
| Example 15 | 2.091 |
| Example 16 | 6.925 |
| Example 17 | 4.604 |
| Example 18 | 2.016 |
| Example 19 | 0.226 |
| Example 20 | 13.460 |
| Example 21 | 0.295 |
| Example 22 | 2.647 |
| Example 23 | 2.083 |
| Example 24 | 0.240 |
| Example 25 | 1.916 |
| Example 26 | 1.643 |
| Example 27 | 0.499 |
| Example 28 | 0.335 |
| Example 29 | 0.010 |
| Examples 30 | 0.323 |
| Example 31 | 0.466 |
| Example 32 | 2.298 |
| Example 33 | 0.017 |
| Example 34 | 0.012 |
| Example 35 | 0.003 |
| Example 36 | 0.052 |
| Example 37 | 0.069 |
| Example 38 | 0.543 |
| Example 39 | 0.137 |
| Example 40 | 0.002 |
| Example 41 | 0.150 |
| Example 42 | 0.007 |
| Example 43 | 0.029 |
| Example 44 | 0.003 |
| Example 45 | 0.004 |
| Example 46 | 0.139 |
| Example 47 | 0.002 |
| Example 48 | 0.002 |
| Example 49 | 0.004 |
| Example 50 | 0.005 |
| Example 51 | 0.001 |
| Example 52 | 0.002 |
| Example 53 | 0.002 |
| Example 54 | 0.002 |
| Example 55 | 0.001 |

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences,* 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC" for t-butoxycarbonate, "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Scheme 1 shows the syntheses of advanced intermediates 1-4, 1-6 and 1-7. The synthesis of intermediate 1-1 has been described previously (US-2007/0249583). This intermediate can be oxidized to the corresponding aldehyde (1-2) using catalytic TPAP (tetrapropylammonium perruthenate) and NMO (N-methylmorpholine-N-oxide). The aldehyde can be treated with TMSCN and ZnI$_2$ to yield cyanohydrin (1-3) which can be further transformed to advanced intermediate 1-4 after hydrolysis of the nitrile to the corresponding methyl ester and removal of the timethylsilylcarbonate group using a methanolic solution of HCl. Reaction of 1-4 with trifluoroacetic anhydride can form the corresponding trifluoro acetyl amide while treatment with tert-butyl acetate and perchloric acid can introduce the tert-butyl ether group of 1-5. Advanced intermediate 1-6 can be synthesized hydrolysis of the trifluoroacetyl amide and methyl ester. Intermediate 1-6 can be derived from selective hydrolysis of the trifluoroacetamide.

Scheme 1
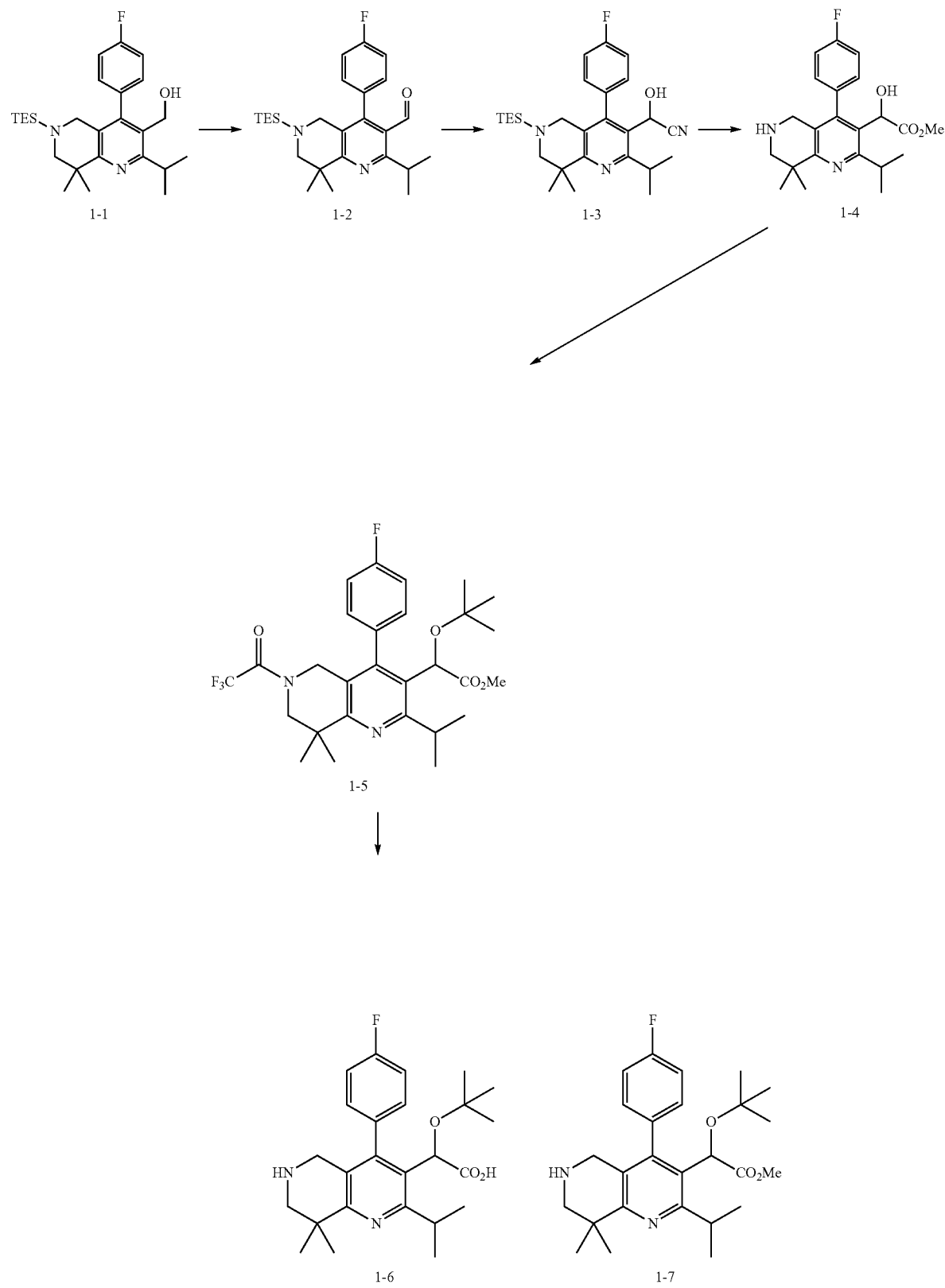

Scheme 2 shows the conversion of intermediate 1-6 compounds of the current invention. Intermediate 1-6 can be directly amidated under standard conditions using carboxylic acid chlorides, carboxylic acid anhydrides and other activated carboxylic acid derivatives (2-1 in Scheme 2).

Scheme 2

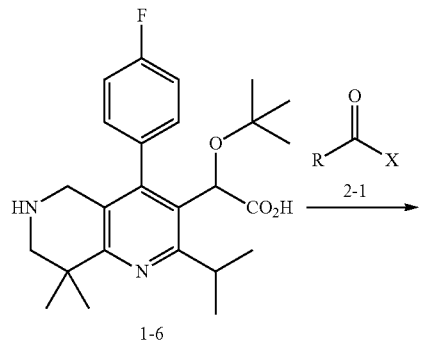

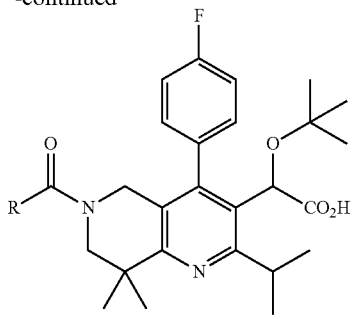

Intermediate 1-7 can be coupled with aryl borinate esters (X=B(OH)$_2$, 3-1 in Scheme 3) to form intermediate 3-2. Those skilled in the art will recognize that the coupling reaction is not limited to arylborinates but could also be applied to other leaving groups. Alternatively, reductive amination can be used to couple aldehyde and ketones (3-3) to 1-7 to afford intermediate 3-4. Intermediates 3-2 and 3-4 afford the corresponding carboxylic acids under ester hydrolysis conditions.

Scheme 3

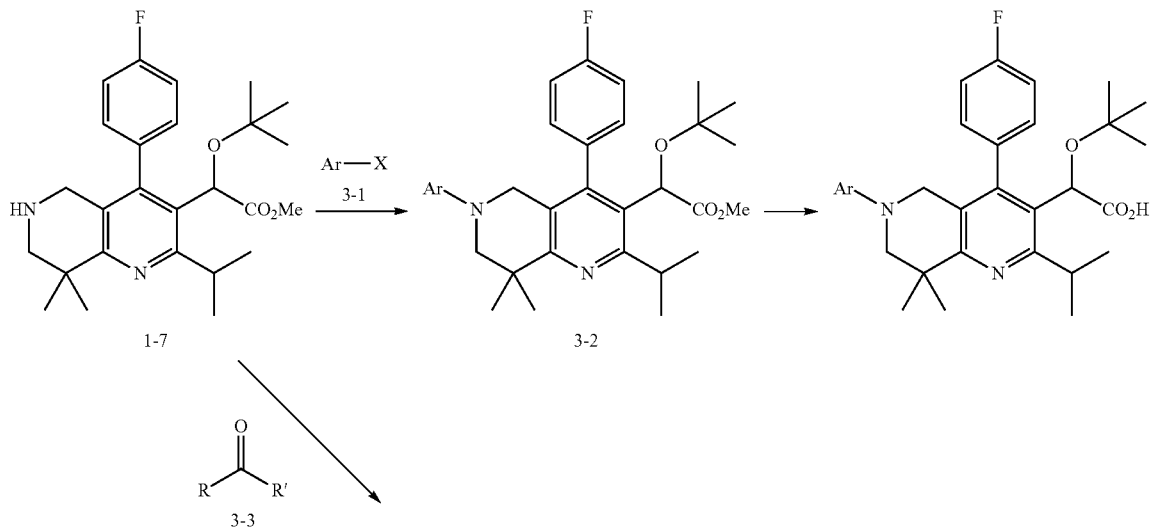

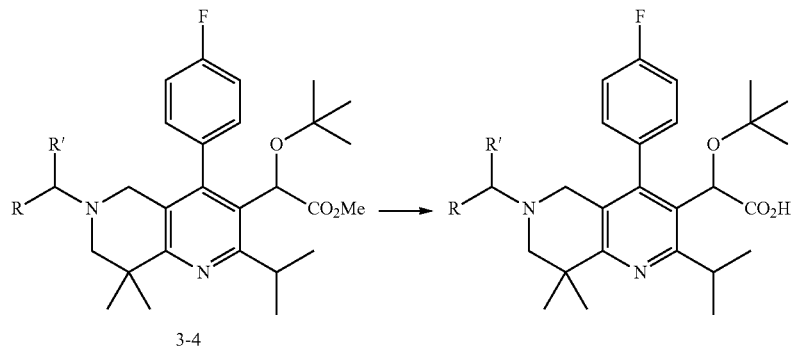

As shown in Scheme 4, intermediate 4-3 can be synthesized using a procedure similar to that described in US2007/0249583. Upon hydrolysis of the ester compound 4-4 can be produced which can be converted to the corresponding alpha-keto carboxylic acid ester 4-5 using a literature procedure (J. Am. Chem. Soc. 2008, 4253). Reduction of the alpha-ketone group of 4-5 to produce alpha-hydroxy acid 4-6 followed formation of the tert-butyl ether can deliver intermediate 4-7. The nitrogen protecting group can be removed under standard conditions to form advanced intermediate 4-8.

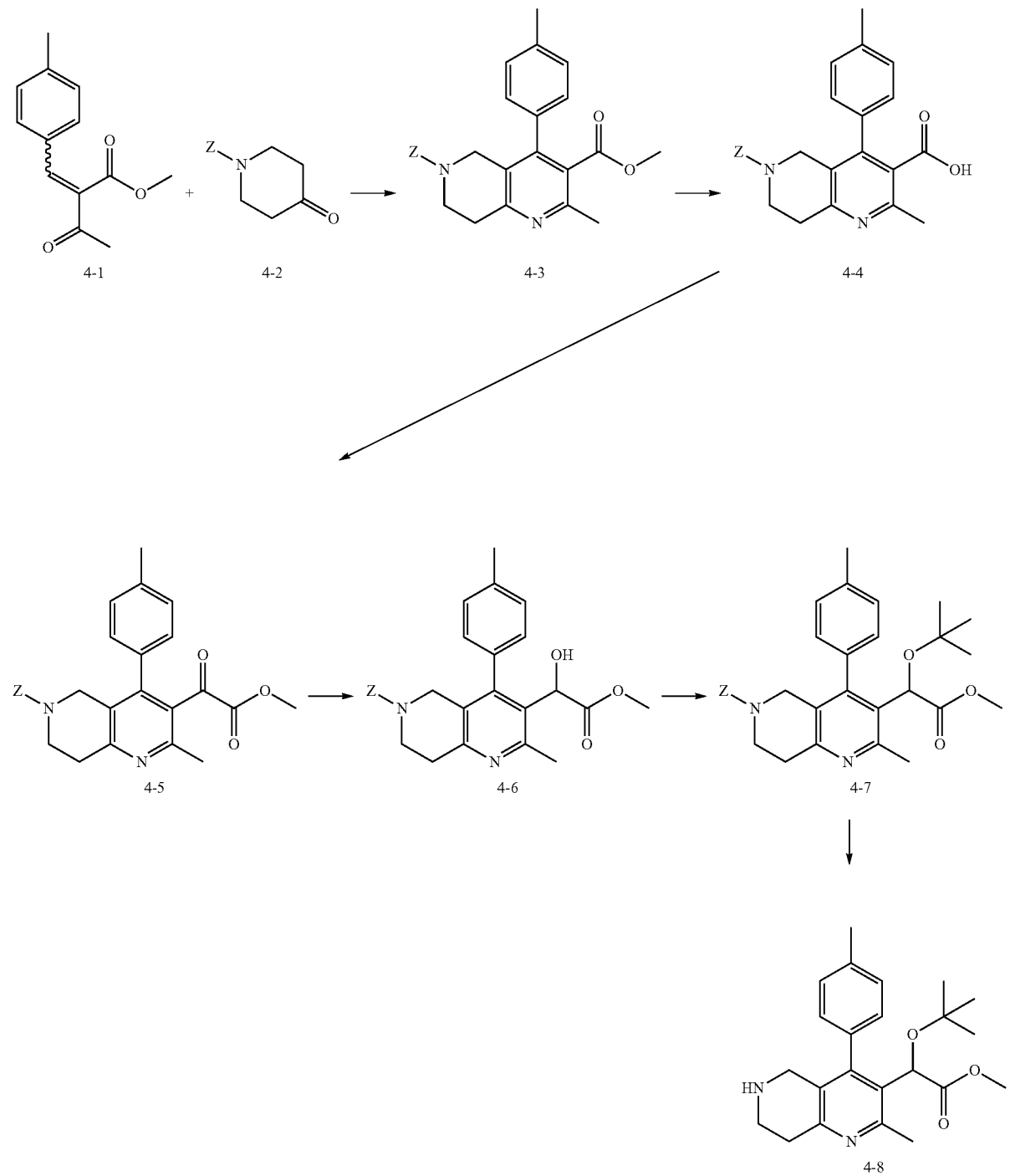

Scheme 4

Scheme 5 shows a conversion of intermediate 4-8 to compounds of this invention using methods similar to those described in Scheme 3.

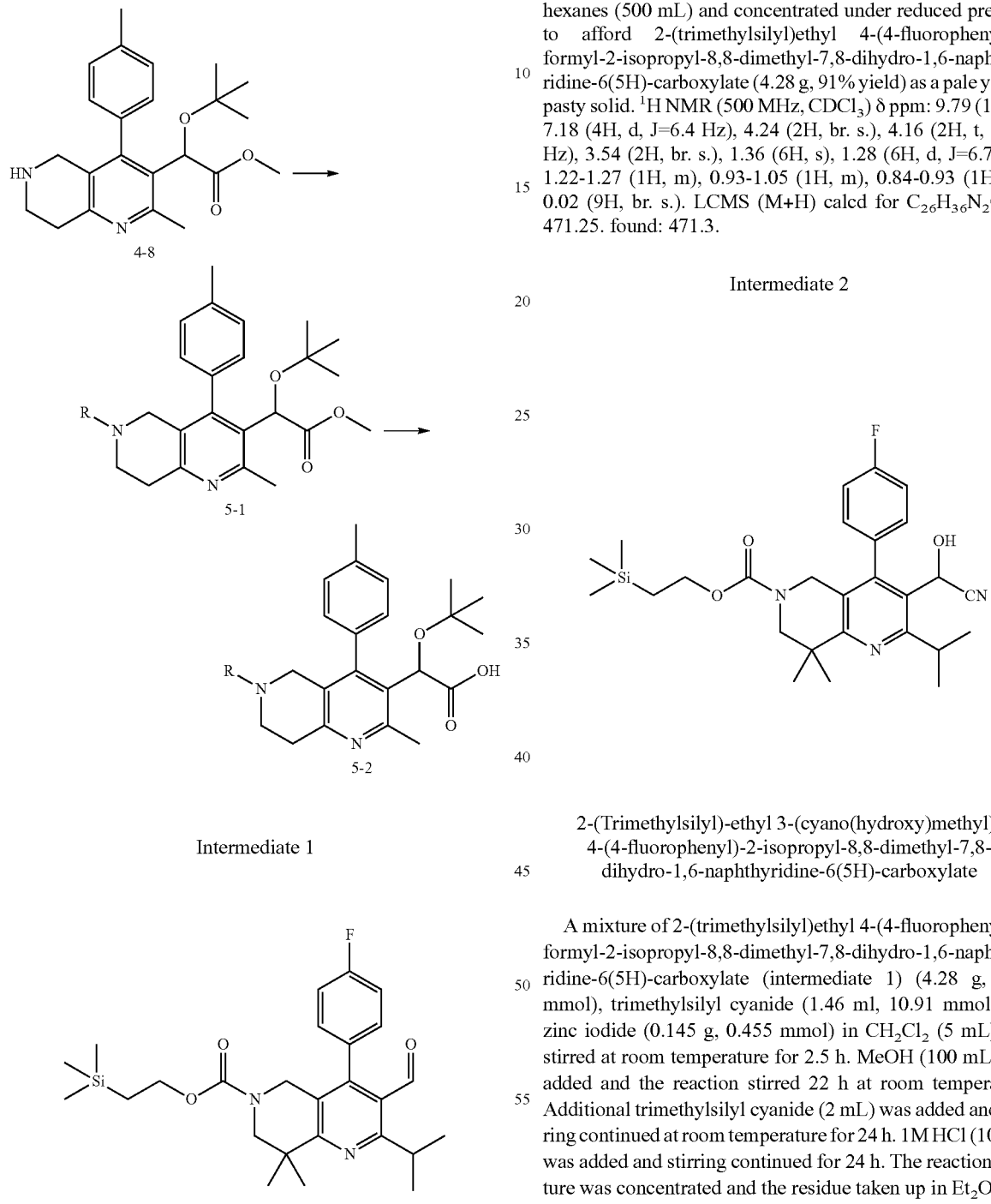

Intermediate 1

2-(Trimethylsilyl)-ethyl 4-(4-fluorophenyl)-3-formyl-2-isopropyl-8,8-dimethyl-7,8-dihydro-1,6-naphthyridine-6(5H)-carboxylate To a stirred mixture of 2-(trimethylsilyl) ethyl 4-(4-fluorophenyl)-3-(hydroxymethyl)-2-isopropyl-8,8-dimethyl-7,8-dihydro-1,6-naphthyridine-6(5H)-carboxylate (4.73 g, 10 mmol), N-methylmorpholine-N-oxide (1.29 g, 11.00 mmol) and 4 Å molecular sieves (2 g) in $CH_2Cl_2$ (100 mL) was added tetrapropylammonium perruthenate (0.09 g, 0.25 mmol) at rt. After 5 h, the reaction mixture was diluted with hexanes (100 mL), filtered through a plug of silica gel using 1:1 $Et_2O$/hexanes (500 mL) and concentrated under reduced pressure to afford 2-(trimethylsilyl)ethyl 4-(4-fluorophenyl)-3-formyl-2-isopropyl-8,8-dimethyl-7,8-dihydro-1,6-naphthyridine-6(5H)-carboxylate (4.28 g, 91% yield) as a pale yellow pasty solid. $^1$H NMR (500 MHz, $CDCl_3$) δ ppm: 9.79 (1H, s), 7.18 (4H, d, J=6.4 Hz), 4.24 (2H, br. s.), 4.16 (2H, t, J=8.1 Hz), 3.54 (2H, br. s.), 1.36 (6H, s), 1.28 (6H, d, J=6.7 Hz), 1.22-1.27 (1H, m), 0.93-1.05 (1H, m), 0.84-0.93 (1H, m), 0.02 (9H, br. s.). LCMS (M+H) calcd for $C_{26}H_{36}N_2O_3Si$: 471.25. found: 471.3.

Intermediate 2

2-(Trimethylsilyl)-ethyl 3-(cyano(hydroxy)methyl)-4-(4-fluorophenyl)-2-isopropyl-8,8-dimethyl-7,8-dihydro-1,6-naphthyridine-6(5H)-carboxylate A mixture of 2-(trimethylsilyl)ethyl 4-(4-fluorophenyl)-3-formyl-2-isopropyl-8,8-dimethyl-7,8-dihydro-1,6-naphthyridine-6(5H)-carboxylate (intermediate 1) (4.28 g, 9.09 mmol), trimethylsilyl cyanide (1.46 ml, 10.91 mmol) and zinc iodide (0.145 g, 0.455 mmol) in $CH_2Cl_2$ (5 mL) was stirred at room temperature for 2.5 h. MeOH (100 mL) was added and the reaction stirred 22 h at room temperature. Additional trimethylsilyl cyanide (2 mL) was added and stirring continued at room temperature for 24 h. 1M HCl (10 mL) was added and stirring continued for 24 h. The reaction mixture was concentrated and the residue taken up in $Et_2O$ (200 mL), washed with satd $NaHCO_3$ (50 mL), water (25 mL), brine (25 mL), dried ($Na_2SO_4$), filtered and solvent removed to give 2-(trimethylsilyl)ethyl 3-(cyano(hydroxy)methyl)-4-(4-fluorophenyl)-2-isopropyl-8,8-dimethyl-7,8-dihydro-1,6-naphthyridine-6(5H)-carboxylate (4.16 g) as a tan powder contaminated with about 20% of starting material. This was used in the next step without further purification.

Intermediate 3

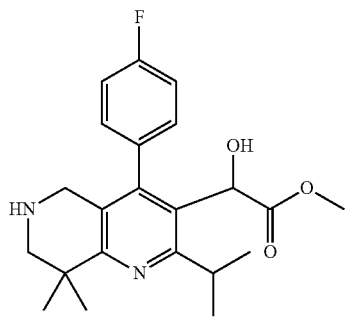 [SMILES: COC(=O)C(O)c1c(C(C)C)nc2c(c1-c1ccc(F)cc1)CNCC2(C)C]

Methyl 2-(4-(4-fluorophenyl)-2-isopropyl-8,8-dimethyl-5,6,7,8-tetrahydro-1,6-naphthyridin-3-yl)-2-hydroxyacetate A solution of 2-(trimethylsilyl)ethyl 3-(cyano(hydroxy)methyl)-4-(4-fluorophenyl)-2-isopropyl-8,8-dimethyl-7,8-dihydro-1,6-naphthyridine-6(5H)-carboxylate (intermediate 2) (2.05 g, 3.30 mmol) in anhydrous MeOH (30 mL) was saturated with HCl gas by bubbling it through the reaction mixture at 0° C. The mixture was slowly warmed to room temperature over 4 h and let stand for 68 h in a sealed (rubber septum) flask. Concentrated HCl (1 mL) was added to the mixture which was then stirred at reflux for 24 h. The reaction was cooled and the solvent removed to provide a yellow residue which was purified by reverse phase medium pressure liquid chromatography, eluting with 30-60% MeOH/H$_2$O to provide methyl 2-(4-(4-fluorophenyl)-2-isopropyl-8,8-dimethyl-5,6,7,8-tetrahydro-1,6-naphthyridin-3-yl)-2-hydroxyacetate 2 HCl (1.14 g, 76% yield). $^1$H NMR (500 MHz, DMSO-d$_6$) δ ppm 9.34 (1H, br. s.), 9.20 (1H, br. s.), 7.37-7.45 (2H, m), 7.24-7.34 (2H, m), 6.10 (1H, br. s.), 4.87 (1H, s), 3.65-3.80 (2H, m), 3.58 (3H, s), 3.26-3.36 (3H, m), 1.43 (3H, s), 1.40 (3H, s), 1.23 (3H, d, J=6.4 Hz), 1.07 (3H, d, J=6.7 Hz). LCMS (M+H) calcd for C$_{22}$H$_{28}$FN$_2$O$_3$: 387.21. found: 387.3. Contaminated with about 10% of 2-(4-(4-fluorophenyl)-2-isopropyl-8,8-dimethyl-5,6,7,8-tetrahydro-1,6-naphthyridin-3-yl)-2-hydroxyacetamide.

Intermediate 4

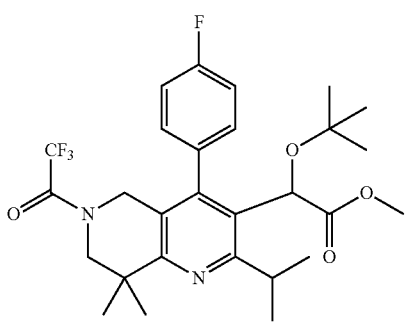 [SMILES: COC(=O)C(OC(C)(C)C)c1c(C(C)C)nc2c(c1-c1ccc(F)cc1)CN(C(=O)C(F)(F)F)CC2(C)C]

Methyl 2-tert-butoxy-2-(4-(4-fluorophenyl)-2-isopropyl-8,8-dimethyl-6-(2,2,2-trifluoroacetyl)-5,6,7,8-tetrahydro-1,6-naphthyridin-3-yl)acetate To a stirred solution of methyl 2-(4-(4-fluorophenyl)-2-isopropyl-8,8-dimethyl-5,6,7,8-tetrahydro-1,6-naphthyridin-3-yl)-2-hydroxyacetate 2 HCl, (intermediate 3) (0.230 g, 0.50 mmol) and Et$_3$N (0.139 ml, 1.0 mmol) in CH$_2$Cl$_2$ (5 mL) was added trifluoroacetic anhydride (0.078 ml, 0.55 mmol) at room temperature. After 2 h, the reaction mixture was diluted with Et$_2$O (50 mL), washed with satd NaHCO$_3$ (25 mL), brine (25 mL), dried (Na$_2$SO$_4$), filtered and concentrated to afford a white solid. To a solution of the solid in CH$_2$Cl$_2$ (10 mL) and tert-butyl acetate (2.03 ml, 15.0 mmol) was added 70% perchloric acid (0.13 ml, 1.5 mmol) at room temperature and the solution stirred for 2 h. The reaction mixture was diluted with Et$_2$O (50 mL), washed with satd NaHCO$_3$ (2×25 mL), brine (25 mL), dried (Na$_2$SO$_4$), filtered and concentrated to afford a yellow residue which was purified by flash column chromatography on silica gel column using 5-35% EtOAc/Hexanes as eluent to afford methyl 2-tert-butoxy-2-(4-(4-fluorophenyl)-2-isopropyl-8,8-dimethyl-6-(2,2,2-trifluoroacetyl)-5,6,7,8-tetrahydro-1,6-naphthyridin-3-yl)acetate (0.15 g, 55% yield). $^1$H NMR (500 MHz, CDCl$_3$) δ ppm 7.10-7.23 (4H, m), 4.80 (1H, s), 4.33-4.03 (2H, m), 3.69 (3H, s), 3.48-3.65 (3H, m), 1.34-1.41 (6H, m), 1.30 (3H, d, J=6.7 Hz), 1.26 (3H, d, J=6.4 Hz), 0.95-0.99 (9H, m). LCMS (M+H) calcd for C$_{28}$H$_{35}$FN$_2$O$_4$: 539.25. found: 539.3.

Intermediate 5

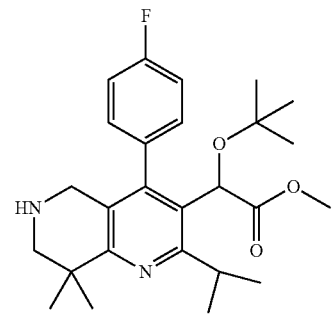 [SMILES: COC(=O)C(OC(C)(C)C)c1c(C(C)C)nc2c(c1-c1ccc(F)cc1)CNCC2(C)C]

Methyl 2-tert-butoxy-2-(4-(4-fluorophenyl)-2-isopropyl-8,8-dimethyl-5,6,7,8-tetrahydro-1,6-naphthyridin-3-yl)acetate A mixture of methyl 2-tert-butoxy-2-(4-(4-fluorophenyl)-2-isopropyl-8,8-dimethyl-6-(2,2,2-trifluoroacetyl)-5,6,7,8-tetrahydro-1,6-naphthyridin-3-yl)acetate (intermediate 4) (0.250 g, 0.464 mmol) and K$_2$CO$_3$ (0.064 g, 0.464 mmol) in MeOH was stirred at room temperature for 24 h. The reaction was diluted with Et$_2$O (50 mL), washed with water (10 mL), brine (10 mL), dried (Na$_2$SO$_4$), filtered and concentrated to give a pale yellow residue which was purified by reverse phase preparative-HPLC, eluting with MeCN/H$_2$O, to afford methyl 2-tert-butoxy-2-(4-(4-fluorophenyl)-2-isopropyl-8,8-dimethyl-5,6,7,8-tetrahydro-1,6-naphthyridin-3-yl)acetate (0.117 g, 57% yield) as a white solid. $^1$H NMR (500 MHz, CDCl$_3$) δ ppm 7.28-7.32 (1H, m), 7.15-7.20 (1H, m), 7.13 (2H, d, J=6.7 Hz), 4.79 (1H, s), 3.75 (1H, d, J=16.2 Hz), 3.69 (3H, s), 3.48 (1H, quin, J=6.6 Hz), 3.42 (1H, d, J=16.5Hz), 2.94-3.05 (2H, m), 2.17 (1H, br. s.), 1.39 (6H, s), 1.26 (3H, d, J=6.4 Hz), 1.09 (3H, d, J=6.7 Hz), 0.95 (9H, s). LCMS (M+H) calcd for C$_{26}$H$_{36}$FN$_2$O$_3$: 443.2. found: 433.3.

Intermediate 6

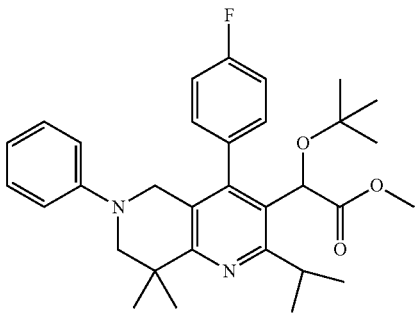 [SMILES: COC(=O)C(OC(C)(C)C)c1c(C(C)C)nc2c(c1-c1ccc(F)cc1)CN(c1ccccc1)CC2(C)C]

Methyl 2-tert-butoxy-2-(4-(4-fluorophenyl)-2-isopropyl-8,8-dimethyl-6-phenyl-5,6,7,8-tetrahydro-1,6-naphthyridin-3-yl)acetate A mixture of Cu(OAc)$_2$ (8.21 mg, 0.045 mmol) and pyridine (3.66 µl, 0.045 mmol) in CH$_2$Cl$_2$ (0.5 mL) was stirred for 5 min. Added to this were methyl 2-tert-butoxy-2-(4-(4-fluorophenyl)-2-isopropyl-8,8-dimethyl-5,6,7,8-tetrahydro-1,6-naphthyridin-3-yl)acetate (intermediate 5) (10 mg, 0.023 mmol), phenylboronic acid (5.51 mg, 0.045 mmol) and 17 mg molecular sieves. The resulting mixture was stirred at room temperature open to air for 17 h. The mixture was adsorbed directly onto silica gel and purified by flash chromatography (Biotage; 0%-50% EtOAc/hexane). $^1$H NMR (500 MHz, CDCl$_3$) δ ppm 7.38 (ddd, J=8.4, 5.8, 2.3 Hz, 1H), 7.27-7.16 (m, 5H), 6.87-6.73 (m, 3H), 4.86 (s, 1H), 3.94 (d, J=15.6 Hz, 1H), 3.73 (s, 3H), 3.69 (d, J=15.6 Hz, 1H), 3.55 (dt, J=13.0, 6.4 Hz, 1H), 3.44-3.34 (m, 1H), 3.28 (d, J=12.5Hz, 1H), 1.49 (d, J=3.7 Hz, 6H), 1.33 (d, J=6.1 Hz, 3H), 1.17 (d, J=6.7 Hz, 3H), 1.01 (s, 9H). $^{19}$F NMR (500 MHz, CDCl$_3$) δ ppm −113.64. LCMS (M+H) calcd for C$_{32}$H$_{40}$FN$_2$O$_3$: 519.30. found: 519.45.

Intermediate 7

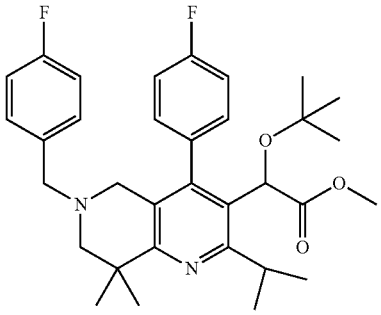 [SMILES: COC(=O)C(OC(C)(C)C)c1c(C(C)C)nc2c(c1-c1ccc(F)cc1)CN(Cc1ccc(F)cc1)CC2(C)C]

Methyl 2-tert-butoxy-2-(6-(4-fluorobenzyl)-4-(4-fluorophenyl)-2-isopropyl-8,8-dimethyl-5,6,7,8-tetrahydro-1,6-naphthyridin-3-yl)acetate A mixture of methyl 2-tert-butoxy-2-(4-(4-fluorophenyl)-2-isopropyl-8,8-dimethyl-5,6,7,8-tetrahydro-1,6-naphthyridin-3-yl)acetate (intermediate 5) (20 mg, 0.045 mmol) and 4-fluorobenzaldehyde (0.048 mL, 0.452 mmol) was stirred in CH$_2$Cl$_2$ (1 mL) at 0° C. for 45 min. AcOH (2.59 µl, 0.045 mmol) was added followed by NaBH(OAc)$_3$ (9.58 mg, 0.045 mmol). After stirring at 0° C. for an additional 5 min, the reaction mixture was stirred at room temperature for 22 h. Additional NaBH(OAc)$_3$ (9.58 mg, 0.045 mmol) and AcOH (2.59 µl, 0.045 mmol) were added and the mixture was stirred for an additional 1 h. The mixture was quenched with satd NaHCO$_3$ and the product was extracted with CH$_2$Cl$_2$, dried (Na$_2$SO$_4$), filtered and adsorbed onto silica gel. The product was purified by flash chromatography (Biotage; 0%-50% EtOAc/hexane) to give methyl 2-tert-butoxy-2-(6-(4-fluorobenzyl)-4-(4-fluorophenyl)-2-isopropyl-8,8-dimethyl-5,6,7,8-tetrahydro-1,6-naphthyridin-3-yl)acetate (14.7 mg, 47% yield) as a colorless oil. $^1$H NMR (500 MHz, CDCl$_3$) δ ppm 7.34 (ddd, J=2.14, 5.72, 8.32 Hz, 1H), 7.24-7.28 (m, 2H), 7.14-7.20 (m, 2H), 7.06-7.14 (m, 1H), 6.99 (t, J=8.70 Hz, 2H), 4.83 (s, 1H), 3.71 (s, 3H), 3.45-3.60 (m, 2H), 3.40 (d, J=13.43 Hz, 1H), 3.23 (d, J=15.26 Hz, 1H), 3.06 (d, J=15.26 Hz, 1H), 2.50 (d, J=10.99 Hz, 1H), 2.34 (d, J=11.29 Hz, 1H), 1.33 (d, J=2.44 Hz, 6H), 1.28 (s, 3H), 1.11 (d, J=6.71 Hz, 3H), 0.98 (s, 9H). $^{19}$F NMR (500 MHz, CDCl$_3$) δ ppm −114.17, −116.52. LCMS (M+H) calcd for C$_{33}$H$_{41}$F$_2$N$_2$O$_3$: 551.30. found: 551.4. By NMR.

Intermediate 8

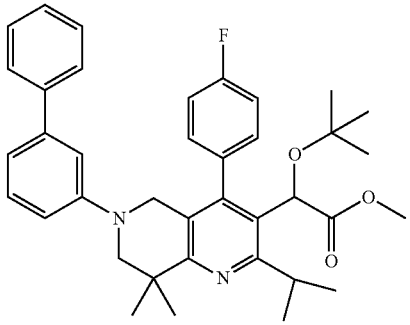 [SMILES: COC(=O)C(OC(C)(C)C)c1c(C(C)C)nc2c(c1-c1ccc(F)cc1)CN(c1cccc(-c3ccccc3)c1)CC2(C)C]

Methyl 2-(6-([1,1'-biphenyl]-3-yl)-4-(4-fluorophenyl)-2-isopropyl-8,8-dimethyl-5,6,7,8-tetrahydro-1,6-naphthyridin-3-yl)-2-(tert-butoxy)acetate A mixture of Cu(OAc)$_2$ (16 mg, 0.09 mmol) and pyridine (7 µl, 0.09 mmol) in CH$_2$Cl$_2$ (1 mL) was stirred for 5 min. Added to this were methyl 2-(tert-butoxy)-2-(4-(4-fluorophenyl)-2-isopropyl-8,8-dimethyl-5,6,7,8-tetrahydro-1,6-naphthyridin-3-yl)acetate (intermediate 5) (20 mg, 0.045 mmol), [1,1'-biphenyl]-3-ylboronic acid (17.9 mg, 0.09 mmol) and 34 mg molecular sieves. The resulting mixture was stirred, uncovered, at room temperature for 21 h. The mixture was adsorbed directly onto silica gel and purified by flash column chromatography (Biotage; 0%-50% EtOAc/hexane) to give methyl 2-(6-([1,1'-biphenyl]-3-yl)-4-(4-fluorophenyl)-2-isopropyl-8,8-dimethyl-5,6,7,8-tetrahydro-1,6-naphthyridin-3-yl)-2-(tert-butoxy)acetate (10 mg, 37% yield) as a white solid. $^1$H NMR (500 MHz, CDCl$_3$) δ ppm 7.58-7.52 (m, 2H), 7.41-7.35 (m, 2H), 7.35-7.30 (m, 1H), 7.27-7.16 (m, 3H), 7.08-7.00 (m, 2H), 6.79-6.70 (m, 1H), 4.88 (s, 1H), 4.01 (d, J=15.6 Hz, 1H), 3.75 (d, J=15.9 Hz, 1H), 3.73 (s, 3H), 3.56 (dt, J=13.1, 6.6 Hz, 1H), 3.49-3.41 (m, 1H), 3.38-3.30 (m, 1H), 1.59 (s, 1H), 1.51 (d, J=4.0 Hz, 6H), 1.35 (s, 3H), 1.17 (d, J=6.7 Hz, 3H), 1.02 (s, 9H). $^{19}$F NMR (500 MHz, CDCl$_3$) δ ppm −113.64. LCMS (M+H) calcd for C$_{38}$H$_{44}$FN$_2$O$_3$: 595.33. found: 595.4.

Intermediate 9

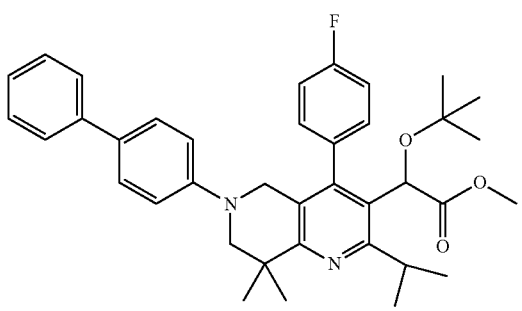 [SMILES: COC(=O)C(OC(C)(C)C)c1c(C(C)C)nc2c(c1-c1ccc(F)cc1)CN(c1ccc(-c3ccccc3)cc1)CC2(C)C]

Methyl 2-(6-([1,1'-biphenyl]-4-yl)-4-(4-fluorophenyl)-2-isopropyl-8,8-dimethyl-5,6,7,8-tetrahydro-1,6-naphthyridin-3-yl)-2-(tert-butoxy)acetate A mixture of Cu(OAc)$_2$ (16.42 mg, 0.090 mmol) and pyridine (7 μl, 0.09 mmol) in CH$_2$Cl$_2$ (1 mL) was stirred for 5 min. Added to this were methyl 2-(tert-butoxy)-2-(4-(4-fluorophenyl)-2-isopropyl-8,8-dimethyl-5,6,7,8-tetrahydro-1,6-naphthyridin-3-yl)acetate (intermediate 5) (20 mg, 0.045 mmol), 4-biphenylboronic acid (17.90 mg, 0.09 mmol) and 34 mg molecular sieves. After stirring uncovered for 18 h, the mixture was adsorbed directly onto silica gel and was purified by flash column chromatography (Biotage; 0%-50% EtOAc/hexane) to give methyl 2-(6-([1,1'-biphenyl]-4-yl)-4-(4-fluorophenyl)-2-isopropyl-8,8-dimethyl-5,6,7,8-tetrahydro-1,6-naphthyridin-3-yl)-2-(tert-butoxy)acetate (22.7 mg, 84% yield) as a colorless oil. LCMS (M+H) calcd for C$_{38}$H$_{44}$FN$_2$O$_3$: 595.33. found: 595.4. $^{19}$F NMR (500 MHz, Methanol d$_4$) δ ppm: −113.055.

Intermediate 10

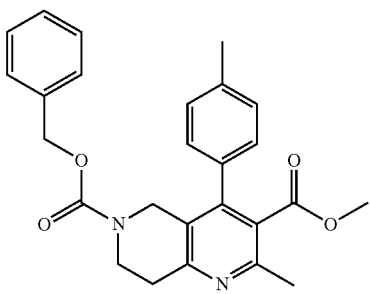 [SMILES: COC(=O)c1c(C)nc2c(c1-c1ccc(C)cc1)CN(C(=O)OCc1ccccc1)CC2]

6-Benzyl 3-methyl 2-methyl-4-(p-tolyl)-7,8-dihydro-1,6-naphthyridine-3,6(5H)-dicarboxylate A solution of 1N (THF) LiHMDS (4.72 mL, 4.72 mmol) in THF (3 mL) was cooled to −78° C. A solution of benzyl 4-oxopiperidine-1-carboxylate (1.0 g, 4.29 mmol) in THF (3.00 mL) was added dropwise over several minutes, while maintaining the internal temperature under −55° C. was. After stirring for 10 min at −78° C., the solution was allowed to warm to −20° C. and stirred for 15 min before cooling to −78° C. again. A cold (−78° C.) solution of methyl 2-(4-methylbenzylidene)-3-oxobutanoate (0.936 g, 4.29 mmol) in THF (1.5 mL) was added via cannula and the resulting yellow solution was stirred at −40° C. for 3 h. The reaction was quenched with AcOH (1.227 mL, 21.44 mmol) and warmed to room temperature. water was added and the aqueous phase was extracted 3 times with EtOAc. The organic phases were combined and washed with brine, dried (Na$_2$SO$_4$), filtered and concentrated to give the Michael addition product as a brown oil (LCMS [M+1]=452.4). The oil was taken up in EtOH (12 mL) and stirred with NH$_4$OAc (2.64 g, 34.3 mmol) and p-toluenesulfonic acid monohydrate (0.041 g, 0.214 mmol) at 80° C. After 70 h, the mixture was cooled to room temperature and concentrated to provide the dihydropyridine intermediate as a thick amber oil. To the residue dissolved in CH$_2$Cl$_2$ (20 mL) was added Cerium(IV) diammonium nitrate (4.70 g, 8.57 mmol) and CF$_3$CO$_2$H (0.330 mL, 4.29 mmol) and the resulting mixture stirred at room temperature for 1.5 h. The mixture was washed with water and the aqueous phase was extracted with CH$_2$Cl$_2$ (2×'s). The organic fractions were combined and dried (Na$_2$SO$_4$), filtered and concentrated. The brown oil was purified by flash column chromatography (Biotage; 0%-100% EtOAc/hexane) to give 6-benzyl 3-methyl 2-methyl-4-(p-tolyl)-7,8-dihydro-1,6-naphthyridine-3,6 (5H)-dicarboxylate (1.2536 g, 67% yield) as an amber oil. $^1$H NMR (400 MHz, CDCl$_3$) δ ppm 7.34 (d, J=4.40 Hz, 5H), 7.22 (d, J=7.82 Hz, 2H), 7.07 (d, J=7.83 Hz, 2H), 5.13 (s, 2H), 4.36 (s, 2H), 3.82 (t, J=5.99 Hz, 2H), 3.54 (s, 3H), 3.07 (br. s., 2H), 2.57 (s, 3H), 2.41 (s, 3H). LCMS (M+H) calcd for C$_{26}$H$_{27}$N$_2$O$_4$: 431.19. found: 431.4.

Intermediate 11

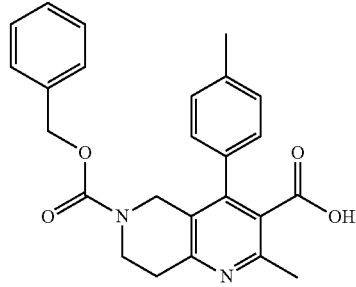 [SMILES: Cc1ccc(-c2c3c(nc(C)c2C(=O)O)CCN(C(=O)OCc2ccccc2)C3)cc1]

6-((Benzyloxy)carbonyl)-2-methyl-4-(p-tolyl)-5,6,7,8-tetrahydro-1,6-naphthyridine-3-carboxylic acid A mixture of 6-benzyl 3-methyl 2-methyl-4-(p-tolyl)-7,8-dihydro-1,6-naphthyridine-3,6(5H)-dicarboxylate (intermediate 10) (0.482 g, 1.12 mmol) and lithium chloride (0.475 g, 11.19 mmol) in 2,6-lutadine (10 mL) and DMSO (10.00 mL) was stirred at 130° C. for 2 h. The mixture was cooled to room temperature, diluted with water and extracted with EtOAc to remove unreacted starting material and impurities. The aqueous phase was made acidic with 1N HCl and extracted with EtOAc (2×'s) then CH$_2$Cl$_2$. The organic extracts were combined, dried (Na$_2$SO$_4$), filtered and concentrated to provide 6-((benzyloxy)carbonyl)-2-methyl-4-(p-tolyl)-5,6,7,8-tetrahydro-1,6-naphthyridine-3-carboxylic acid (74.2 mg, 15% yield) as an amber oil. $^1$H NMR (400 MHz, CDCl$_3$) δ ppm 7.33 (br. s., 4H), 7.24 (d, J=7.83 Hz, 3H), 7.13 (d, J=7.58 Hz, 2H), 5.11 (s, 2H), 4.36 (s, 2H), 3.78 (t, J=5.62 Hz, 2H), 3.30 (br. s., 2H), 2.80 (br. s., 3H), 2.38 (s, 3H). LCMS (M+H) calcd for C$_{25}$H$_{25}$N$_2$O$_4$: 417.18. found: 417.4.

Intermediate 12

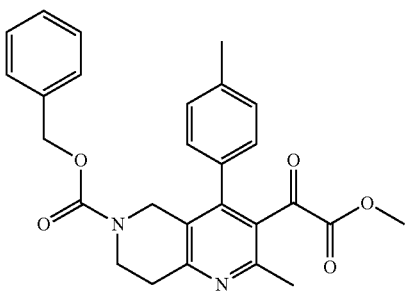 [SMILES: COC(=O)C(=O)c1c(C)nc2c(c1-c1ccc(C)cc1)CN(C(=O)OCc1ccccc1)CC2]

Benzyl 3-(2-methoxy-2-oxoacetyl)-2-methyl-4-(p-tolyl)-7,8-dihydro-1,6-naphthyridine-6(5H)-carboxylate To a suspension of 6-((benzyloxy)carbonyl)-2-methyl-4-(p-tolyl)-5,6,7,8-tetrahydro-1,6-naphthyridine-3-carboxylic acid (intermediate 9) (0.1240 g, 0.298 mmol) in $CH_2Cl_2$ with of DMF (2 mL) was added 2M ($CH_2Cl_2$) oxalyl chloride (0.298 mL, 0.595 mmol) and the solution stirred at room temperature. After 1 h, the mixture was concentrated and azeotroped with toluene 3 times to remove unreacted oxalyl chloride. The residue was taken up in $CH_2Cl_2$ (2.0 mL). $iPr_2NEt$ (0.156 mL, 0.893 mmol) and 1-(cyanomethyl)tetrahydro-1H-thiophen-1-ium, bromide salt (0.081 g, 0.387 mmol) were added and the solution stirred at room temperature for 20 h. The mixture was washed with water, then dried ($Na_2SO_4$), filtered and concentrated to give an amber oil. The oil was dissolved in MeOH (4 mL). a solution of oxone (0.366 g, 0.595 mmol) dissolved in water (1.5 mL) was added. The resulting suspension was stirred at room temperature for 2 h. Methanol was concentrated was removed under vacuum and the remaining solution extracted with EtOAc (3×'s). The organic layers were combined and washed with brine, dried ($Na_2SO_4$), filtered and concentrated. The resulting brown residue was purified by flash chromatography (Biotage; 0%-100% EtOAc/hexane) to provide benzyl 3-(2-methoxy-2-oxoacetyl)-2-methyl-4-(p-tolyl)-7,8-dihydro-1,6-naphthyridine-6(5H)-carboxylate (0.063 g, 32% yield) as a colorless oil. $^1$H NMR (400 MHz, $CDCl_3$) δ ppm 7.14-7.51 (m, 7H), 6.92-7.11 (m, 2H), 5.13 (br. s., 2H), 4.28-4.52 (m, 2H), 3.44 (s, 3H), 3.25-3.38 (m, 2H), 3.11 (br. s., 2H), 2.50-2.63 (m, 3H), 2.41 (s, 3H). LCMS (M+H) calcd for $C_{27}H_{27}N_2O_5$: 459.19. found: 459.3.

Intermediate 13

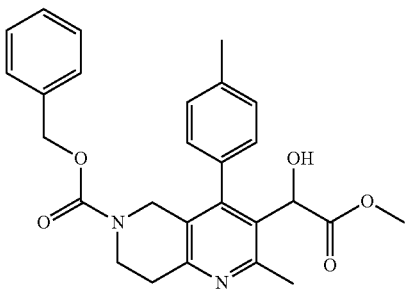 [SMILES: COC(=O)C(O)c1c(C)nc2c(c1-c1ccc(C)cc1)CN(C(=O)OCc1ccccc1)CC2]

Benzyl 3-(1-hydroxy-2-methoxy-2-oxoethyl)-2-methyl-4-(p-tolyl)-7,8-dihydro-1,6-naphthyridine-6(5H)-carboxylate A solution of benzyl 3-(2-methoxy-2-oxoacetyl)-2-methyl-4-(p-tolyl)-7,8-dihydro-1,6-naphthyridine-6(5H)-carboxylate (2.53 g, 5.52 mmol) (intermediate 10) and 1M (toluene) R-5,5-diphenyl-2-methyl-3,4-propano-1,3,2-oxazaborlidine (2.21 ml, 2.21 mmol) in toluene (100 ml) was cooled to −35° C. Catecholborane (50 wt % in toluene) (1.65 ml, 7.73 mmol) was added dropwise and the solution stirred at −35° C. for 30 min then at −15° C. for 2 h. The reaction was diluted with EtOAc and stirred vigorously with sat'd $Na_2CO_3$ for 1 h. The organic phase was washed with twice with satd $Na_2CO_3$, dried ($Na_2SO_4$), filtered and concentrated. The resulting oil was purified by flash column chromatography (Biotage; 0%-100% EtOAc/hexane) to provide benzyl 3-(1-hydroxy-2-methoxy-2-oxoethyl)-2-methyl-4-(p-tolyl)-7,8-dihydro-1,6-naphthyridine-6(5H)-carboxylate (1.29 g, 50% yield) as a white foam. $^1$H NMR (400 MHz, $CDCl_3$) δ ppm 7.20-7.49 (m, 7H), 7.08 (t, J=8.68 Hz, 2H), 5.11 (d, J=15.65 Hz, 3H), 4.22 (br. s., 2H), 3.67-3.89 (m, 5H), 3.14 (d, J=2.45 Hz, 1H), 2.99-3.11 (m, 2H), 2.55 (s, 3H), 2.43 (s, 3H). LCMS (M+H) calcd for $C_{27}H_{29}N_2O_5$: 461.20. found: 461.0.

Intermediate 14

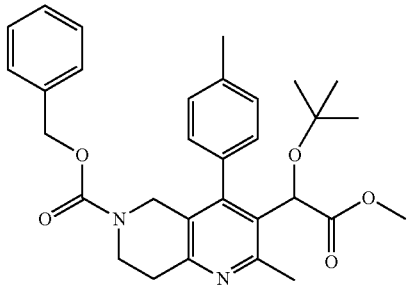 [SMILES: COC(=O)C(OC(C)(C)C)c1c(C)nc2c(c1-c1ccc(C)cc1)CN(C(=O)OCc1ccccc1)CC2]

Benzyl 3-(1-(tert-butoxy)-2-methoxy-2-oxoethyl)-2-methyl-4-(p-tolyl)-7,8-dihydro-1,6-naphthyridine-6(5H)-carboxylate To a solution of benzyl 3-(1-hydroxy-2-methoxy-2-oxoethyl)-2-methyl-4-(p-tolyl)-7,8-dihydro-1,6-naphthyridine-6(5H)-carboxylate (intermediate 11) (0.10 g, 0.217 mmol) in $CH_2Cl_2$ (3 ml) was added tert-butyl acetate (2.05 ml, 15.2 mmol) followed by $HClO_4$ (0.056 ml, 0.651 mmol). The flask was sealed and stirred at room temperature for 2.5 h. The reaction was quenched with sat'd aq $NaHCO_3$ (gas evolution). The organic phase was dried ($Na_2SO_4$), filtered and concentrated. The residue was purified by flash column chromatography (Biotage; 0%-30% EtOAc/hexanes). The product-containing fractions were combined and concentrated to give benzyl 3-(1-(tert-butoxy)-2-methoxy-2-oxoethyl)-2-methyl-4-(p-tolyl)-7,8-dihydro-1,6-naphthyridine-6(5H)-carboxylate (82.4 mg, 72% yield) as a colorless oil. $^1$H NMR (400 MHz, $CDCl_3$) δ ppm 7.01-7.78 (m, 9H), 5.13 (s, 2H), 4.97 (s, 1H), 4.29-4.32 (m, 1H), 4.05-4.10 (m, 1H), 3.78-3.81 (m, 2H), 3.71 (s, 3H), 3.06 (bs, 2H), 2.64 (s, 3H), 2.45 (s, 3H) 0.99 (s, 9H). LCMS (M+H) calcd for $C_{31}H_{37}N_2O_5$: 517.27. found: 517.4.

Intermediate 15

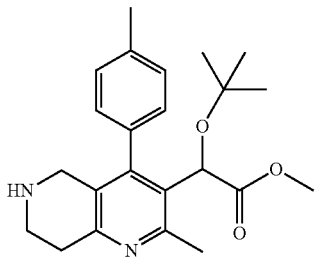 [SMILES: COC(=O)C(OC(C)(C)C)c1c(C)nc2c(c1-c1ccc(C)cc1)CNCC2]

Methyl 2-(tert-butoxy)-2-(2-methyl-4-(p-tolyl)-5,6,7,8-tetrahydro-1,6-naphthyridin-3-yl)acetate To a solution of benzyl 3-(1-(tert-butoxy)-2-methoxy-2-oxoethyl)-2-methyl-4-(p-tolyl)-7,8-dihydro-1,6-naphthyridine-6(5H)-carboxylate (intermediate 12) (0.100 g, 0.194 mmol) in $CH_2Cl_2$ (2 ml) and methanol (2 ml) was added 10% Pd/C (10.30 mg, 9.68 mmol) followed by HCl (0.024 ml, 0.290 mmol). The mixture was shaken under $H_2$ (50 psi) for 3 h. Celite was added and the mixture was filtered over Celite rinsing with MeOH. Concentration gave a residue which was then dissolved in MeOH and re-filtered then concentrated. The residue was triturated with $Et_2O$ and the solids were collected by filtration to give methyl 2-(tert-butoxy)-2-(2-methyl-4-(p-tolyl)-5,6,7,8-tetrahydro-1,6-naphthyridin-3-yl)acetate 2 HCl as a white solid. $^1$H NMR (400 MHz, $CD_3OD$) δ ppm 7.44 (t, J=8.44 Hz, 2H), 7.24 (dd, J=6.85, 18.34 Hz, 2H), 5.08 (s, 1H), 4.10-4.26 (m, 1H), 3.70-3.85 (m, 4H), 3.57-3.70 (m, 2H), 3.21-3.31 (m, 2H), 2.66 (s, 3H), 2.47 (s, 3H), 0.99 (s, 9H). LCMS (M+H) calcd for $C_{23}H_{31}N_2O_3$: 383.21. found: 383.1.

Intermediate 16

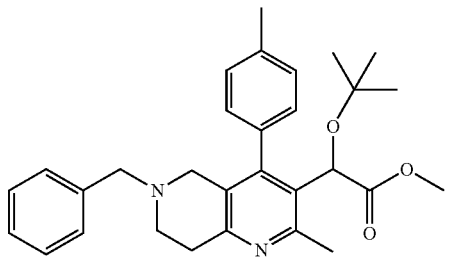 [SMILES: COC(=O)C(OC(C)(C)C)c1c(C)nc2c(c1-c1ccc(C)cc1)CN(Cc1ccccc1)CC2]

Methyl 2-(6-benzyl-2-methyl-4-(p-tolyl)-5,6,7,8-tetrahydro-1,6-naphthyridin-3-yl)-2-(tert-butoxy)acetate To a solution of methyl 2-(tert-butoxy)-2-(2-methyl-4-(p-tolyl)-5,6,7,8-tetrahydro-1,6-naphthyridin-3-yl)acetate, 2 HCl (intermediate 13) (0.042 g, 100 mmol) in acetonitrile (2.5 mL) were added BnBr (0.014 mL, 120 mmol) followed by $iPr_2NEt$ (0.052 mL, 300 mmol). The resulting mixture was stirred at room temperature. After 1.5 h, the mixture was washed with water and the organic phase was dried ($Na_2SO_4$), filtered and concentrated to give methyl 2-(6-benzyl-2-methyl-4-(p-tolyl)-5,6,7,8-tetrahydro-1,6-naphthyridin-3-yl)-2-(tert-butoxy)acetate (0.048 g, 102% yield) as a colorless oil. $^1$H NMR (400 MHz, $CDCl_3$) δ ppm 7.39-7.45 (m, 1H), 7.25-7.32 (m, 5H), 7.23 (d, J=7.58 Hz, 1H), 7.14-7.21 (m, 1H), 7.05 (dd, J=1.71, 7.82 Hz, 1H), 4.96 (s, 1H), 3.70 (s, 3H), 3.44-3.66 (m, 2H), 3.12-3.41 (m, 2H), 2.96-3.08 (m, 2H), 2.63-2.85 (m, 2H), 2.62 (s, 3H), 2.44 (s, 3H), 0.98 (s, 9H). LCMS (M+H) calcd for $C_{30}H_{37}N_2O_3$: 473.28. found: 473.4.

Intermediate 17

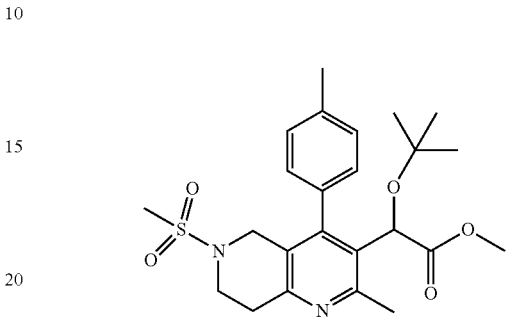

Methyl 2-(tert-butoxy)-2-(2-methyl-6-(methylsulfonyl)-4-(p-tolyl)-5,6,7,8-tetrahydro-1,6-naphthyridin-3-yl)acetate To a solution of methyl 2-(tert-butoxy)-2-(2-methyl-4-(p-tolyl)-5,6,7,8-tetrahydro-1,6-naphthyridin-3-yl)acetate, HCl (intermediate 13) (0.042 g, 100 μmol) in $CH_2Cl_2$ (2 mL) was added $Et_3N$ (0.049 mL, 350 μmol) and the solution cooled to 0° C. Methanesulfonyl chloride (7.74 μl, 100 μmol) was added and the mixture was stirred at 0° C. After 1.5 h, the reaction was quenched with sat'd aq $NaHCO_3$. The organic phase was dried ($Na_2SO_4$), filtered and concentrated to provide methyl 2-(tert-butoxy)-2-(2-methyl-6-(methylsulfonyl)-4-(p-tolyl)-5,6,7,8-tetrahydro-1,6-naphthyridin-3-yl)acetate (0.052 g, 113% yield) as a colorless oil that crystallized upon standing. $^1$H NMR (400 MHz, $CDCl_3$) δ ppm 7.22-7.35 (m, 2H), 7.16 (dd, J=1.83, 7.70 Hz, 1H), 7.04 (dd, J=1.71, 7.58 Hz, 1H), 4.93 (s, 1H), 4.11 (d, J=16.14 Hz, 1H), 3.84 (d, J=16.14 Hz, 1H), 3.70 (s, 3H), 3.51-3.69 (m, 2H), 3.15 (t, J=5.99 Hz, 2H), 2.76 (s, 3H), 2.62 (s, 3H), 2.44 (s, 3H), 0.98 (s, 9H). LCMS (M+H) calcd for $C_{24}H_{33}N_2O_5S$: 461.21. found: 461.3.

Intermediate 18

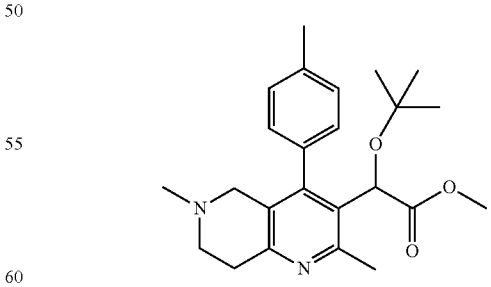

Methyl 2-(tert-butoxy)-2-(2,6-dimethyl-4-(p-tolyl)-5,6,7,8-tetrahydro-1,6-naphthyridin-3-yl)acetate To a solution of methyl 2-(tert-butoxy)-2-(2-methyl-4-(p-tolyl)-5,6,7,8-tetrahydro-1,6-naphthyridin-3-yl)acetate, HCl (intermediate 13) (0.042 g, 0.10 mmol) in THF (1 mL) were added 37% (H₂O) formaldehyde (0.011 mL, 0.150 mmol), acetic acid (0.333 mL) and NaBH(OAc)₃ (0.033 g, 0.150 mmol). The resulting mixture was stirred at room temperature for 2 h. The mixture was concentrated and purified by preparative HPLC (10% CH₃CN/90% H₂O/0.1% NH4OAc; Sunfire 30×100 mm, C18, 5 μm). Concentration of the product-containing fractions gave methyl 2-(tert-butoxy)-2-(2,6-dimethyl-4-(p-tolyl)-5,6,7,8-tetrahydro-1,6-naphthyridin-3-yl)acetate (0.040 g, 101% yield) as a white paste.

Intermediate 19

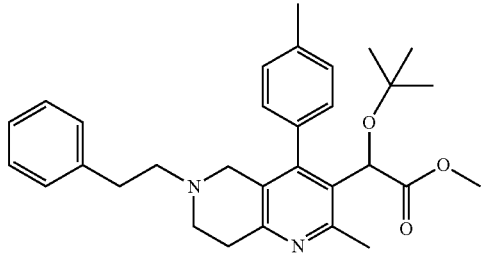 [SMILES: COC(=O)C(OC(C)(C)C)c1c(C)nc2c(c1-c1ccc(C)cc1)CN(CCc1ccccc1)CC2]

Methyl 2-(tert-butoxy)-2-(2-methyl-6-phenethyl-4-(p-tolyl)-5,6,7,8-tetrahydro-1,6-naphthyridin-3-yl)acetate To a solution of methyl 2-(tert-butoxy)-2-(2-methyl-4-(p-tolyl)-5,6,7,8-tetrahydro-1,6-naphthyridin-3-yl)acetate, HCl (intermediate 13) (0.030 g, 0.072 mmol) in THF (0.716 ml) were added 2-phenylethanal (0.014 ml), acetic acid (0.239 ml) and NaHCO₃ (0.024 g, 0.107 mmol). The resulting mixture was stirred at room temperature for 2 h. The mixture was concentrated and purified by preparative HPLC (10% MeOH/90% H₂O/0.1% CF₃CO₂H, Phenomonex 30×100 mm, C18, 5 μm).

Intermediate 20

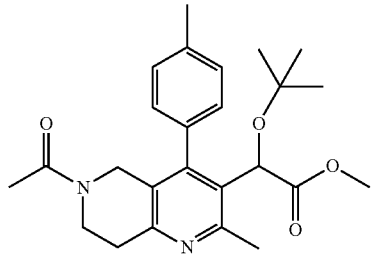 [SMILES: COC(=O)C(OC(C)(C)C)c1c(C)nc2c(c1-c1ccc(C)cc1)CN(C(C)=O)CC2]

Methyl 2-(6-acetyl-2-methyl-4-(p-tolyl)-5,6,7,8-tetrahydro-1,6-naphthyridin-3-yl)-2-(tert-butoxy)acetate To a solution of methyl 2-(tert-butoxy)-2-(2-methyl-4-(p-tolyl)-5,6,7,8-tetrahydro-1,6-naphthyridin-3-yl)acetate, HCl (intermediate 13) (0.040 g, 0.095 mmol) in CH₂Cl₂ (2 mL) was added iPr₂NEt (0.050 mL, 0.286 mmol) followed by acetyl chloride (7.47 μl, 0.105 mmol) and the mixture was stirred at room temperature overnight. Additional acetyl chloride (7.47 μl, 0.105 mmol) was added along with iPr₂NEt (0.050 mL, 0.286 mmol) and the mixture was stirred an additional 6 h. The mixture was washed with water and the organic phase was dried (Na₂SO₄), filtered and concentrated to give crude methyl 2-(6-acetyl-2-methyl-4-(p-tolyl)-5,6,7,8-tetrahydro-1,6-naphthyridin-3-yl)-2-(tert-butoxy)acetate as a brown oil that was carried on without further purification.

Intermediate 21

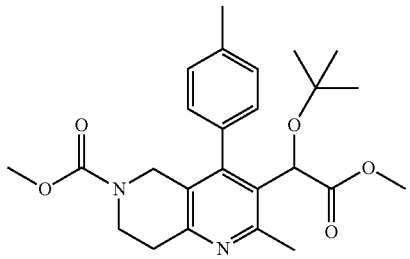

Methyl 3-(1-(tert-butoxy)-2-methoxy-2-oxoethyl)-2-methyl-4-(p-tolyl)-7,8-dihydro-1,6-naphthyridine-6(5H)-carboxylate To a solution of methyl 2-(tert-butoxy)-2-(2-methyl-4-(p-tolyl)-5,6,7,8-tetrahydro-1,6-naphthyridin-3-yl)acetate, HCl (intermediate 13) (0.040 g, 0.095 mmol) in THF (2 mL) was added Et₃N (0.032 mL, 0.229 mmol) and methyl carbonochloridate (10.83 mg, 0.115 mmol) and the mixture stirred at room temperature for 1 h. The mixture was washed with water and the organic phase was dried (Na₂SO₄), filtered and concentrated. The crude residue was carried on as is.

Intermediate 22

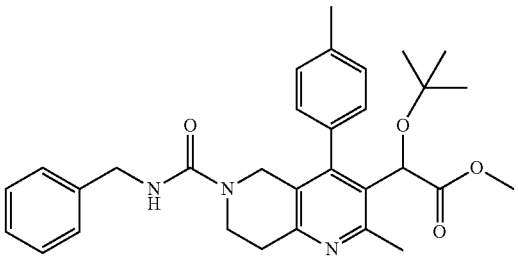 [SMILES: COC(=O)C(OC(C)(C)C)c1c(C)nc2c(c1-c1ccc(C)cc1)CN(C(=O)NCc1ccccc1)CC2]

Methyl 2-(6-(benzylcarbamoyl)-2-methyl-4-(p-tolyl)-5,6,7,8-tetrahydro-1,6-naphthyridin-3-yl)-2-(tert-butoxy)acetate To a solution of methyl 2-(tert-butoxy)-2-(2-methyl-4-(p-tolyl)-5,6,7,8-tetrahydro-1,6-naphthyridin-3-yl)acetate, HCl (intermediate 13) (0.03 g, 0.072 mmol) in CH₂Cl₂ (2 mL) was added Et₃N (0.040 mL, 0.286 mmol) followed by (isocyanatomethyl)benzene (9.66 μl, 0.079 mmol) and the resulting solution stirred at room temperature for 4 h. The reaction mixture was washed with sat'd aq NaHCO₃ and the organic phase concentrated to give methyl 2-(6-(benzylcarbamoyl)-2-methyl-4-(p-tolyl)-5,6,7,8-tetrahydro-1,6-naphthyridin-3-yl)-2-(tert-butoxy)acetate as a colorless oil. LCMS (M+H)

calcd for $C_{31}H_{38}N_3O_4$: 516.28. found: 516.3. The product was carried on without further purification.

Intermediate 23

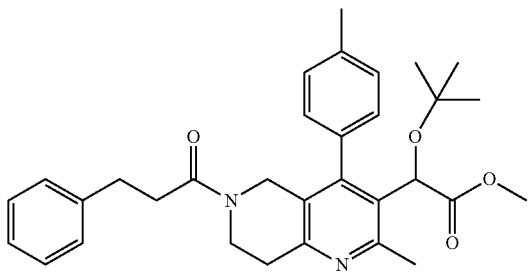 [SMILES: COC(=O)C(OC(C)(C)C)c1c(C)nc2c(c1-c1ccc(C)cc1)CN(C(=O)CCc1ccccc1)CC2]

Methyl 2-(tert-butoxy)-2-(2-methyl-6-(3-phenylpropanoyl)-4-(p-tolyl)-5,6,7,8-tetrahydro-1,6-naphthyridin-3-yl)acetate To a solution of methyl 2-(tert-butoxy)-2-(2-methyl-4-(p-tolyl)-5,6,7,8-tetrahydro-1,6-naphthyridin-3-yl)acetate, HCl (intermediate 13) (0.03 g, 0.072 mmol) in $CH_2Cl_2$ (2 mL) was added $iPr_2NEt$ (0.038 mL, 0.215 mmol) followed by 3-phenylpropanoyl chloride (0.013 g, 0.079 mmol) and the resulting solution stirred at room temperature for 4 h. The reaction mixture was washed with sat'd aq $NaHCO_3$ and the organic phase was concentrated to give methyl 2-(tert-butoxy)-2-(2-methyl-6-(3-phenylpropanoyl)-4-(p-tolyl)-5,6,7,8-tetrahydro-1,6-naphthyridin-3-yl)acetate as a colorless oil. LCMS (M+H) calcd for $C_{32}H_{39}FN_2O_4$: 515.29. found: 515.4. The product was carried on without further purification.

Intermediate 24

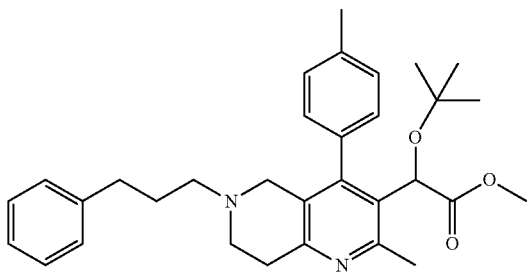 [SMILES: COC(=O)C(OC(C)(C)C)c1c(C)nc2c(c1-c1ccc(C)cc1)CN(CCCc1ccccc1)CC2]

Methyl 2-(tert-butoxy)-2-(2-methyl-6-(3-phenylpropyl)-4-(p-tolyl)-5,6,7,8-tetrahydro-1,6-naphthyridin-3-yl)acetate To a solution of methyl 2-(tert-butoxy)-2-(2-methyl-4-(p-tolyl)-5,6,7,8-tetrahydro-1,6-naphthyridin-3-yl)acetate, HCl (intermediate 13) (0.03 g, 0.072 mmol) in acetonitrile (2 mL) was added $K_2CO_3$ (0.022 g, 0.158 mmol) followed by (3-chloropropyl)benzene (10.25 μl, 0.072 mmol). The resulting mixture was stirred at 75° C. for 48 h. The mixture was concentrated and the residue was partitioned between EtOAc and water. The organic fraction was dried ($Na_2SO_4$), filtered and concentrated to give methyl 2-(tert-butoxy)-2-(2-methyl-6-(3-phenylpropyl)-4-(p-tolyl)-5,6,7,8-tetrahydro-1,6-naphthyridin-3-yl)acetate as a colorless oil which was carried on without further purification.

Intermediate 25

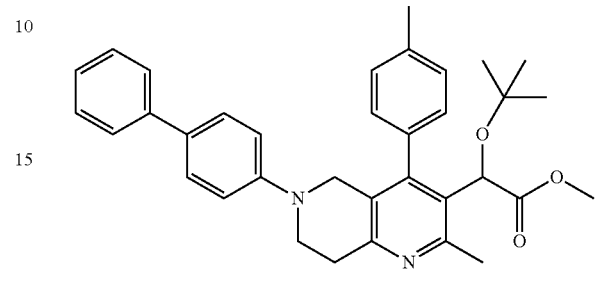

Methyl 2-(6-([1,1'-biphenyl]-4-yl)-2-methyl-4-(p-tolyl)-5,6,7,8-tetrahydro-1,6-naphthyridin-3-yl)-2-(tert-butoxy)acetate A solution of methyl 2-(tert-butoxy)-2-(2-methyl-4-(p-tolyl)-5,6,7,8-tetrahydro-1,6-naphthyridin-3-yl)acetate, HCl (intermediate 13) (0.040 g, 0.095 mmol), $Et_3N$ (0.013 mL, 0.095 mmol) and 4-bromo-1,1'-biphenyl (0.032 mL, 0.191 mmol) was added to a mixture of trisdibenzylideneacetonedipalladium chloroform complex (4.94 mg, 4.77 μmol), 2-dicyclohexylphosphino-2',6'-dimethoxy-1,1'-biphenyl (S-Phos) (3.92 mg, 9.55 μmol) and sodium-t-butoxide (0.018 g, 0.191 mmol) in a dry, $N_2$ flushed, flask. The resulting mixture was stirred at 110° C. for 4 h then cooled to room temperature and diluted with water. The organic phase was dried ($Na_2SO_4$), filtered and concentrated to provide methyl 2-(6-([1,1'-biphenyl]-4-yl)-2-methyl-4-(p-tolyl)-5,6,7,8-tetrahydro-1,6-naphthyridin-3-yl)-2-(tert-butoxy)acetate (0.035 g, 68% yield) as a yellow oil. $^1$H NMR (400 MHz, $CDCl_3$) δ ppm 7.50-7.60 (m, 2H), 7.44 (t, J=7.46 Hz, 2H), 7.21-7.40 (m, 5H), 7.14 (dd, J=1.71, 7.83 Hz, 1H), 6.98-7.08 (m, 2H), 6.79 (dd, J=1.96, 8.31 Hz, 1H), 5.01 (s, 1H), 4.11 (d, J=16.38 Hz, 1H), 3.86 (d, J=16.38 Hz, 1H), 3.58-3.82 (m, 5H), 3.19 (q, J=5.79 Hz, 2H), 2.65 (s, 3H), 2.48 (s, 3H), 1.01 (s, 9H). LCMS (M+H) calcd for $C_{35}H_{39}N_2O_3$: 535.29. found: 535.1.

Intermediate 26

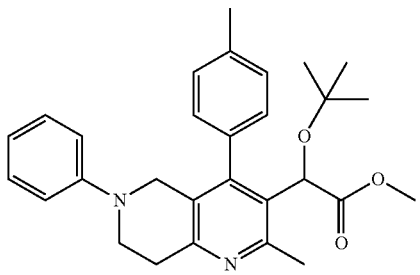 [SMILES: COC(=O)C(OC(C)(C)C)c1c(C)nc2c(c1-c1ccc(C)cc1)CN(c1ccccc1)CC2]

Methyl 2-(tert-butoxy)-2-(2-methyl-6-phenyl-4-(p-tolyl)-5,6,7,8-tetrahydro-1,6-naphthyridin-3-yl)acetate A solution of methyl 2-(tert-butoxy)-2-(2-methyl-4-(p-tolyl)-5,6,7,8-tetrahydro-1,6-naphthyridin-3-yl)acetate, HCl (intermediate 13) (0.040 g, 0.095 mmol), Et$_3$N (0.013 mL, 0.095 mmol) and bromobenzene (0.020 mL, 0.191 mmol) was added to a mixture of trisdibenzylideneacetone-dipalladium chloroform complex (4.94 mg, 4.77 μmol), 2-dicyclohexylphosphino-2',6'-dimethoxy-1,1'-biphenyl (S-Phos) (3.92 mg, 9.55 μmol) and sodium-t-butoxide (0.018 g, 0.191 mmol) in a dry, N$_2$ flushed, flask. The resulting mixture was stirred at 110° C. for 4 h then cooled to room temperature and diluted with water. The organic phase was dried (Na$_2$SO$_4$), filtered and concentrated to provide methyl 2-(tert-butoxy)-2-(2-methyl-6-phenyl-4-(p-tolyl)-5,6,7,8-tetrahydro-1,6-naphthyridin-3-yl)acetate (0.0507 g, 116% yield) as a yellow oil. The material was carried on without purification. LCMS (M+H) calcd for C$_{29}$H$_{35}$N$_2$O$_3$: 459.26. found: 459.1.

Intermediate 27

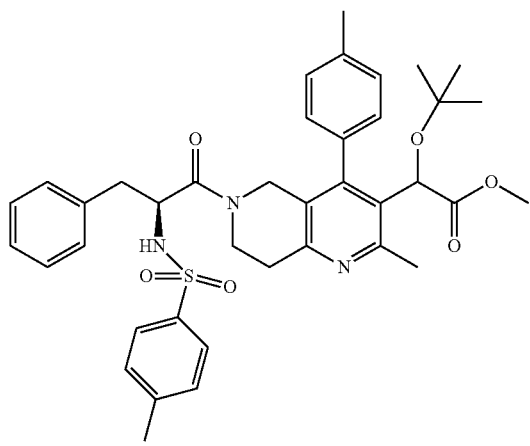 [SMILES: COC(=O)C(OC(C)(C)C)c1c(C)nc2c(c1-c1ccc(C)cc1)CN(C(=O)[C@H](Cc1ccccc1)NS(=O)(=O)c1ccc(C)cc1)CC2]

Methyl 2-(tert-butoxy)-2-(2-methyl-6-(2-(4-methylphenylsulfonamido)-3-phenylpropanoyl)-4-(p-tolyl)-5,6,7,8-tetrahydro-1,6-naphthyridin-3-yl)acetate To a solution of 2-(4-methylphenylsulfonamido)-3-phenylpropanoic acid (0.038 g, 0.119 mmol) and iPr$_2$NEt (0.083 mL, 0.477 mmol) in DMF (2 mL) was added O-(7-azabenzotriazol-1-yl)-N,N,N',N'-tetramethyluronium hexafluorophosphate (HATU) (0.054 g, 0.143 mmol) and the solution stirred at room temperature for 15 min. Added to this was methyl 2-(tert-butoxy)-2-(2-methyl-4-(p-tolyl)-5,6,7,8-tetrahydro-1,6-naphthyridin-3-yl)acetate, HCl (intermediate 13) (0.05 g, 0.119 mmol) and the resulting solution stirred at room temperature for 18 h. Additional O-(7-azabenzotriazol-1-yl)-N,N,N',N'-tetramethyluronium hexafluorophosphate (HATU) (0.054 g, 0.143 mmol) was added and the mixture was stirred at room temperature for 3 h. The mixture was diluted with water and extracted with EtOAc. The organic phase was washed with brine, dried (Na$_2$SO$_4$), filtered and concentrated to give methyl 2-(tert-butoxy)-2-(2-methyl-6-(2-(4-methylphenylsulfonamido)-3-phenylpropanoyl)-4-(p-tolyl)-5,6,7,8-tetrahydro-1,6-naphthyridin-3-yl)acetate as a yellow oil. The product was carried on without further purification.

Example 1

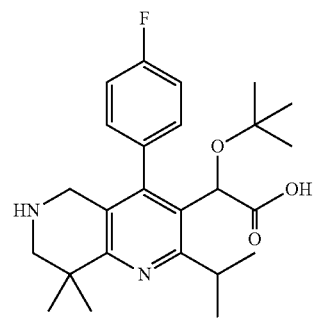 [SMILES: CC(C)c1nc2c(c(-c3ccc(F)cc3)c1C(OC(C)(C)C)C(=O)O)CNCC2(C)C]

2-tert-Butoxy-2-(4-(4-fluorophenyl)-2-isopropyl-8,8-dimethyl-5,6,7,8-tetrahydro-1,6-naphthyridin-3-yl)acetic acid A solution of methyl 2-tert-butoxy-2-(4-(4-fluorophenyl)-2-isopropyl-8,8-dimethyl-6-(2,2,2-trifluoroacetyl)-5,6,7,8-tetrahydro-1,6-naphthyridin-3-yl)acetate (intermediate 4) (0.483 g, 0.897 mmol) and 1N NaOH (4.48 ml) in MeOH (10 mL) was stirred at room temperature overnight (15 h) and then 8 h at reflux. After cooling the product was purified by preparative-HPLC (CH$_3$CN/H$_2$O, 10 mmol NH$_4$OAc) to provide 2-tert-butoxy-2-(4-(4-fluorophenyl)-2-isopropyl-8,8-dimethyl-5,6,7,8-tetrahydro-1,6-naphthyridin-3-yl)acetic acid (0.126 g, 31% yield). $^1$H NMR (500 MHz, DMSO-d$_6$) δ ppm 7.37 (2H, d, J=6.7 Hz), 7.31 (2H, d, J=6.7 Hz), 4.67 (1H, s), 3.59 (1H, d, J=16.2 Hz), 3.51-3.57 (1H, m), 3.33 (2H, br. s.), 3.10 (1H, d, J=16.2 Hz), 2.72-2.82 (2H, m), 1.28 (6H, s), 1.19 (3H, d, J=6.4 Hz), 1.07 (3H, d, J=6.7 Hz), 0.87 (9H, s). LCMS (M+H) calcd for C$_{25}$H$_{34}$FN$_2$O$_3$: 429.26. found: 429.3.

Example 2

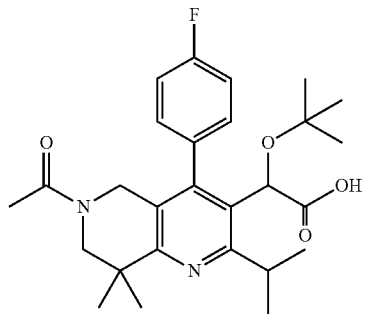 [SMILES: CC(=O)N1Cc2c(nc(C(C)C)c(C(OC(C)(C)C)C(=O)O)c2-c2ccc(F)cc2)C(C)(C)C1]

2-(6-Acetyl-4-(4-fluorophenyl)-2-isopropyl-8,8-dimethyl-5,6,7,8-tetrahydro-1,6-naphthyridin-3-yl)-2-tert-butoxyacetic acid To a stirred solution of 2-tert-butoxy-2-(4-(4-fluorophenyl)-2-isopropyl-8,8-dimethyl-5,6,7,8-tetrahydro-1,6-naphthyridin-3-yl)acetic acid (example 1) (0.012 g, 0.028 mmol) and Et$_3$N (0.139 ml, 1 mmol) in CH$_2$Cl$_2$ (5 mL) was added Ac$_2$O (0.026 ml, 0.280 mmol) at room temperature. After 3 h, the reaction mixture concentrated and purified by preparative-HPLC (MeCN/H$_2$O/NH$_4$OAc) to afford 2-(6-acetyl-4-(4-fluorophenyl)-2-isopropyl-8,8-dimethyl-5,6,7,8-tetrahydro-1,6-naphthyridin-3-yl)-2-tert-butoxyacetic acid (0.011 g, 76% yield) as white powder and mixture of rotomers. $^1$H NMR (500 MHz, CDCl$_3$) δ ppm 7.41-7.54 (1H, m), 7.11-7.23 (3H, m), 4.91 (1H, br. s.), 4.49 (0.7H, d, J=17.4 Hz), 4.28 (0.3H, d, J=16.5Hz), 4.08 (0.7H, d, J=17.7 Hz), 3.93 (0.3H, d, J=16.8 Hz), 3.39-3.52 (2H, m), 3.15-3.27 (1H, m), 2.15 (2H, s), 1.95 (1H, s), 1.27-1.39 (9H, m), 1.15 (3H, d, J=5.5Hz), 0.90 (3H, s), 1.00 (6H, s). LCMS (M+H) calcd for C27H36FN2O4: 471.27. found: 471.3.

Example 3

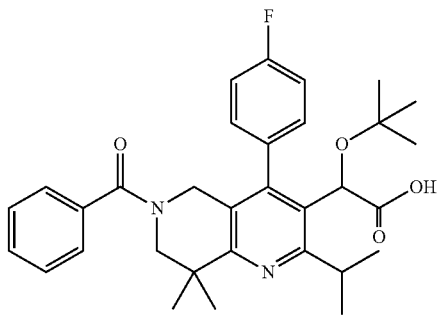 [SMILES: CC(C)c1nc2c(c(-c3ccc(F)cc3)c1C(OC(C)(C)C)C(=O)O)CN(C(=O)c1ccccc1)CC2(C)C]

2-(6-Benzoyl-4-(4-fluorophenyl)-2-isopropyl-8,8-dimethyl-5,6,7,8-tetrahydro-1,6-naphthyridin-3-yl)-2-tert-butoxyacetic acid To a stirred turbid mixture of 2-tert-butoxy-2-(4-(4-fluorophenyl)-2-isopropyl-8,8-dimethyl-5,6,7,8-tetrahydro-1,6-naphthyridin-3-yl)acetic acid (example 1) (0.0105 g, 0.025 mmol) and Et$_3$N (0.017 ml, 0.123 mmol) in CH$_2$Cl$_2$ (2 mL) was added benzoyl chloride (8.53 μl, 0.074 mmol) at room temperature. After 3 h, the reaction mixture concentrated and purified by preparative-HPLC (MeCN/H$_2$O/NH$_4$OAc) to afford 2-(6-benzoyl-4-(4-fluorophenyl)-2-isopropyl-8,8-dimethyl-5,6,7,8-tetrahydro-1,6-naphthyridin-3-yl)-2-tert-butoxyacetic acid (0.0102 g, 77% yield) as a white powder. $^1$H NMR (500 MHz, CD$_3$OD) δ ppm 6.94-7.58 (9H, m), 4.79 (1H, br. s.), 4.59 (0.5H, d, J=17.4 Hz), 4.40 (0.5H, d, J=17.7 Hz), 4.30 (0.5H, d, J=16.5Hz), 4.00 (0.5H, d, J=12.5 Hz), 3.92 (0.5H, d, J=16.5Hz), 3.77 (0.5H, d, J=12.8 Hz), 3.54-3.64 (2H, m), 1.43 (3H, d, J=19.2 Hz), 1.12-1.35 (9H, m), 0.98 (4H, br. s.), 0.94 (5H, br. s.). LCMS (M+H) calcd for C$_{32}$H$_{38}$FN$_2$O$_4$: 533.28. found: 533.4.

Example 4

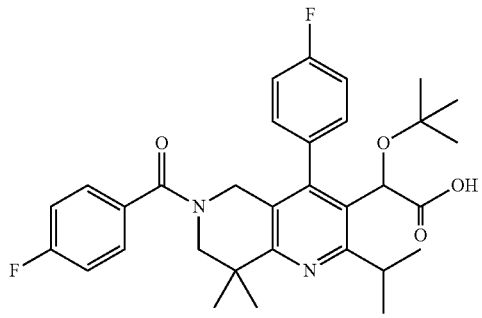 [SMILES: CC(C)c1nc2c(c(-c3ccc(F)cc3)c1C(OC(C)(C)C)C(=O)O)CN(C(=O)c1ccc(F)cc1)CC2(C)C]

2-tert-Butoxy-2-(6-(4-fluorobenzoyl)-4-(4-fluorophenyl)-2-isopropyl-8,8-dimethyl-5,6,7,8-tetrahydro-1,6-naphthyridin-3-yl)acetic acid To a stirred turbid mixture of 2-tert-butoxy-2-(4-(4-fluorophenyl)-2-isopropyl-8,8-dimethyl-5,6,7,8-tetrahydro-1,6-naphthyridin-3-yl)acetic acid (example 1) (0.0103 g, 0.024 mmol) and Et$_3$N (0.017 ml, 0.120 mmol) in CH$_2$Cl$_2$ (2 mL) was added 4-fluorobenzoyl chloride (8.52 μl, 0.072 mmol) at room temperature. After 3 h, the reaction mixture concentrated and purified by preparative-HPLC (MeCN/H$_2$O/NH$_4$OAc) to afford 2-tert-butoxy-2-(6-(4-fluorobenzoyl)-4-(4-fluorophenyl)-2-isopropyl-8,8-dimethyl-5,6,7,8-tetrahydro-1,6-naphthyridin-3-yl)acetic acid (0.0104 g, 77% yield) as white powder. $^1$H NMR (500 MHz, CD$_3$OD) δ ppm 6.98-7.59 (8H, m), 4.75-4.87 (1H, br. s.), 4.57 (0.5H, d, J=17.7 Hz), 4.40 (0.5H, d, J=17.7 Hz), 4.31 (0.5H, d, J=17.7 Hz), 4.02 (0.5H, d, J=11.6 Hz), 3.92 (0.5H, d, J=15.3 Hz), 3.73 (0.5H, d, J=12.5Hz), 3.53-3.78 (2H, m), 1.37-1.48 (3H, m), 1.19-1.35 (6H, m), 1.15 (3H, d, J=6.1 Hz), 0.96 (9H, br. s.). LCMS (M+H) calcd for C$_{32}$H$_{37}$FN$_2$O$_4$: 551.27. found: 551.4.

Example 5

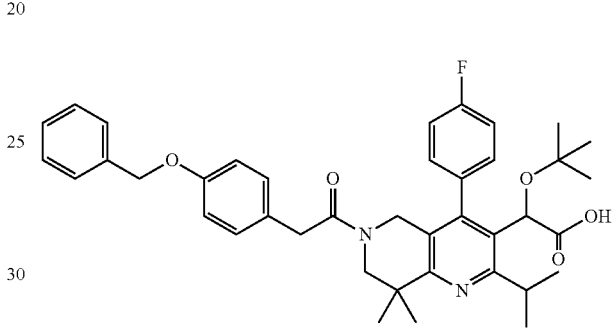

2-(6-(2-(4-(Benzyloxy)phenyl)acetyl)-4-(4-fluorophenyl)-2-isopropyl-8,8-dimethyl-5,6,7,8-tetrahydro-1,6-naphthyridin-3-yl)-2-tert-butoxyacetic acid To a stirred solution of methyl 2-(4-(4-fluorophenyl)-2-isopropyl-8,8-dimethyl-5,6,7,8-tetrahydro-1,6-naphthyridin-3-yl)-2-hydroxyacetate, 2 HCl (intermediate 3) (0.05 g, 0.109 mmol) and iPr$_2$NEt (0.095 ml, 0.544 mmol) in CH$_2$Cl$_2$ (5 mL) was added 2-(4-(benzyloxy)phenyl)acetyl chloride (0.028 g, 0.109 mmol) at room temperature. After 2 h, the reaction mixture was taken up in Et$_2$O (25 mL), washed with satd NaHCO$_3$ (25 mL), brine (25 mL), dried (Na$_2$SO$_4$), filtered and concentrated to afford a brown paste. To a stirred solution of this material product and tert-butyl acetate (0.441 ml, 3.27 mmol) in CH$_2$Cl$_2$ (3 mL) was added 70% perchloric acid (0.028 ml, 0.327 mmol) at room temperature. After 2 h, the reaction mixture was diluted with Et$_2$O (30 mL), washed with satd NaHCO$_3$ (10 mL), brine (10 mL), dried (Na$_2$SO$_4$), filtered and concentrated to afford a white solid which was used in the next step with out purification. A solution of the solid and 1N NaOH (0.44 ml) in MeOH (2 ml) was stirred at 70° C. for 20 h. The mixture was cooled and purified by preparative-HPLC (MeCN/H$_2$O/NH$_4$OAc) to afford 2-(6-(2-(4-(benzyloxy)phenyl)acetyl)-4-(4-fluorophenyl)-2-isopropyl-8,8-dimethyl-5,6,7,8-tetrahydro-1,6-naphthyridin-3-yl)-2-tert-butoxyacetic acid (0.0216 g, 28.9% yield); $^1$H NMR (500 MHz, CDCl$_3$) δ ppm 7.29-7.44 (5H, m), 7.04-7.22 (4H, m), 6.91 (2H, d, J=8.5Hz), 6.79-6.86 (2H, m), 5.03 (2H, s), 4.86-4.97 (1H, m), 4.48-4.61 (1H, m), 4.01-4.11 (1H, m), 3.88 (1H, d, J=16.8 Hz), 3.71 (1H, s), 3.51-3.57 (1H, m), 3.43-3.50 (1H, m), 3.14-3.21 (1H, m), 1.32 (3H, d, J=7.6 Hz), 1.27-1.31 (6H, m), 1.16 (3H, d, J=5.2 Hz), 0.99 (9H, s). LCMS (M+H) calcd for C$_{40}$H$_{46}$FN$_2$O$_5$: 653.34. found: 653.3.

Example 6

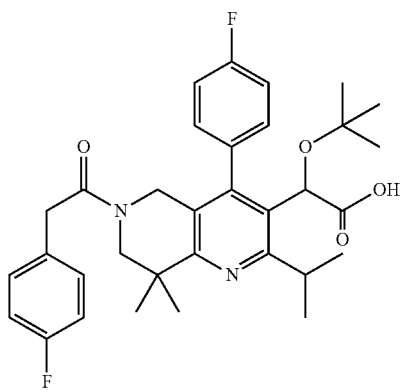 [SMILES: CC(C)c1nc2c(c(-c3ccc(F)cc3)c1C(OC(C)(C)C)C(=O)O)CN(C(=O)Cc1ccc(F)cc1)CC2(C)C]

2-tert-Butoxy-2-(4-(4-fluorophenyl)-6-(2-(4-fluorophenyl)acetyl)-2-isopropyl-8,8-dimethyl-5,6,7,8-tetrahydro-1,6-naphthyridin-3-yl)acetic acid To a solution of 2-tert-butoxy-2-(4-(4-fluorophenyl)-2-isopropyl-8,8-dimethyl-5,6,7,8-tetrahydro-1,6-naphthyridin-3-yl)acetic acid (example 1) (10.1 mg, 0.024 mmol) in $CH_2Cl_2$ (5 mL) was added $Et_3N$ (9.85 μl, 0.071 mmol) followed by 2-(4-fluorophenyl)acetyl chloride (6.10 mg, 0.035 mmol) and the resulting mixture stirred at room temperature. (Mixture became a clear, colorless solution within 30 min.) After 3 h, the solvent was removed and the residue was taken up in MeOH/DMF and purified by preparative HPLC (10% AcCN/90% $H_2O$/0.1% $NH_4OAc$, Sunfire 19×100 mm, C18, 5 μm). The product containing fractions were concentrated to remove the organic solvent and the resulting precipitate isolated by filtration and washed with water to give 2-tert-butoxy-2-(4-(4-fluorophenyl)-6-(2-(4-fluorophenyl)acetyl)-2-isopropyl-8,8-dimethyl-5,6,7,8-tetrahydro-1,6-naphthyridin-3-yl)acetic acid (1.6 mg, 11.78% yield) as a white solid. $^1H$ NMR (400 MHz, $CD_3OD$) δ ppm 7.13-7.53 (5H, m), 6.88-7.09 (3H, m), 4.80-4.88 (1H, m), 4.32-4.46 (0.5H, m), 4.18-4.32 (1H, m), 3.97 (0.5H, d, J=16.56 Hz), 3.79-3.92 (1.5H, m), 3.55-3.68 (3H, m), 3.52 (0.5H, d, J=13.05 Hz), 1.37 (3H, d, J=6.53 Hz), 1.32 (3H, d, J=7.53 Hz), 1.27 (3H, dd, J=6.27, 5.02 Hz), 1.15 (3H, dd, J=6.53, 4.77 Hz), 0.91-1.06 (9H, m). $^{19}F$ NMR (400 MHz, $CD_3OD$) δ ppm −114.90, −115.19, −117.98, −118.41. LCMS (M+H) calcd for $C_{33}H_{39}F_2N_2O_4$: 565.28. found: 565.4.

Example 7

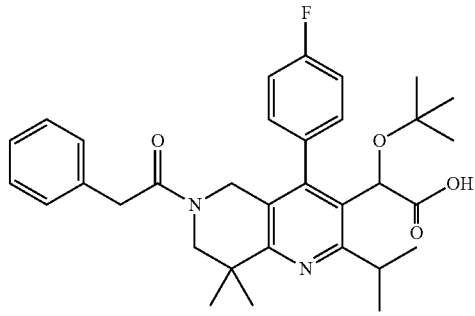 [SMILES: CC(C)c1nc2c(c(-c3ccc(F)cc3)c1C(OC(C)(C)C)C(=O)O)CN(C(=O)Cc1ccccc1)CC2(C)C]

2-tert-Butoxy-2-(4-(4-fluorophenyl)-2-isopropyl-8,8-dimethyl-6-(2-phenylacetyl)-5,6,7,8-tetrahydro-1,6-naphthyridin-3-yl)acetic acid To a solution of 2-tert-butoxy-2-(4-(4-fluorophenyl)-2-isopropyl-8,8-dimethyl-5,6,7,8-tetrahydro-1,6-naphthyridin-3-yl)acetic acid (example 1) (9.2 mg, 0.021 mmol) in $CH_2Cl_2$ (5 mL) was added $Et_3N$ (8.98 μl, 0.064 mmol) followed by 2-phenylacetyl chloride (4.26 μl, 0.032 mmol) and the mixture stirred at room temperature. (Mixture became a clear, colorless solution within 30 min.) After 3 h, the solvent was removed and the residue was taken up in MeOH/DMF and purified by preparative HPLC (10% AcCN/90% $H_2O$/0.1% $NH_4OAc$, Sunfire 19×100 mm, C18, 5 μm). The product was dissolved in MeOH and repurified by preparative HPLC (10% AcCN/90% $H_2O$/0.1% $NH_4OAc$, Sunfire 19×100 mm, C18, 5 μm) to give 2-tert-butoxy-2-(4-(4-fluorophenyl)-2-isopropyl-8,8-dimethyl-6-(2-phenylacetyl)-5,6,7,8-tetrahydro-1,6-naphthyridin-3-yl)acetic acid (1.3 mg, 10% yield) as a white solid. $^1H$ NMR (500 MHz, $CD_3OD$) δ ppm 7.38-7.60 (1H, m), 7.00-7.40 (7H, m), 6.97 (1H, d, J=7.02 Hz), 4.75-4.85 (1H, m), 4.35-4.47 (0.5H, m), 4.17-4.34 (1H, m), 3.98 (0.5H, d, J=16.48 Hz), 3.77-3.93 (1.5H, m), 3.57-3.77 (3H, m), 3.53 (0.5H, d, J=13.12 Hz), 1.22-1.42 (9H, m), 1.11-1.22 (3H, m), 0.87-1.04 (9H, m). LCMS (M+H) calcd for $C_{33}H_{40}FN_2O_4$: 547.29. found: 547.4.

Example 8

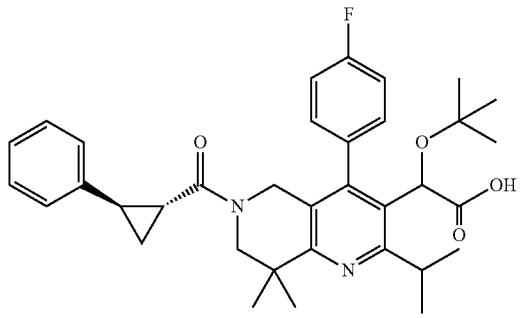 [SMILES: CC(C)c1nc2c(c(-c3ccc(F)cc3)c1C(OC(C)(C)C)C(=O)O)CN(C(=O)[C@@H]1C[C@H]1c1ccccc1)CC2(C)C]

2-tert-Butoxy-2-(4-(4-fluorophenyl)-2-isopropyl-8,8-dimethyl-6-((1R,2R)-2-phenylcyclopropanecarbonyl)-5,6,7,8-tetrahydro-1,6-naphthyridin-3-yl)acetic acid To a solution of 2-tert-butoxy-2-(4-(4-fluorophenyl)-2-isopropyl-8,8-dimethyl-5,6,7,8-tetrahydro-1,6-naphthyridin-3-yl)acetic acid (example 1) (10 mg, 0.023 mmol) in $CH_2Cl_2$ (5 mL) was added $Et_3N$ (0.020 mL, 0.140 mmol) and the mixture cooled to 0° C. Added to this was (1R,2R)-2-phenylcyclopropanecarbonyl chloride (10 μl, 0.07 mmol) and the mixture stirred at room temperature (mixture became a clear colorless solution over time). After 1 h, 0.5 mL MeOH was added and the mixture was concentrated under a stream of air, taken up in MeOH and purified by preparative HPLC (10% AcCN/90% $H_2O$/0.1% $CF_3CO_2H$, Sunfire 19×100 mm, C18, 5 μm). The product-containing fractions were combined, concentrated to remove the organic solvent and the resulting precipitate isolated by filtration to give 2-tert-butoxy-2-(4-(4-fluorophenyl)-2-isopropyl-8,8-dimethyl-6-((1R,2R)-2-phenylcyclopropanecarbonyl)-5,6,7,8-tetrahydro-1,6-naphthyridin-3-yl)acetic acid (5.5 mg, 39% yield) as a white solid. $^1H$ NMR (500 MHz, $CD_3OD$) δ ppm 6.61-7.66 (9H, m), 4.70-4.87 (1H, m), 4.09-4.63 (2H, m), 3.40-4.02 (3H, m), 2.24-2.49 (1H, m), 2.06-2.23 (1H, m), 1.80-1.96 (1H, m), 1.45-1.76 (1H, m), 1.20-1.45 (10H, m), 1.11-1.19 (3H, m), 0.86-1.03 (8H, m). $^{19}F$ NMR (500 MHz, $CD_3OD$) δ ppm −115.29, −115.86. LCMS (M+H) calcd for $C_{12}H_{42}FN_2O_4$: 573.31. found: 573.08.

Example 9

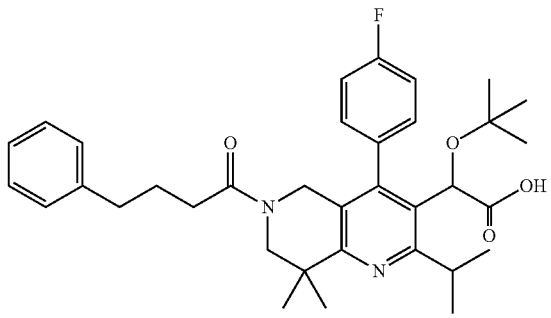 [SMILES: CC(C)c1nc2c(c(-c3ccc(F)cc3)c1C(OC(C)(C)C)C(=O)O)CN(C(=O)CCCc1ccccc1)CC2(C)C]

2-tert-Butoxy-2-(4-(4-fluorophenyl)-2-isopropyl-8,8-dimethyl-6-(4-phenylbutanoyl)-5,6,7,8-tetrahydro-1,6-naphthyridin-3-yl)acetic acid To a solution of 2-tert-butoxy-2-(4-(4-fluorophenyl)-2-isopropyl-8,8-dimethyl-5,6,7,8-tetrahydro-1,6-naphthyridin-3-yl)acetic acid (example 1) (10 mg, 0.023 mmol) in $CH_2Cl_2$ (5 mL) was added $Et_3N$ (0.020 mL, 0.140 mmol) and the resulting mixture cooled to 0° C. Added to this was 4-phenylbutanoyl chloride (12.79 mg, 0.070 mmol) and the mixture stirred at room temperature (mixture became a clear colorless solution over time). After 1 h, 0.5 mL MeOH was added and the mixture was concentrated under a stream of air, taken up in MeOH and purified by preparative HPLC (10% AcCN/90% $H_2O$/0.1% $CF_3CO_2H$, Sunfire 19×100 mm, C18, 5 μm). The product-containing fractions were combined, concentrated to remove the organic solvent and the resulting precipitate isolated by filtration to give 2-tert-butoxy-2-(4-(4-fluorophenyl)-2-isopropyl-8,8-dimethyl-6-(4-phenylbutanoyl)-5,6,7,8-tetrahydro-1,6-naphthyridin-3-yl)acetic acid (7.7 mg, 55% yield) as a white solid. $^1H$ NMR (400 MHz, $CD_3OD$) δ ppm 7.41-7.57 (1H, m), 7.12-7.40 (7H, m), 7.02-7.12 (1H, m), 4.88 (1H, s), 4.29-4.42 (1H, m), 4.15-4.29 (0.5H, m), 3.80-4.06 (1H, m), 3.44-3.70 (2.5H, m), 2.67 (1H, t, J=7.53 Hz), 2.57 (0.5H, t, J=7.40 Hz), 2.34-2.53 (2H, m), 2.20 (0.5H, t, J=7.53 Hz), 1.74-1.98 (2H, m), 1.23-1.42 (9H, m), 1.16 (3H, dd, J=6.65, 4.39 Hz), 0.88-1.09 (9H, m). $^{19}F$ NMR (400 MHz, $CD_3OD$) δ ppm −114.74, −115.22. LCMS (M+H) calcd for $C_{35}H_{44}FN_2O_4$: 575.32. found: 575.02.

Example 10

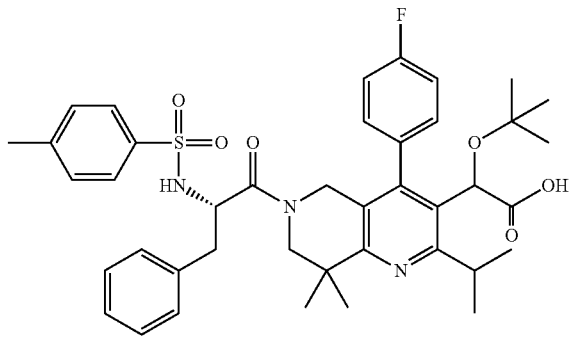 [SMILES: Cc1ccc(S(=O)(=O)N[C@@H](Cc2ccccc2)C(=O)N2Cc3c(nc(C(C)C)c(C(OC(C)(C)C)C(=O)O)c3-c3ccc(F)cc3)C(C)(C)C2)cc1]

2-tert-Butoxy-2-(4-(4-fluorophenyl)-2-isopropyl-8,8-dimethyl-6-(2-(4-methylphenylsulfonamido)-3-phenylpropanoyl)-5,6,7,8-tetrahydro-1,6-naphthyridin-3-yl)acetic acid To a solution of 2-tert-butoxy-2-(4-(4-fluorophenyl)-2-isopropyl-8,8-dimethyl-5,6,7,8-tetrahydro-1,6-naphthyridin-3-yl)acetic acid (example 1) (10 mg, 0.023 mmol) in $CH_2Cl_2$ (5 mL) was added $Et_3N$ (0.020 mL, 0.140 mmol) and the resulting mixture cooled to 0° C. Added to this was 2-(4-methylphenylsulfonamido)-3-phenylpropanoyl chloride (23.65 mg, 0.070 mmol) and the mixture stirred at room temperature (mixture became a clear colorless solution over time). After 1 h, 0.5 mL MeOH was added and the mixture was concentrated under a stream of air and taken up in MeOH and purified by preparative HPLC (10% AcCN/90% $H_2O$/0.1% $NH_4OAc$, Sunfire 19×100 mm, C18, 5 μm column) The product-containing fractions were concentrated to remove the organic solvent and the resulting precipitate was collected by filtration to give 2-tert-butoxy-2-(4-(4-fluorophenyl)-2-isopropyl-8,8-dimethyl-6-(2-(4-methylphenylsulfonamido)-3-phenylpropanoyl)-5,6,7,8-tetrahydro-1,6-naphthyridin-3-yl)acetic acid (3.7 mg, 21% yield) as a white solid. $^1H$ NMR (400 MHz, $CD_3OD$) δ ppm 7.56-7.80 (1H, m), 6.91-7.57 (12H, m), 6.71-6.92 (1H, m), 4.85 (1H, s), 3.99-4.26 (1H, m), 3.78-4.00 (0.5H, m), 3.46-3.77 (1.5H, m), 3.36-3.46 (2H, m), 3.13-3.28 (1H, m), 2.60-2.87 (2H, m), 2.11-2.50 (3H, m), 0.85-1.46 (21H, m). $^{19}F$ NMR (400 MHz, $CD_3OD$) δ ppm −114.16, −115.11, −117.98, −118.41. LCMS (M+H) calcd for $C_{41}H_{49}FN_3O_6$: 730.33. found: 730.03.

Example 11

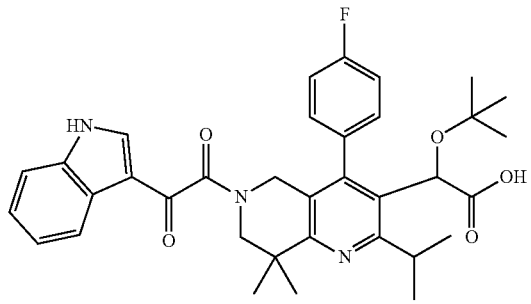 [SMILES: CC(C)c1nc2c(c(-c3ccc(F)cc3)c1C(OC(C)(C)C)C(=O)O)CN(C(=O)C(=O)c1c[nH]c3ccccc13)CC2(C)C]

2-(6-(2-(1H-Indol-3-yl)-2-oxoacetyl)-4-(4-fluorophenyl)-2-isopropyl-8,8-dimethyl-5,6,7,8-tetrahydro-1,6-naphthyridin-3-yl)-2-tert-butoxyacetic acid To a solution of 2-tert-butoxy-2-(4-(4-fluorophenyl)-2-isopropyl-8,8-dimethyl-5,6,7,8-tetrahydro-1,6-naphthyridin-3-yl)acetic acid (example 1) (10 mg, 0.023 mmol) in $CH_2Cl_2$ (5 mL) was added $Et_3N$ (0.020 mL, 0.140 mmol) and the resulting mixture cooled to 0° C. Added to this was 2-(1H-indol-3-yl)-2-oxoacetyl chloride (14.5 mg, 0.070 mmol) and the mixture stirred at room temperature (mixture became a clear colorless solution over time). After 1 h, 0.5 mL MeOH was added and the mixture was concentrated under a stream of air, taken up in MeOH and purified by preparative HPLC (10% AcCN/90% $H_2O$/0.1% $NH_4OAc$, Sunfire 19×100 mm, C18, 5 μm column). The product was repurified by preparative HPLC (10% AcCN/90% $H_2O$/0.1% $NH_4OAc$, Sunfire 19×100 mm, C18, 5 μm column). The product-containing fractions were combined, concentrated to remove the organic solvent and the resulting precipitate collected by filtration to give 2-(6-(2-(1H-indol-3-yl)-2-oxoacetyl)-4-(4-fluorophenyl)-2-isopropyl-8,8-dimethyl-5,6,7,8-tetrahydro-1,6-naphthyridin-3-yl)-2-tert-butoxyacetic acid (2.4 mg, 16% yield) as a white solid. $^1$H NMR (500 MHz, CD$_3$OD) δ ppm 8.24 (0.5H, d, J=5.80 Hz), 8.13 (0.5H, d, J=7.32 Hz), 8.05 (0.5H, s), 7.82 (0.5H, s), 7.48-7.68 (2H, m), 7.24-7.48 (4H, m), 7.09 (0.5H, t, J=5.80 Hz), 6.80-6.92 (0.5H, m), 6.71-6.80 (0.5H, m), 6.59-6.71 (0.5H, m), 4.72 (0.5H, s), 4.58 (0.5H, d, J=18.01 Hz), 4.37 (1H, dd, J=17.24, 8.09 Hz), 3.96 (0.5H, d, J=16.79 Hz), 3.77-3.93 (1H, m), 3.55-3.72 (2.5H, m), 1.49 (3H, d, J=7.02 Hz), 1.23-1.38 (6H, m), 1.17 (3H, t, J=5.80 Hz), 0.85-1.05 (9H, m). $^{19}$F NMR (500 MHz, CD$_3$OD) δ ppm −115.51. LCMS (M+H) calcd for C$_{35}$H$_{39}$FN$_3$O$_5$: 600.28. found: 600.3.

Example 12

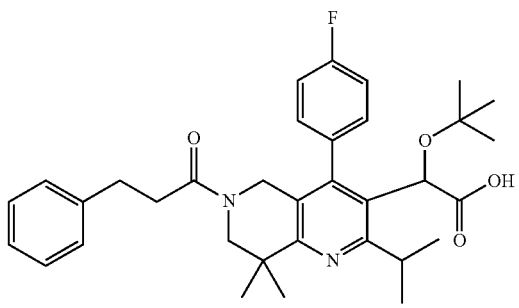 [SMILES: CC(C)c1nc2c(c(-c3ccc(F)cc3)c1C(OC(C)(C)C)C(=O)O)CN(C(=O)CCc1ccccc1)CC2(C)C]

2-tert-Butoxy-2-(4-(4-fluorophenyl)-2-isopropyl-8,8-dimethyl-6-(3-phenylpropanoyl)-5,6,7,8-tetrahydro-1,6-naphthyridin-3-yl)acetic acid $^1$H NMR (400 MHz, CD$_3$OD) δ ppm 7.49-7.63 (1H, m), 7.07-7.41 (7H, m), 7.02 (1H, d, J=7.03 Hz), 4.83 (1H, d, J=5.02 Hz), 4.17-4.42 (1.5H, m), 3.81-4.05 (1H, m), 3.54-3.72 (1.5H, m), 3.43-3.54 (1H, m), 2.87-2.98 (1H, m), 2.68-2.87 (2H, m), 2.38-2.62 (1H, m), 1.35 (3H, s), 1.24-1.31 (6H, m), 1.16 (3H, dd, J=6.53, 2.76 Hz), 0.97 (9H, s). $^{19}$F NMR (400 MHz, CD$_3$OD) δ ppm −115.02. −115.42. LCMS (M+H) calcd for C$_{34}$H$_{42}$FN$_2$O$_4$: 561.30. found: 561.08.

Example 13

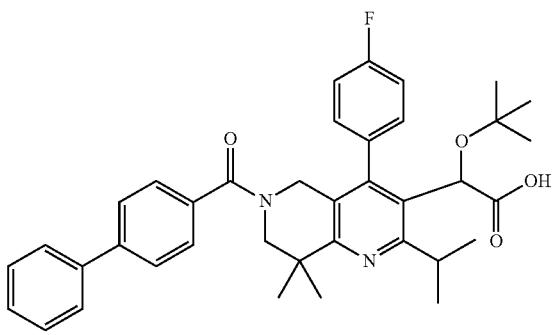 [SMILES: CC(C)c1nc2c(c(-c3ccc(F)cc3)c1C(OC(C)(C)C)C(=O)O)CN(C(=O)c1ccc(-c3ccccc3)cc1)CC2(C)C]

2-(6-(Biphenylcarbonyl)-4-(4-fluorophenyl)-2-isopropyl-8,8-dimethyl-5,6,7,8-tetrahydro-1,6-naphthyridin-3-yl)-2-tert-butoxyacetic acid $^1$H NMR (500 MHz, CD$_3$OD) δ ppm 7.60-7.81 (4H, m), 7.21-7.60 (8H, m), 6.89-7.17 (1H, m), 4.84 (1H, br. s.), 4.54-4.73 (0.5H, m), 4.40-4.54 (0.5H, m), 4.26-4.41 (0.5H, m), 3.91-4.20 (1H, m), 3.82 (0.5H, d, J=10.99 Hz), 3.54-3.77 (2H, m), 1.39-1.54 (3H, m), 1.22-1.40 (6H, m), 1.18 (3H, d, J=5.19 Hz), 0.95-1.07 (9H, m). $^{19}$F NMR (500 MHz, CD$_3$OD) δ ppm −115.44, −78.04. LCMS (M+H) calcd for C$_{38}$H$_{42}$FN$_2$O$_4$: 609.31. found: 609.5.

Example 14

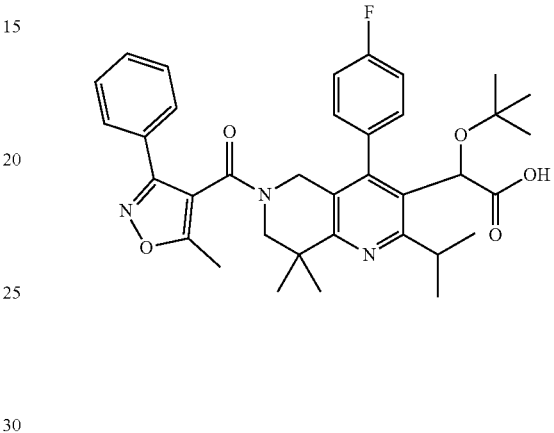

2-tert-Butoxy-2-(4-(4-fluorophenyl)-2-isopropyl-8,8-dimethyl-6-(5-methyl-3-phenylisoxazole-4-carbonyl)-5,6,7,8-tetrahydro-1,6-naphthyridin-3-yl)acetic acid To a solution of 2-tert-butoxy-2-(4-(4-fluorophenyl)-2-isopropyl-8,8-dimethyl-5,6,7,8-tetrahydro-1,6-naphthyridin-3-yl)acetic acid (6.9 mg, 0.016 mmol) in CH$_2$Cl$_2$ (2 mL) was added oxalyl chloride (0.042 mL, 0.483 mmol) and the resulting mixture was stirred at room temperature. After stirring at room temperature overnight, additional oxalyl chloride (0.042 mL, 0.483 mmol) was added along with catalytic DMF and the mixture was stirred at room temperature for 2 h. The solution was concentrated and the solid was taken up in CH$_2$Cl$_2$ (1 mL) and added to a mixture of 2-tert-butoxy-2-(4-(4-fluorophenyl)-2-isopropyl-8,8-dimethyl-5,6,7,8-tetrahydro-1,6-naphthyridin-3-yl)acetic acid (6.9 mg, 0.016 mmol) in CH$_2$Cl$_2$ (5 mL) and Et$_3$N (0.022 mL, 0.161 mmol) that was cooled to 0° C. The resulting mixture was stirred at room temperature for 1 h. 1 mL MeOH was added and solution concentrated. The residue was taken up in CH$_3$CN and purified by preparative HPLC (10% CH$_3$CN/90% H$_2$O/0.1% NH$_4$OAc, Sunfire 19×100 mm, C18, 5 μm column). The product-containing fraction was concentrated to give a white solid that was repurified by preparative HPLC (10% CH$_3$CN/90% H$_2$O/0.1% CF$_3$CO$_2$H, Sunfire 19×150 mm, C18, 5 μm column) 2-tert-butoxy-2-(4-(4-fluorophenyl)-2-isopropyl-8,8-dimethyl-6-(5-methyl-3-phenylisoxazole-4-carbonyl)-5,6,7,8-tetrahydro-1,6-naphthyridin-3-yl)acetic acid, 2 CF$_3$CO$_2$H (2.4 mg, 16% yield) was obtained as a white solid. $^1$H NMR (500 MHz, CD$_3$OD) δ ppm 7.65 (1H, dd, J=7.48, 1.98 Hz), 6.97-7.57 (8H, m), 4.84-4.88 (1H, m), 3.80-4.83 (2.5H, m), 3.48-3.81 (2.5H, m), 2.29-2.52 (3H, m), 1.21-1.38 (9H, m), 1.14 (3H, d, J=7.02 Hz), 0.91-1.03 (9H, m). $^{19}$F NMR (500 MHz, CD$_3$OD) δ ppm −114.87, −77.39. LCMS (M+H) calcd for C$_{36}$H$_{41}$FN$_3$O$_5$: 614.30. found: 614.08.

Example 15

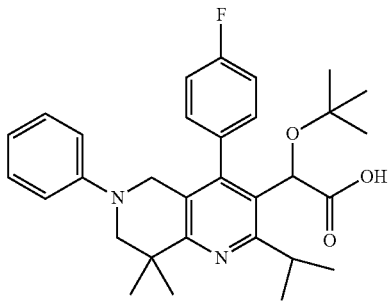 [SMILES: CC(C)c1nc2c(c(-c3ccc(F)cc3)c1C(OC(C)(C)C)C(=O)O)CN(c1ccccc1)CC2(C)C]

2-tert-Butoxy-2-(4-(4-fluorophenyl)-2-isopropyl-8,8-dimethyl-6-phenyl-5,6,7,8-tetrahydro-1,6-naphthyridin-3-yl)acetic acid A mixture of methyl 2-tert-butoxy-2-(4-(4-fluorophenyl)-2-isopropyl-8,8-dimethyl-6-phenyl-5,6,7,8-tetrahydro-1,6-naphthyridin-3-yl)acetate (intermediate 6) (5.0 mg, 9.64 µmol) and lithium hydroxide monohydrate (1.214 mg, 0.029 mmol) in 1.5 mL of 4:1 MeOH/H$_2$O was stirred at room temperature for 2 h. 1N NaOH (0.2 mL) was added and the reaction was stirred at 70° C. for 16 h. The mixture was purified by preparative HPLC (10% CH$_3$CN/90% H$_2$O/0.1% CF$_3$CO$_2$H, Xterra 19×100 mm, C18, 5 µm column). The product-containing fraction was concentrated to remove the organic solvent and the resulting precipitate collected by filtration to give 2-tert-butoxy-2-(4-(4-fluorophenyl)-2-isopropyl-8,8-dimethyl-6-phenyl-5,6,7,8-tetrahydro-1,6-naphthyridin-3-yl)acetic acid, CF$_3$CO$_2$H (1.4 mg, 22% yield) as a pale yellow solid. $^1$H NMR (400 MHz, CD$_3$OD) δ ppm 7.52 (ddd, J=8.0, 5.5, 2.3 Hz, 1H), 7.45-7.37 (m, 1H), 7.36-7.24 (m, 2H), 7.23-7.14 (m, 2H), 6.82-6.73 (m, 3H), 3.99 (d, J=15.6 Hz, 1H), 3.68-3.56 (m, 2H), 3.45-3.38 (m, 1.5H), 3.30-3.23 (m, 1.5H), 1.46 (d, J=5.0 Hz, 6H), 1.31 (d, J=3.8 Hz, 3H), 1.19 (d, J=6.8 Hz, 3H), 1.01 (s, 9H). $^{19}$F NMR (400 MHz, CD$_3$OD) δ ppm −115.19, −76.98. LCMS (M+H) calcd for C$_{31}$H$_{38}$FN$_2$O$_3$: 505.28. found: 505.4.

Example 16

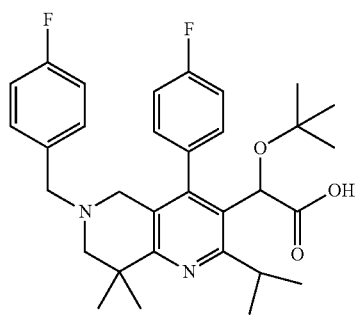 [SMILES: CC(C)c1nc2c(c(-c3ccc(F)cc3)c1C(OC(C)(C)C)C(=O)O)CN(Cc1ccc(F)cc1)CC2(C)C]

2-tert-Butoxy-2-(6-(4-fluorobenzyl)-4-(4-fluorophenyl)-2-isopropyl-8,8-dimethyl-5,6,7,8-tetrahydro-1,6-naphthyridin-3-yl)acetic acid A solution of methyl 2-tert-butoxy-2-(6-(4-fluorobenzyl)-4-(4-fluorophenyl)-2-isopropyl-8,8-dimethyl-5,6,7,8-tetrahydro-1,6-naphthyridin-3-yl)acetate (intermediate 7) (11.56 mg, 0.021 mmol) and 1N NaOH (0.21 mL) in MeOH (1 mL) was stirred at 70° C. After stirring for 16 h at 70° C., LiOH—H$_2$O (1.2 mg) was added and the mixture and stirring continued for an additional 2 h. The mixture was cooled to room temperature and purified by preparative HPLC (10% CH$_3$CN/90% H$_2$O/0.1% CF$_3$CO$_2$H, Xterra 19×100 mm, C18, 5 µm column). The product-containing fractions were concentrated to remove the organic solvent and the resulting precipitate was collected by filtration to give 2-tert-butoxy-2-(6-(4-fluorobenzyl)-4-(4-fluorophenyl)-2-isopropyl-8,8-dimethyl-5,6,7,8-tetrahydro-1,6-naphthyridin-3-yl)acetic acid, 2 CF$_3$CO$_2$H (3.4 mg, 19% yield) as a white solid. $^1$H NMR (400 MHz, CD$_3$OD) δ ppm 7.55-7.46 (m, 1H), 7.42 (dd, J=8.5, 5.3 Hz, 2H), 7.37-7.23 (m, 3H), 7.16 (t, J=8.7 Hz, 2H), 4.28-3.89 (m, 3H), 3.67-3.52 (m, 1.5H), 3.47-3.37 (m, 1.5H), 1.44 (d, J=10.5Hz, 6H), 1.29 (d, J=6.5Hz, 3H), 1.16 (d, J=6.5Hz, 3H), 0.97 (s, 9H). $^{19}$F NMR (400 MHz, CD$_3$OD) δ ppm −76.94, −114.26. LCMS (M+H) calcd for C$_{32}$H$_{39}$F$_2$N$_2$O$_3$: 537.29. found: 537.4.

Example 17

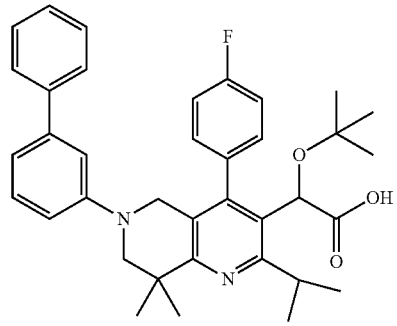 [SMILES: CC(C)c1nc2c(c(-c3ccc(F)cc3)c1C(OC(C)(C)C)C(=O)O)CN(c1cccc(-c3ccccc3)c1)CC2(C)C]

2-(6-([1,1'-Biphenyl]-3-yl)-4-(4-fluorophenyl)-2-isopropyl-8,8-dimethyl-5,6,7,8-tetrahydro-1,6-naphthyridin-3-yl)-2-(tert-butoxy)acetic acid A mixture of methyl 2-(6-([1,1'-biphenyl]-3-yl)-4-(4-fluorophenyl)-2-isopropyl-8,8-dimethyl-5,6,7,8-tetrahydro-1,6-naphthyridin-3-yl)-2-(tert-butoxy)acetate (intermediate 8) (10 mg, 0.017 mmol), lithium hydroxide monohydrate (2.12 mg, 0.05 mmol) and 1N NaOH (0.17 mL) were stirred at 70° C. for 16 h. The mixture was then filtered and purified by preparative HPLC (10% CH$_3$CN/90% H$_2$O/0.1% CF$_3$CO$_2$H, Xterra 19×100 mm, C18, 5 µm column) to give 2-(6-([1,1'-biphenyl]-3-yl)-4-(4-fluorophenyl)-2-isopropyl-8,8-dimethyl-5,6,7,8-tetrahydro-1,6-naphthyridin-3-yl)-2-(tert-butoxy)acetic acid (4.2 mg, 41% yield) as a white solid. $^1$H NMR (500 MHz, CD$_3$OD) δ ppm 7.62-7.47 (m, 3H), 7.46-7.38 (m, 3H), 7.38-7.29 (m, 3H), 7.26 (t, J=7.9 Hz, 1H), 7.02 (d, J=7.3 Hz, 1H), 6.96 (s, 1H), 6.77 (dd, J=8.2, 1.5Hz, 1H), 4.92 (d, br. s., 1H), 4.07 (d, J=15.6 Hz, 1H), 3.71 (d, J=15.6 Hz, 1H), 3.63 (dt, J=12.8, 6.4 Hz, 1H), 3.49 (d, J=12.5Hz, 1H), 3.37 (br. s., 1H), 1.48 (d, J=3.7 Hz, 6H), 1.32 (d, J=6.4 Hz, 3H), 1.20 (d, J=6.7 Hz, 3H), 1.01 (s, 9H). $^{19}$F NMR (500 MHz, CD$_3$OD) δ ppm −115.74. LCMS (M+H) calcd for C$_{37}$H$_{42}$FN$_2$O$_3$: 581.3. found: 581.5.

Example 18

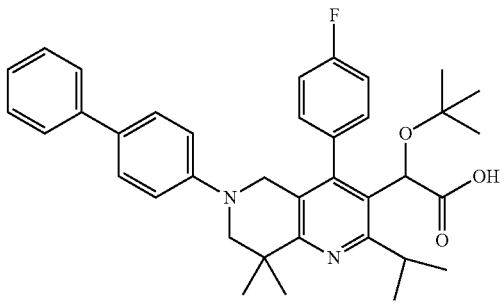 [SMILES: CC(C)c1nc2c(c(-c3ccc(F)cc3)c1C(OC(C)(C)C)C(=O)O)CN(c1ccc(-c3ccccc3)cc1)CC2(C)C]

2-(6-([1,1'-Biphenyl]-4-yl)-4-(4-fluorophenyl)-2-isopropyl-8,8-dimethyl-5,6,7,8-tetrahydro-1,6-naphthyridin-3-yl)-2-(tert-butoxy)acetic acid $^1$H NMR (400 MHz, CD$_3$OD) δ ppm 7.94-7.78 (m, 1H), 7.55 (s, 2H), 7.48 (s, 2H), 7.42-7.32 (m, 3H), 7.30-7.20 (m, 3H), 6.84 (d, J=8.3 Hz, 2H), 4.74 (s, 1H), 4.10 (d, J=15.3 Hz, 1H), 3.87-3.76 (m, 1H), 3.71 (d, J=15.1 Hz, 1H), 3.52-3.44 (m, 2H), 1.45 (d, J=14.8 Hz, 6H), 1.30 (br. s., 3H), 1.24 (d, J=6.8 Hz, 3H), 0.97 (s, 9H). $^{19}$F NMR (400 MHz, CD$_3$OD) δ ppm −116.29. LCMS (M+H) calcd for C$_{37}$H$_{42}$FN$_2$O$_3$: 581.31. found: 581.38.

Example 19

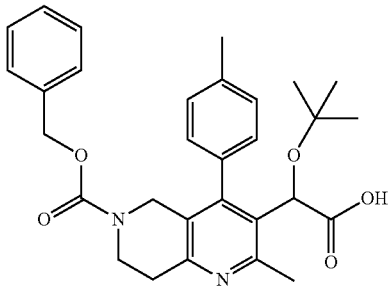 [SMILES: Cc1ccc(-c2c3c(nc(C)c2C(OC(C)(C)C)C(=O)O)CCN(C(=O)OCc2ccccc2)C3)cc1]

2-(6-((Benzyloxy)carbonyl)-2-methyl-4-(p-tolyl)-5,6,7,8-tetrahydro-1,6-naphthyridin-3-yl)-2-(tert-butoxy)acetic acid A solution of benzyl 3-(1-(tert-butoxy)-2-methoxy-2-oxoethyl)-2-methyl-4-(p-tolyl)-7,8-dihydro-1,6-naphthyridine-6(5H)-carboxylate (intermediate 14) (25 mg, 0.048 mmol) in MeOH (1.5 mL) with 1N NaOH (0.48 mL) was stirred at 65° C. for 1 h then at room temperature overnight. The mixture was diluted with water and EtOAc, then neutralized with 1N HCl (0.48 mL). The organic phase was washed with brine, dried (Na$_2$SO$_4$) and concentrated. The residue was purified by preparative HPLC (10% MeOH/90% H$_2$O/0.1% CF$_3$CO$_2$H, Phenomenex-LUNA 21.1×100 mm, C18, 5 μm column). The product-containing fractions were combined and MeOH removed and the remaining aqueous solution lyophilized to provide 2-(6-((benzyloxy)carbonyl)-2-methyl-4-(p-tolyl)-5,6,7,8-tetrahydro-1,6-naphthyridin-3-yl)-2-(tert-butoxy)acetic acid (20.6 mg, 81% yield) as a white powder. $^1$H NMR (400 MHz, CDCl$_3$) δ ppm 7.29-7.59 (m, 8H), 7.05 (br. s., 1H), 5.13 (br. s., 2H), 5.03 (s, 1H), 4.44 (d, J=18.10 Hz, 1H), 4.13 (d, J=18.10 Hz, 1H), 3.22-3.47 (m, 2H), 2.85 (s, 3H), 2.48 (s, 3H), 1.01 (s, 9H). LCMS (M+H) calcd for C$_{30}$H$_{35}$N$_2$O$_5$: 503.25. found: 503.1.

Example 20

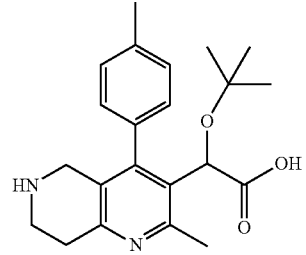 [SMILES: Cc1ccc(-c2c3c(nc(C)c2C(OC(C)(C)C)C(=O)O)CCNC3)cc1]

2-(tert-Butoxy)-2-(2-methyl-4-(p-tolyl)-5,6,7,8-tetrahydro-1,6-naphthyridin-3-yl)acetic acid To a solution of methyl 2-(tert-butoxy)-2-(2-methyl-4-(p-tolyl)-5,6,7,8-tetrahydro-1,6-naphthyridin-3-yl)acetate, HCl (intermediate 15) (0.020 g, 0.048 mmol) in dioxane (2 mL) was added 1N NaOH (0.48 mL) and the mixture was stirred at 65° C. for 3 h. The mixture was neutralized with 1N HCl and concentrated. The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 25-65% B over 40 minutes, then a 5-minute hold at 100% B; Flow: 20 mL/min. Fractions containing the desired product were combined and dried via centrifugal evaporation. $^1$H NMR (500 MHz, DMSO-d$_6$) δ ppm 7.23-7.33 (m, 3H), 7.09 (d, J=7.63 Hz, 1H), 4.71 (s, 1H), 3.62 (d, J=16.17 Hz, 2H), 3.14 (d, J=16.17 Hz, 2H), 2.77-2.85 (m, 2H), 2.47 (s, 3H), 2.39 (s, 3H), 0.86 (s, 9H). LCMS (M+H) calcd for C$_{22}$H$_{29}$N$_2$O$_3$: 369.21. found: 369.1.

Example 21

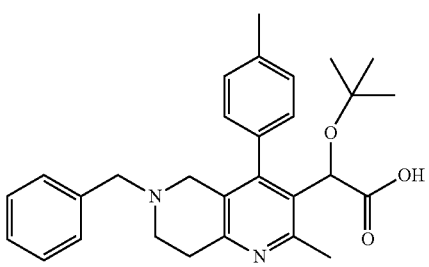 [SMILES: Cc1ccc(-c2c3c(nc(C)c2C(OC(C)(C)C)C(=O)O)CCN(Cc2ccccc2)C3)cc1]

2-(6-Benzyl-2-methyl-4-(p-tolyl)-5,6,7,8-tetrahydro-1,6-naphthyridin-3-yl)-2-(tert-butoxy)acetic acid To a solution of methyl 2-(6-benzyl-2-methyl-4-(p-tolyl)-5,6,7,8-tetrahydro-1,6-naphthyridin-3-yl)-2-(tert-butoxy)acetate (intermediate 16) (47.3 mg, 100 mmol) in dioxane (3 ml)

was added 1N NaOH (1.0 mL) and the mixture was stirred at 70° C. for 1 h. The mixture was quenched with 1 ml 1N HCl and concentrated. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 60-100% B over 30 minutes, then a 5-minute hold at 100% B; Flow: 20 mL/min. Fractions containing the desired product were combined and dried via centrifugal evaporation to provide 2-(6-benzyl-2-methyl-4-(p-tolyl)-5,6,7,8-tetrahydro-1,6-naphthyridin-3-yl)-2-(tert-butoxy)acetic acid (29.9 mg, 65% yield). $^1$H NMR (500 MHz, DMSO-$d_6$) δ ppm 7.20-7.35 (m, 7H), 7.17 (d, J=7.63 Hz, 1H), 7.09 (dd, J=1.53, 7.63 Hz, 1H), 4.77 (s, 1H), 3.44-3.58 (m, 2H), 3.30 (br. s., 1H), 2.99 (d, J=15.56 Hz, 1H), 2.81-2.89 (m, 2H), 2.75 (td, J=5.49, 10.99 Hz, 1H), 2.56-2.65 (m, 1H), 2.48 (s, 3H), 2.37 (s, 3H), 0.87 (s, 9H). LCMS (M+H) calcd for $C_{29}H_{35}N_2O_3$: 459.26. found: 459.3.

Example 22

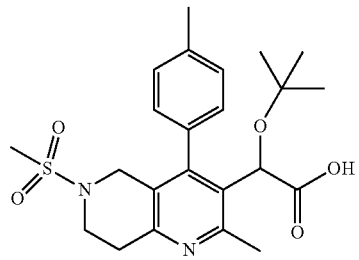 [SMILES: Cc1ccc(-c2c3c(nc(C)c2C(OC(C)(C)C)C(=O)O)CCN(S(C)(=O)=O)C3)cc1]

2-(tert-Butoxy)-2-(2-methyl-6-(methylsulfonyl)-4-(p-tolyl)-5,6,7,8-tetrahydro-1,6-naphthyridin-3-yl)acetic acid $^1$H NMR (500 MHz, DMSO-$d_6$) δ ppm 7.36 (dd, J=7.93, 15.56 Hz, 2H), 7.27 (d, J=7.63 Hz, 1H), 7.17 (dd, J=1.68, 7.78 Hz, 1H), 4.75 (s, 1H), 4.11 (d, J=15.56 Hz, 1H), 3.69 (d, J=15.56 Hz, 1H), 3.56 (td, J=5.65, 11.90 Hz, 1H), 3.40-3.47 (m, 1H), 3.00 (t, J=5.95 Hz, 2H), 2.86 (s, 3H), 2.52 (d, J=1.83 Hz, 3H), 2.41 (s, 3H), 0.87 (s, 9H). LCMS (M+H) calcd for $C_{23}H_{31}N_2O_5$: 447.19. found: 447.3.

Example 23

2-(tert-Butoxy)-2-(2,6-dimethyl-4-(p-tolyl)-5,6,7,8-tetrahydro-1,6-naphthyridin-3-yl)acetic acid $^1$H NMR (500 MHz, DMSO-$d_6$) δ ppm 7.32 (dd, J=7.93, 15.56 Hz, 2H), 7.24 (d, J=7.32 Hz, 1H), 7.12 (dd, J=1.53, 7.63 Hz, 1H), 4.73 (s, 1H), 3.16 (s, 1H), 2.77-2.95 (m, 2H), 2.68-2.77 (m, 1H), 2.54-2.60 (m, 1H), 2.48 (s, 3H), 2.39 (s, 3H), 2.21 (s, 3H), 0.86 (s, 9H). LCMS (M+H) calcd for $C_{23}H_{31}N_2O_3$: 383.23. found: 383.3.

Example 24

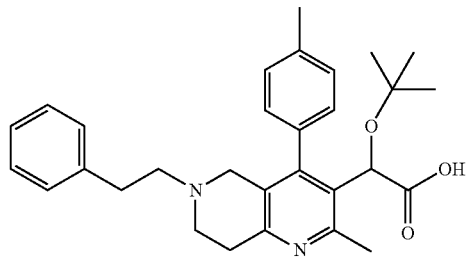

2-(tert-Butoxy)-2-(2-methyl-6-phenethyl-4-(p-tolyl)-5,6,7,8-tetrahydro-1,6-naphthyridin-3-yl)acetic acid To a solution of methyl 2-(tert-butoxy)-2-(2-methyl-6-phenethyl-4-(p-tolyl)-5,6,7,8-tetrahydro-1,6-naphthyridin-3-yl)acetate (intermediate 19) (34.1 mg, 0.070 mmol) in dioxane (1 mL) was added 1N NaOH (0.700 mL) and the reaction was stirred at 75° C. After 1 h, the mixture was cooled to room temperature and neutralized with 0.7 ml 1M HCl then concentrated. The crude material was purified via preparative LC/MS with the following conditions: Column. Waters XBridge C18, 19×200 mm, 5-μm particles; Guard Column. Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 30-100% B over 12 minutes, then a 5-minute hold at 100% B; Flow: 20 mL/min. Fractions containing the desired product were combined and dried via centrifugal evaporation $^1$H NMR (500 MHz, DMSO-$d_6$) δ ppm 7.29-7.38 (m, 2H), 7.21-7.26 (m, 2H), 7.09-7.21 (m, 5H), 4.77 (s, 1H), 3.26 (s, 1H), 2.95 (d, J=14.95 Hz, 1H), 2.88 (br. s., 3H), 2.62-2.76 (m, 3H), 2.58 (d, J=7.02 Hz, 2H), 2.48 (s, 3H), 2.40 (s, 3H), 0.87 (s, 9H). LCMS (M+H) calcd for $C_{30}H_{37}N_2O_3$: 473.28. found: 473.1.

Example 25

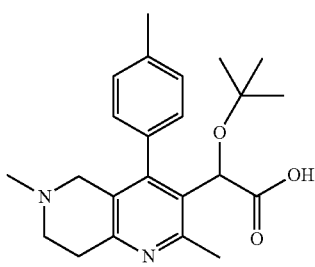 [SMILES: Cc1ccc(-c2c3c(nc(C)c2C(OC(C)(C)C)C(=O)O)CCN(C)C3)cc1]

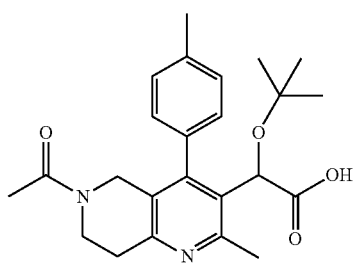 [SMILES: CC(=O)N1CCc2nc(C)c(C(OC(C)(C)C)C(=O)O)c(-c3ccc(C)cc3)c2C1]

2-(6-Acetyl-2-methyl-4-(p-tolyl)-5,6,7,8-tetrahydro-
1,6-naphthyridin-3-yl)-2-(tert-butoxy)acetic acid ¹H NMR (500 MHz, DMSO-d₆) δ ppm 7.36 (dd, J=7.48, 16.02 Hz, 2H), 7.10-7.29 (m, 2H), 4.74-4.85 (m, 1H), 3.57-3.84 (m, 2H), 2.79-3.02 (m, 2H), 2.54-2.68 (m, 2H), 2.50 (br. s., 3H), 2.42 (s, 3H), 1.81-2.08 (m, 3H), 0.82-0.93 (m, 9H). LCMS (M+H) calcd for $C_{24}H_{31}N_2O_4$: 411.22. found: 411.1.

Example 26

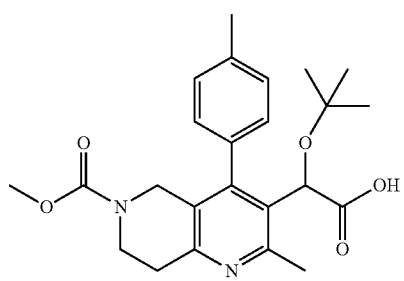 [SMILES: COC(=O)N1CCc2nc(C)c(C(OC(C)(C)C)C(=O)O)c(-c3ccc(C)cc3)c2C1]

2-(tert-Butoxy)-2-(6-(methoxycarbonyl)-2-methyl-4-(p-tolyl)-5,6,7,8-tetrahydro-1,6-naphthyridin-3-yl)
acetic acid ¹H NMR (500 MHz, DMSO-d₆) δ ppm 7.21-7.43 (m, 3H), 7.15 (d, J=7.93 Hz, 1H), 4.73 (br. s., 1H), 4.14-4.34 (m, 1H), 3.87-3.99 (m, 1H), 3.67-3.82 (m, 1H), 3.56 (br. s., 4H), 2.87 (t, J=5.80 Hz, 2H), 2.49 (s, 3H), 2.41 (s, 3H), 0.86 (s, 9H). LCMS (M+H) calcd for $C_{24}H_{31}N_2O_5$: 427.22. found: 427.3.

Example 27

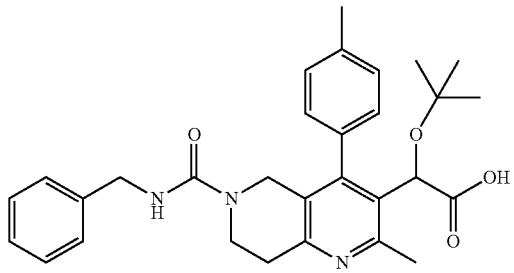 [SMILES: Cc1ccc(-c2c3c(nc(C)c2C(OC(C)(C)C)C(=O)O)CCN(C(=O)NCc2ccccc2)C3)cc1]

2-(6-(Benzylcarbamoyl)-2-methyl-4-(p-tolyl)-5,6,7,
8-tetrahydro-1,6-naphthyridin-3-yl)-2-(tert-butoxy)
acetic acid ¹H NMR (500 MHz, DMSO-d₆) δ ppm 7.11-7.41 (m, 10H), 4.78 (s, 1H), 4.11-4.24 (m, 3H), 3.98 (d, J=17.09 Hz, 1H), 3.71-3.81 (m, 1H), 3.50-3.63 (m, 1H), 2.80-2.96 (m, 2H), 2.49 (s, 3H), 2.40 (s, 3H), 0.87 (s, 9H). LCMS (M+H) calcd for $C_{30}H_{36}N_3O_4$: 502.27. found: 502.3.

Example 28

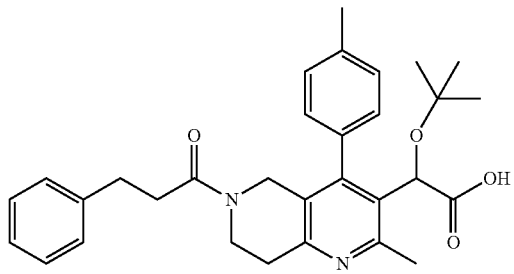 [SMILES: Cc1ccc(-c2c3c(nc(C)c2C(OC(C)(C)C)C(=O)O)CCN(C(=O)CCc2ccccc2)C3)cc1]

2-(tert-Butoxy)-2-(2-methyl-6-(3-phenylpropanoyl)-
4-(p-tolyl)-5,6,7,8-tetrahydro-1,6-naphthyridin-3-yl)
acetic acid ¹H NMR (500 MHz, DMSO-d₆) δ ppm 7.11-7.42 (m, 8H), 7.04 (d, J=7.32 Hz, 1H), 4.71-4.83 (m, 1H), 3.87-4.38 (m, 2H), 3.74-3.84 (m, 1H), 3.59-3.73 (m, 1H), 2.59-2.97 (m, 6H), 2.49 (s, 3H), 2.39-2.43 (m, 3H), 0.87 (s, 9H). LCMS (M+H) calcd for $C_{31}H_{36}N_2O_4$: 501.27. found: 501.3.

Example 29

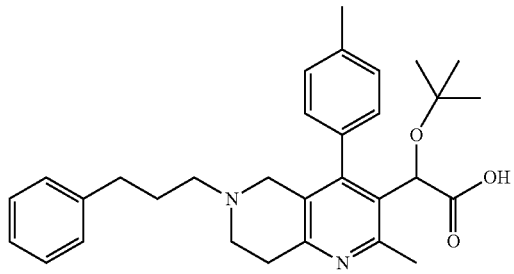 [SMILES: Cc1ccc(-c2c3c(nc(C)c2C(OC(C)(C)C)C(=O)O)CCN(CCCc2ccccc2)C3)cc1]

2-(tert-Butoxy)-2-(2-methyl-6-(3-phenylpropyl)-4-
(p-tolyl)-5,6,7,8-tetrahydro-1,6-naphthyridin-3-yl)
acetic acid ¹H NMR (500 MHz, DMSO-d₆) δ ppm 7.35 (d, J=7.93 Hz, 1H), 7.30 (d, J=7.63 Hz, 1H), 7.19-7.28 (m, 3H), 7.09-7.18 (m, 4H), 4.76 (s, 1H), 3.20 (d, J=15.56 Hz, 1H), 2.83-2.94 (m, 3H), 2.79 (td, J=5.15, 10.76 Hz, 1H), 2.56-2.64 (m, 1H), 2.54 (br. s., 2H), 2.48 (s, 3H), 2.39 (s, 3H), 2.32 (t, J=6.71 Hz, 2H), 1.63 (quin, J=7.32 Hz, 2H), 0.87 (s, 9H). LCMS (M+H) calcd for $C_{31}H_{39}N_2O_3$: 487.29. found: 487.1.

Examples 30

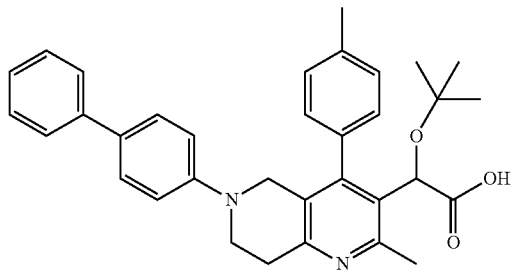 [SMILES: Cc1ccc(-c2c3c(nc(C)c2C(OC(C)(C)C)C(=O)O)CCN(c2ccc(-c4ccccc4)cc2)C3)cc1]

2-(6-([1,1'-Biphenyl]-4-yl)-2-methyl-4-(p-tolyl)-5,6,7,8-tetrahydro-1,6-naphthyridin-3-yl)-2-(tert-butoxy)acetic acid $^1$H NMR (500 MHz, DMSO-$d_6$) δ ppm 7.53 (d, J=7.63 Hz, 2H), 7.46 (t, J=7.63 Hz, 2H), 7.33-7.43 (m, 3H), 7.22-7.33 (m, 3H), 7.01 (d, J=7.63 Hz, 1H), 6.92 (s, 1H), 6.77 (dd, J=2.14, 8.24 Hz, 1H), 4.85 (s, 1H), 4.15 (d, J=16.17 Hz, 1H), 3.78-3.86 (m, 1H), 3.75 (d, J=16.48 Hz, 1H), 3.66 (td, J=6.48, 13.28 Hz, 1H), 2.93-3.03 (m, 2H), 2.47-2.50 (m, 3H), 2.43 (s, 3H), 0.90 (s, 9H). LCMS (M+H) calcd for $C_{34}H_{36}N_2O_3$: 521.28. found: 521.1.

Example 31

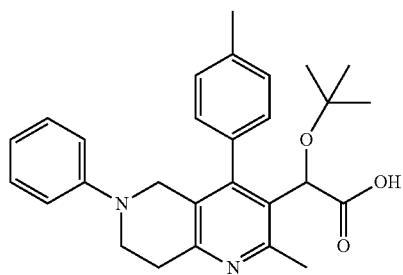 [SMILES: Cc1ccc(-c2c3c(nc(C)c2C(OC(C)(C)C)C(=O)O)CCN(c2ccccc2)C3)cc1]

2-(tert-Butoxy)-2-(2-methyl-6-phenyl-4-(p-tolyl)-5,6,7,8-tetrahydro-1,6-naphthyridin-3-yl)acetic acid $^1$H NMR (500 MHz, DMSO-$d_6$) δ ppm 7.38 (dd, J=7.63, 14.95 Hz, 2H), 7.29 (d, J=7.63 Hz, 1H), 7.24 (d, J=7.63 Hz, 1H), 7.17 (t, J=7.93 Hz, 2H), 6.66-6.82 (m, 3H), 4.80 (s, 1H), 4.07 (d, J=16.17 Hz, 1H), 3.63-3.73 (m, 2H), 3.55 (td, J=6.33, 12.97 Hz, 1H), 2.96 (br. s., 2H), 2.50 (s, 3H), 2.43 (s, 3H), 0.89 (s, 9H). LCMS (M+H) calcd for $C_{28}H_{33}N_2O_3$: 445.24. found: 445.2.

Example 32

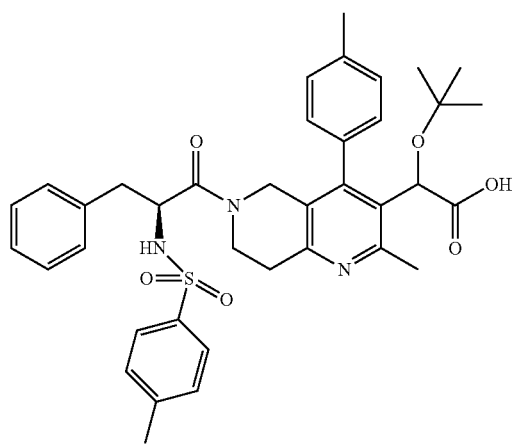 [SMILES: Cc1ccc(-c2c3c(nc(C)c2C(OC(C)(C)C)C(=O)O)CCN(C(=O)[C@H](Cc2ccccc2)NS(=O)(=O)c2ccc(C)cc2)C3)cc1]

2-(tert-Butoxy)-2-(2-methyl-6-(2-(4-methylphenylsulfonamido)-3-phenylpropanoyl)-4-(p-tolyl)-5,6,7,8-tetrahydro-1,6-naphthyridin-3-yl)acetic acid $^1$H NMR (500 MHz, DMSO-d6) δ ppm 6.86-7.55 (m, 13H), 6.72 (d, J=7.02 Hz, 1H), 4.77 (br. s., 1H), 4.43 (t, J=7.17 Hz, 0.5H), 3.90-4.00 (m, 0.5H), 3.72-3.89 (m, 1H), 3.48-3.68 (m, 2H), 3.15-3.26 (m, 1H), 2.59-2.87 (m, 2H), 2.36-2.48 (m, 5H), 2.35 (s, 3H), 2.22 (s, 3H), 0.81-0.98 (m, 9H). LCMS (M+H) calcd for C38H44N3O6S: 670.29. found: 670.3.

Example 33

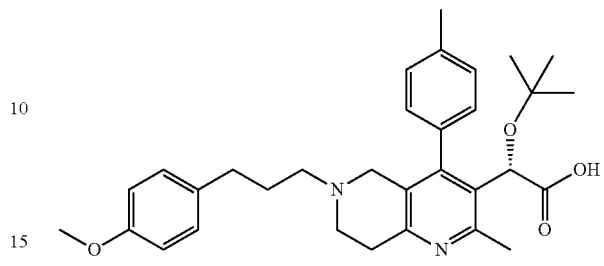

(S)-2-(tert-Butoxy)-2-(6-(3-(4-methoxyphenyl)propyl)-2-methyl-4-(p-tolyl)-5,6,7,8-tetrahydro-1,6-naphthyridin-3-yl)acetic acid $^1$H NMR (500 MHz, DMSO-$d_6$) δ 7.47-7.26 (m), 7.20 (d, J=7.3 Hz), 7.13 (d, J=7.6 Hz), 7.03 (d, J=8.5Hz), 6.81 (d, J=8.5Hz), 4.77 (s), 3.72 (s), 3.17 (s), 3.21 (s), 3.02-2.82 (m), 2.77 (m), 2.51-2.43 (m), 2.40 (s), 2.30 (t, J=6.6 Hz), 1.92, 1.63-1.44 (m), 0.88 (s).

Example 34

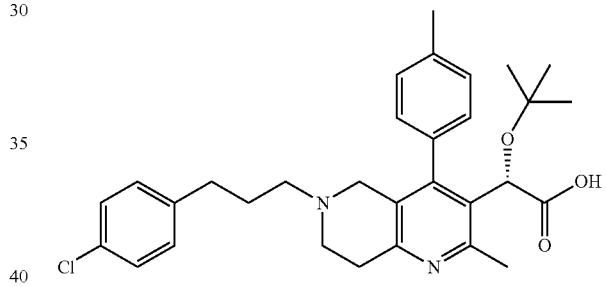

(S)-2-(tert-Butoxy)-2-(6-(3-(4-chlorophenyl)propyl)-2-methyl-4-(p-tolyl)-5,6,7,8-tetrahydro-1,6-naphthyridin-3-yl)acetic acid $^1$H NMR (500 MHz, DMSO-d6) δδ 7.37-7.28 (m), 7.23-7.11 (m), 4.77 (s), 3.18 (m), 3.21 (m), 2.92-2.83 (m), 2.54 (m), 2.48 (s), 2.40 (s), 2.30 (t, J=7.2 Hz), 1.62 (m), 0.88 (s).

Example 35

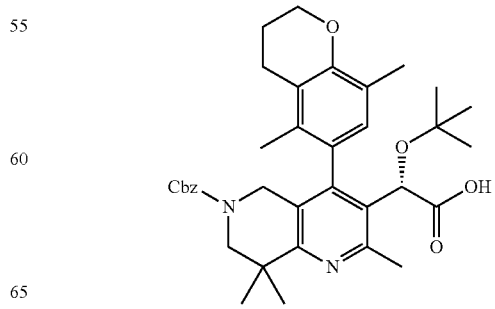

(2S)-2-(6-((Benzyloxy)carbonyl)-4-(8-fluoro-5-methylchroman-6-yl)-2,8,8-trimethyl-5,6,7,8-tetrahydro-1,6-naphthyridin-3-yl)-2-(tert-butoxy)acetic acid ¹H NMR (400 MHz, CDCl₃) δ 7.43-7.30 (m, 5H), 6.67 (d, J=11.0 Hz, 1H), 5.20-5.08 (m, 2H), 5.01 (s, 1H), 4.29 (br. s., 2H), 4.22-3.96 (m, 2H), 3.55-3.48 (m, 2H), 2.69 (br. s., 1H), 2.64 (s, 3H), 2.18-2.06 (m, 3H), 1.90 (br. s., 2H), 1.80 (br. s., 1H), 1.34 (br. s., 6H), 1.17 (s, 9H). LCMS (M+H)=605.4.

Example 36

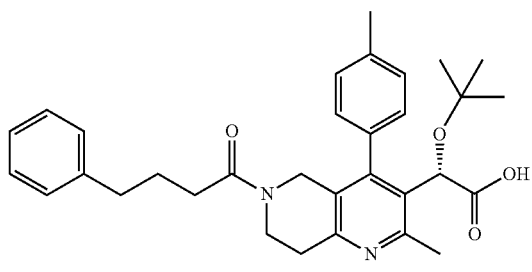 [SMILES: Cc1ccc(-c2c3c(nc(C)c2[C@H](OC(C)(C)C)C(=O)O)CCN(C(=O)CCCc2ccccc2)C3)cc1]

(S)-2-(tert-Butoxy)-2-(2-methyl-6-(4-phenylbutanoyl)-4-(p-tolyl)-5,6,7,8-tetrahydro-1,6-naphthyridin-3-yl)acetic acid ¹H NMR (500 MHz, DMSO-d6) δ 7.35 (d, J=7.9 Hz), 7.38 (d, J=7.6 Hz), 7.30-7.15 (m), 7.08 (m), 4.82-4.78 (m), 4.18-4.13 (m), 3.80-3.60 (m) 2.91 (m), 2.58 (t, J=7.8 Hz), 2.53-2.47 (m), 2.45-2.30 (m), 2.20 (m) 1.81-1.63 (m), 1.3 (m) 0.91 (s)-0.84 (s).

Example 37

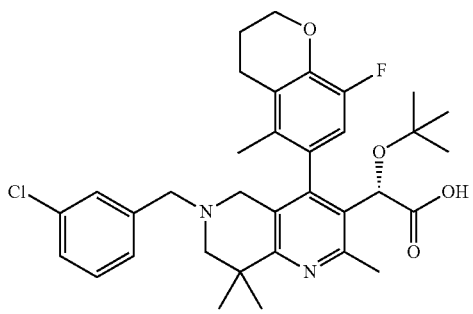 [SMILES: Cc1nc2c(c(-c3cc(F)c4c(c3C)CCCO4)c1[C@H](OC(C)(C)C)C(=O)O)CN(Cc1cccc(Cl)c1)CC2(C)C]

(2S)-2-(tert-Butoxy)-2-(6-(3-chlorobenzyl)-4-(8-fluoro-5-methylchroman-6-yl)-2,8,8-trimethyl-5,6,7,8-tetrahydro-1,6-naphthyridin-3-yl)acetic acid ¹H NMR (400 MHz, CHLOROFORM-d) δ 7.31 (s, 1H), 7.25-7.17 (m, 3H), 6.65 (d, J=11.3 Hz, 1H), 5.00 (s, 1H), 4.28 (t, J=5.3 Hz, 2H), 3.60 (d, J=13.6 Hz, 1H), 3.37 (d, J=13.6 Hz, 1H), 3.03 (d, J=15.3 Hz, 1H), 2.91 (d, J=15.3 Hz, 1H), 2.73-2.54 (m, 6H), 2.18-2.06 (m, 3H), 1.80 (s, 3H), 1.37 (s, 3H), 1.32 (s, 3H), 1.16 (s, 9H). LCMS (M+H)=595.3.

Example 38

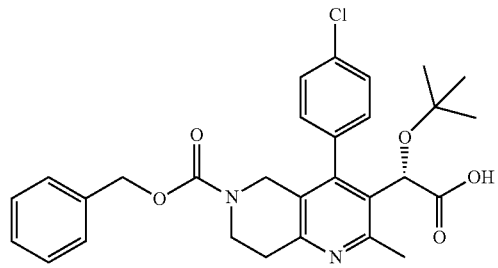 [SMILES: Cc1nc2c(c(-c3ccc(Cl)cc3)c1[C@H](OC(C)(C)C)C(=O)O)CN(C(=O)OCc1ccccc1)CC2]

(S)-2-(6-((Benzyloxy)carbonyl)-4-(4-chlorophenyl)-2-methyl-5,6,7,8-tetrahydro-1,6-naphthyridin-3-yl)-2-(tert-butoxy)acetic acid ¹H NMR (500 MHz, DMSO-d6) δ: 7.51-7.72 (m, 2H), 7.27-7.44 (m, 6H), 7.17 (br. s., 1H), 4.97-5.13 (m, 2H), 4.71 (br. s., 1H), 4.14-4.33 (m, 1H), 3.92-4.05 (m, 1H), 3.57-3.85 (m, 2H), 2.91 (t, J=5.95 Hz, 2H), 2.52, (s, 3 under solvent peak), 0.90 (s, 9H). LCMS (M+H) calcd for C29H32ClN2O5: 523.2. found: 523.1.

Example 39

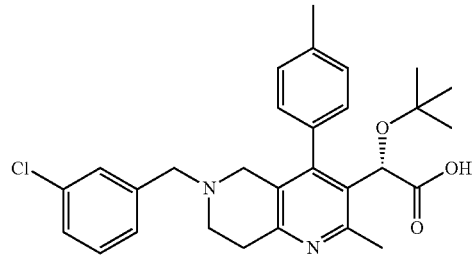 [SMILES: Cc1ccc(-c2c3c(nc(C)c2[C@H](OC(C)(C)C)C(=O)O)CCN(Cc2cccc(Cl)c2)C3)cc1]

(S)-2-(tert-Butoxy)-2-(6-(3-chlorobenzyl)-2-methyl-4-(p-tolyl)-5,6,7,8-tetrahydro-1,6-naphthyridin-3-yl)acetic acid ¹H NMR (MeOD) δ: 7.24-7.32 (m, 4H), 7.14-7.23 (m, 3H), 7.08 (dd, J=7.8, 1.7 Hz, 1H), 4.92 (s, 1H), 3.68-3.80 (m, 2H), 3.50-3.56 (m, 2H), 3.02-3.17 (m, 4H), 2.63 (s, 3H), 2.44 (s, 3H), 0.95 (s, 9H).

Example 40

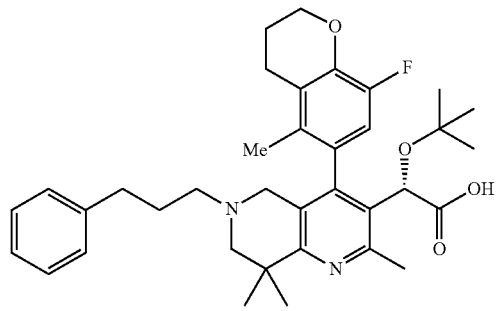 [SMILES: Cc1nc2c(c(-c3cc(F)c4c(c3C)CCCO4)c1[C@H](OC(C)(C)C)C(=O)O)CN(CCCc1ccccc1)CC2(C)C]

(2S)-2-(tert-Butoxy)-2-(4-(8-fluoro-5-methylchroman-6-yl)-2,8,8-trimethyl-6-(3-phenylpropyl)-5,6,7,8-tetrahydro-1,6-naphthyridin-3-yl)acetic acid ¹H NMR (500 MHz, CHLOROFORM-d) δ 7.31-7.24 (m, 2H), 7.23-7.15 (m, 3H), 6.69 (d, J=11.5Hz, 1H), 4.98 (br. s., 1H), 4.32-4.27 (m, 2H), 3.09 (d, J=15.4 Hz, 1H), 2.86 (d, J=15.3 Hz, 1H), 2.74-2.64 (m, 4H), 2.63 (s, 3H), 2.54-2.48 (m, 1H), 2.45-2.30 (m, 2H), 2.18-2.11 (m, 3H), 1.88 (s, 3H) 1.84-1.74 (m, 2H), 1.39 (d, J=6.5Hz, 6H), 1.16 (s, 9H). LCMS (M+H)=589.5.

Example 41

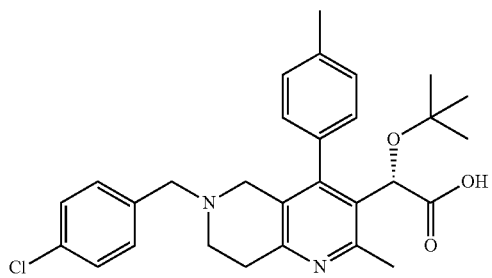 [SMILES: Cc1ccc(-c2c3c(nc(C)c2[C@H](OC(C)(C)C)C(=O)O)CCN(Cc2ccc(Cl)cc2)C3)cc1]

(S)-2-(tert-Butoxy)-2-(6-(4-chlorobenzyl)-2-methyl-4-(p-tolyl)-5,6,7,8-tetrahydro-1,6-naphthyridin-3-yl)acetic acid ¹H NMR (MeOD) δ: 7.24-7.31 (m, 1H), 7.14 (s, 1H), 7.07 (d, J=7.7 Hz, 1H), 3.71-3.88 (m, 2H), 3.55 (d, J=15.4 Hz, 1H), 3.02-3.24 (m, 4H), 2.93-3.01 (m, 1H), 2.62 (s, 3H), 2.46 (s, 3H), 0.93-0.97 (m, 9H).

Example 42

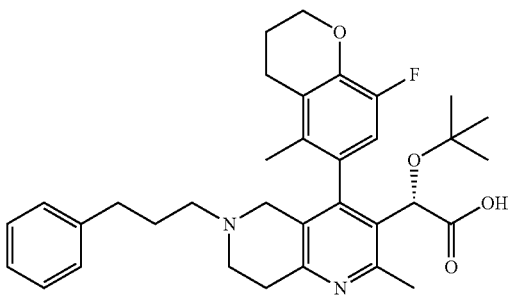

(2S)-2-(tert-Butoxy)-2-((R)-4-(8-fluoro-5-methylchroman-6-yl)-2-methyl-6-(3-phenylpropyl)-5,6,7,8-tetrahydro-1,6-naphthyridin-3-yl)acetic acid ¹H NMR (500 MHz, DMSO-d₆) δ 7.28-7.24 (m, J=7.6 Hz, 2H), 7.19-7.13 (m, J=8.2 Hz, 3H), 6.71 (d, J=11.0 Hz, 1H), 4.20 (t, J=5.2 Hz, 2H), 2.93-2.86 (m, J=5.5Hz, 3H), 2.73-2.64 (m, J=3.7, 1.6, 1.6 Hz, 4H), 2.58-2.53 (m, 2H), 2.43-2.40 (m, 2H), 2.39-2.32 (m, 4H), 2.02 (dd, J=6.7, 4.6 Hz, 2H), 1.79 (s, 3H), 1.70-1.63 (m, J=6.4 Hz, 2H); LCMS (ESI, M+1): 561.5.

Example 43

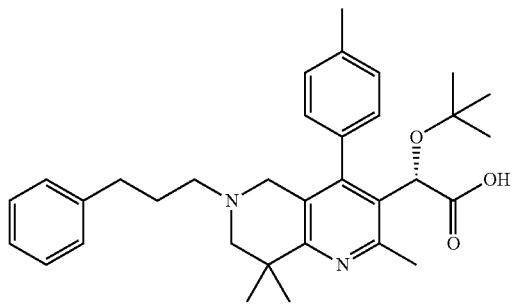 [SMILES: Cc1ccc(-c2c3c(nc(C)c2[C@H](OC(C)(C)C)C(=O)O)C(C)(C)CN(CCCc2ccccc2)C3)cc1]

(S)-2-(tert-Butoxy)-2-(2,8,8-trimethyl-6-(3-phenylpropyl)-4-(p-tolyl)-5,6,7,8-tetrahydro-1,6-naphthyridin-3-yl)acetic acid ¹H NMR (500 MHz, DMSO-d₆) δ 7.35 (d, J=7.6 Hz, 1H), 7.30 (d, J=7.6 Hz, 1H), 7.28-7.23 (m, 2H), 7.21-7.17 (m, 1H), 7.16-7.10 (m, 4H), 4.77 (s, 1H), 3.17 (d, J=15.3 Hz, 1H), 2.88 (d, J=15.3 Hz, 1H), 2.61-2.53 (m, 3H), 2.39 (s, 3H), 2.35 (d, J=11.3 Hz, 1H), 2.27 (t, J=6.7 Hz, 2H), 1.64 (t, J=7.2 Hz, 2H), 1.30 (s, 3H), 1.33 (s, 3H), 0.88 (s, 9H). LCMS (M+H)=515.5.

Example 44

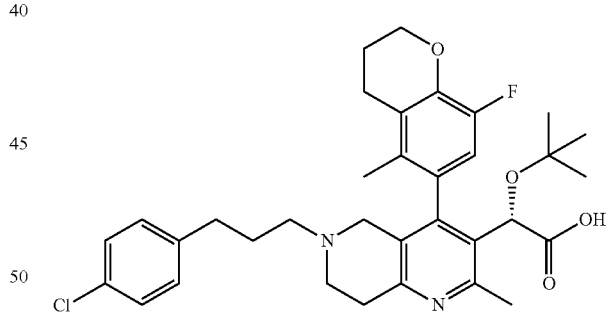

(2S)-2-(tert-Butoxy)-2-(6-(3-(4-chlorophenyl)propyl)-(R)-4-(8-fluoro-5-methylchroman-6-yl)-2-methyl-5,6,7,8-tetrahydro-1,6-naphthyridin-3-yl)acetic acid ¹H NMR (500 MHz, DMSO-d₆) δ 7.96-7.92 (m, 1H), 7.27 (d, J=7.9 Hz, 2H), 7.15 (d, J=8.2 Hz, 2H), 6.65 (d, J=11.3 Hz, 1H), 4.69 (s, 1H), 4.18 (t, J=4.6 Hz, 2H), 2.96 (d, J=15.3 Hz, 1H), 2.88-2.77 (m, 3H), 2.70-2.58 (m, 4H), 2.53 (s, 3H), 2.28 (t, J=6.6 Hz, 2H), 2.00 (d, J=5.2 Hz, 2H), 1.72 (s, 3H), 1.66-1.58 (m, 2H), 0.99 (s, 9H); LCMS (ESI, M+1): 595.6.

Example 45

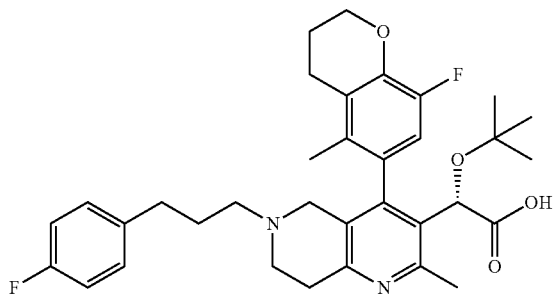 [SMILES: Cc1nc2c(c(-c3cc(F)c4c(c3C)CCCO4)c1[C@H](OC(C)(C)C)C(=O)O)CN(CCCc1ccc(F)cc1)CC2]

(S)-2-(tert-Butoxy)-2-((R)-4-(8-fluoro-5-methylchroman-6-yl)-6-(3-(4-fluorophenyl)propyl)-2-methyl-5,6,7,8-tetrahydro-1,6-naphthyridin-3-yl)acetic acid $^1$H NMR (500 MHz, DMSO-d$_6$) δ 7.20-7.15 (m, J=8.5, 5.8 Hz, 2H), 7.09-7.04 (m, 2H), 6.69 (d, J=11.3 Hz, 1H), 4.72 (s, 1H), 4.21 (t, J=5.2 Hz, 2H), 2.98 (d, J=15.0 Hz, 1H), 2.90-2.85 (m, 2H), 2.82 (d, J=15.3 Hz, 1H), 2.72-2.63 (m, 4H), 2.56-2.53 (m, 4H), 2.31 (t, J=7.0 Hz, 2H), 2.06-1.99 (m, J=5.2 Hz, 2H), 1.75 (s, 3H), 1.64 (quin, J=7.4 Hz, 2H), 1.02 (s, 9H); LCMS (ESI, M+1): 579.4.

Example 46

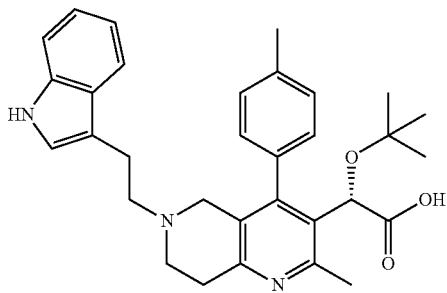 [SMILES: Cc1ccc(-c2c3c(nc(C)c2[C@H](OC(C)(C)C)C(=O)O)CCN(CCc2c[nH]c4ccccc24)C3)cc1]

(S)-2-(6-(2-(1H-Indol-3-yl)ethyl)-2-methyl-4-(p-tolyl)-5,6,7,8-tetrahydro-1,6-naphthyridin-3-yl)-2-(tert-butoxy)acetic acid $^1$H NMR (500 MHz, DMSO-d$_6$) δ 10.74 (s, 1H), 7.39 (d, J=7.9 Hz, 1H), 7.35 (d, J=7.6 Hz, 1H), 7.31 (d, J=7.9 Hz, 2H), 7.20 (d, J=7.3 Hz, 1H), 7.14 (d, J=7.6 Hz, 1H), 7.09 (d, J=2.1 Hz, 1H), 7.04 (t, J=7.2 Hz, 1H), 6.98-6.87 (m, 1H), 4.79 (s, 1H), 3.31 (br. s., 1H), 3.02 (d, J=15.3 Hz, 1H), 2.96-2.85 (m, 3H), 2.83-2.68 (m, 3H), 2.67-2.59 (m, 2H), 2.49 (s, 3H), 2.40 (s, 3H), 0.88 (s, 9H). LCMS (M+H) calcd for C$_{32}$H$_{38}$N$_3$O$_3$: 512.29. found 512.2.

Example 47

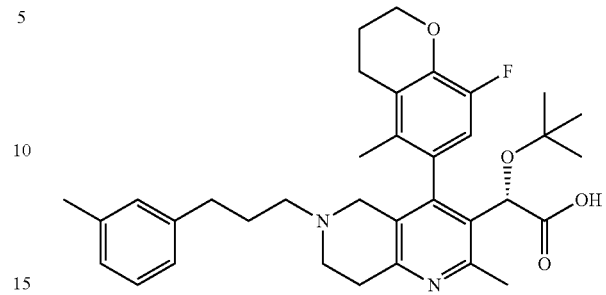

(2S)-2-(tert-Butoxy)-2-((R)-4-(8-fluoro-5-methyl-chroman-6-yl)-2-methyl-6-(3-(m-tolyl) propyl)-5,6,7,8-tetrahydro-1,6-naphthyridin-3-yl)acetic acid $^1$H NMR (500 MHz, DMSO-d$_6$) δ 6.86 (t, J=7.5Hz, 1H), 6.73-6.66 (m, 2H), 6.63 (d, J=7.3 Hz, 1H), 6.39 (d, J=11.3 Hz, 1H), 4.43 (s, 1H), 3.92 (br. s., 2H), 2.72 (d, J=15.0 Hz, 1H), 2.64-2.54 (m, 3H), 2.42 (br. s., 2H), 2.37 (br. s., 2H), 2.30-2.27 (m, 3H), 2.25 (br. s., 3H), 2.24-2.20 (m, 2H), 2.04 (t, J=6.7 Hz, 2H), 1.98 (s, 3H), 1.74 (d, J=5.2 Hz, 2H), 1.48 (s, 3H), 1.39-1.32 (m, J=6.9, 6.9 Hz, 2H), 0.74 (s, 9H); LCMS (ESI, M+1): 575.6.

Example 48

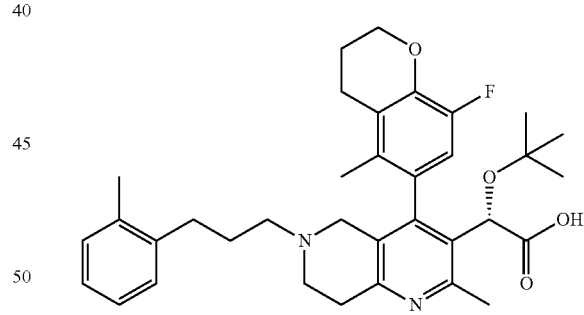

(2S)-2-(tert-Butoxy)-2-((R)-4-(8-fluoro-5-methyl-chroman-6-yl)-2-methyl-6-(3-(o-tolyl) propyl)-5,6,7,8-tetrahydro-1,6-naphthyridin-3-yl)acetic acid $^1$H NMR (500 MHz, DMSO-d$_6$) δ 6.87-6.76 (m, 4H), 6.40 (d, J=11.3 Hz, 1H), 4.42 (s, 1H), 3.94 (br. s., 2H), 2.74 (d, J=15.6 Hz, 1H), 2.64 (s, 1H), 2.63-2.54 (m, 3H), 2.48 (s, 1H), 2.46-2.33 (m, 3H), 2.10 (t, J=6.6 Hz, 2H), 1.94 (s, 3H), 1.76 (d, J=4.6 Hz, 2H), 1.50 (s, 3H), 1.36-1.28 (m, J=6.7 Hz, 2H), 0.75 (s, 9H); LCMS (ESI, M+1): 575.6.

Example 49

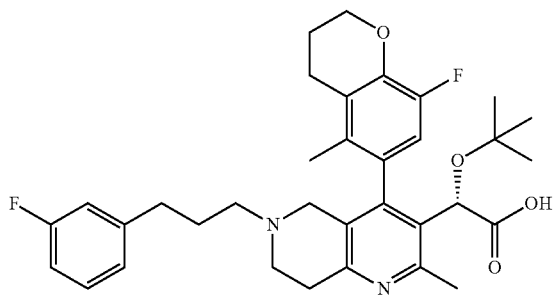 [SMILES: Cc1nc2c(c(-c3cc(F)c4c(c3C)CCCO4)c1[C@H](OC(C)(C)C)C(=O)O)CN(CCCc1cccc(F)c1)CC2]

(S)-2-(tert-Butoxy)-2-((R)-4-(8-fluoro-5-methylchroman-6-yl)-6-(3-(3-fluorophenyl)propyl)-2-methyl-5,6,7,8-tetrahydro-1,6-naphthyridin-3-yl)acetic acid $^1$H NMR (500 MHz, DMSO-d$_6$) δ 7.28 (dd, J=7.9, 7.0 Hz, 1H), 6.97 (d, J=11.0 Hz, 3H), 6.66 (d, J=11.9 Hz, 1H), 4.69 (s, 1H), 4.19 (t, J=4.9 Hz, 3H), 2.96 (d, J=15.9 Hz, 2H), 2.89-2.80 (m, 4H), 2.65 (dd, J=18.9, 11.3 Hz, 3H), 2.58-2.53 (m, 6H), 2.30 (t, J=6.7 Hz, 2H), 2.01 (d, J=5.5Hz, 2H), 1.74 (s, 3H), 1.69-1.60 (m, 2H), 1.00 (s, 9H); LCMS (ESI, M+1): 579.6.

Example 50

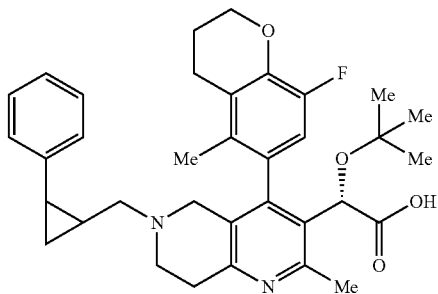 [SMILES: Cc1nc2c(c(-c3cc(F)c4c(c3C)CCCO4)c1[C@H](OC(C)(C)C)C(=O)O)CN(CC1CC1c1ccccc1)CC2]

(2S)-2-(tert-Butoxy)-2-((R)-4-(8-fluoro-5-methylchroman-6-yl)-2-methyl-6-((2-phenylcyclopropyl)methyl)-5,6,7,8-tetrahydro-1,6-naphthyridin-3-yl) acetic acid 1:1 diastereomeric mixture. LCMS (ESI, M+1): 573.6.

Example 51

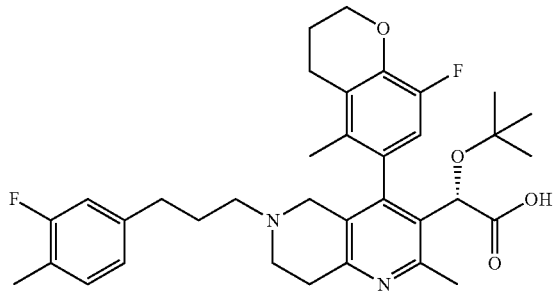 [SMILES: Cc1ccc(CCCN2CCc3nc(C)c([C@H](OC(C)(C)C)C(=O)O)c(-c4cc(F)c5c(c4C)CCCO5)c3C2)cc1F]

Example 52

(2S)-2-(tert-Butoxy)-2-(6-(3-(3-fluoro-4-methylphenyl)propyl)-(R)-4-(8-fluoro-5-methyl-3,4,4a,5-tetrahydro-2H-chromen-6-yl)-2-methyl-5,6,7,8-tetrahydro-1,6-naphthyridin-3-yl)acetic acid $^1$H NMR (500 MHz, DMSO-d$_6$) δ 7.96 (s, 1H), 7.03 (d, J=7.6 Hz, 1H), 6.97 (d, J=9.2 Hz, 2H), 6.66 (d, J=11.3 Hz, 1H), 4.68 (s, 1H), 4.20 (t, J=4.9 Hz, 2H), 2.98 (d, J=15.3 Hz, 1H), 2.89-2.79 (m, 3H), 2.72-2.60 (m, 4H), 2.54 (s, 3H), 2.30 (t, J=6.7 Hz, 2H), 2.18 (s, 3H), 2.06-1.97 (m, J=5.2 Hz, 2H), 1.75 (s, 3H), 1.62 (quin, J=7.1 Hz, 2H), 1.01 (s, 9H); LCMS (ESI, M+1): 593.6.

Example 52

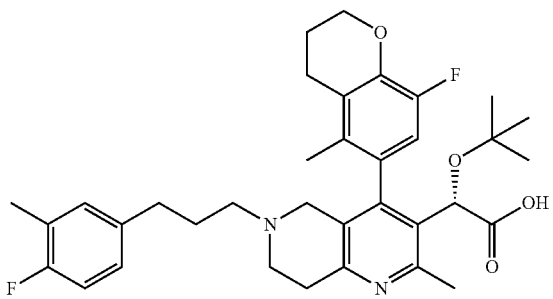 [SMILES: Cc1cc(CCCN2CCc3nc(C)c([C@H](OC(C)(C)C)C(=O)O)c(-c4cc(F)c5c(c4C)CCCO5)c3C2)ccc1F]

(2S)-2-(tert-Butoxy)-2-(6-(3-(4-fluoro-3-methylphenyl)propyl)-(R)-4-(8-fluoro-5-methylchroman-6-yl)-2-methyl-5,6,7,8-tetrahydro-1,6-naphthyridin-3-yl) acetic acid $^1$H NMR (500 MHz, DMSO-d$_6$) δ 7.98-7.90 (m, 1H), 7.12 (t, J=8.1 Hz, 1H), 6.88 (d, J=11.3 Hz, 1H), 6.84 (d, J=7.9 Hz, 1H), 6.64 (d, J=11.3 Hz, 1H), 4.67 (s, 1H), 4.18 (t, J=4.9 Hz, 2H), 2.97-2.92 (m, 1H), 2.85 (d, J=4.3 Hz, 2H), 2.83-2.78 (m, 1H), 2.69-2.59 (m, 4H), 2.53 (s, 3H), 2.27 (t, J=6.6 Hz, 2H), 2.16 (s, 3H), 2.00 (d, J=5.2 Hz, 2H), 1.73 (s, 3H), 1.61 (quin, J=6.9 Hz, 2H), 0.99 (s, 9H); LCMS (ESI, M+1): 593.6.

Example 53

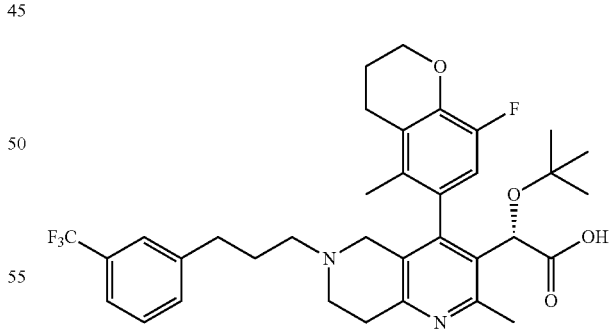

(2S)-2-(tert-Butoxy)-2-((R)-4-(8-fluoro-5-methyl-3,4,4a,5-tetrahydro-2H-chromen-6-yl)-2-methyl-6-(3-(3-(trifluoromethyl)phenyl)propyl)-5,6,7,8-tetrahydro-1,6-naphthyridin-3-yl)acetic acid $^1$H NMR (500 MHz, DMSO-d$_6$) δ 7.96-7.92 (m, 1H), 7.55-7.42 (m, 4H), 6.64 (d, J=11.0 Hz, 1H), 4.69 (s, 1H), 4.18 (t, J=4.6 Hz, 2H), 2.97 (d, J=15.3 Hz, 1H), 2.88-2.78 (m, 3H), 2.71-2.58 (m, 6H), 2.30 (t, J=6.7 Hz, 2H), 1.99 (dd, J=5.8, 4.9 Hz, 2H), 1.72 (s, 3H), 1.66 (t, J=7.0 Hz, 2H), 0.99 (s, 9H); LCMS (ESI, M+1): 629.6.

Example 54

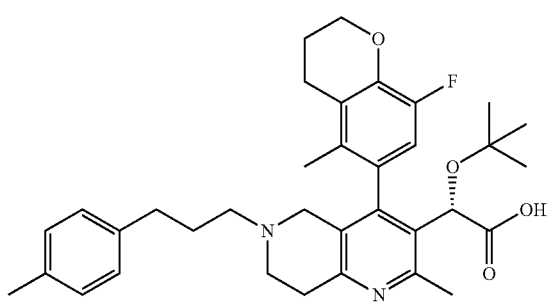 [SMILES: Cc1ccc(CCCN2CCc3nc(C)c([C@H](OC(C)(C)C)C(=O)O)c(-c4cc(F)c5c(c4C)CCCO5)c3C2)cc1]

(2S)-2-(tert-Butoxy)-2-(4-(8-fluoro-5-methylchroman-6-yl)-2-methyl-6-(3-(p-tolyl) propyl)-5,6,7,8-tetrahydro-1,6-naphthyridin-3-yl)acetic acid $^1$H NMR (500 MHz, DMSO-d$_6$) δ 7.96 (s, 1H), 7.06-7.02 (m, 2H), 7.02-6.98 (m, 2H), 6.66 (d, J=11.3 Hz, 1H), 4.69 (s, 1H), 4.20 (t, J=5.0 Hz, 2H), 2.96 (d, J=15.3 Hz, 1H), 2.89-2.79 (m, 3H), 2.70-2.61 (m, 4H), 2.54 (s, 3H), 2.49-2.45 (m, 2H), 2.29 (t, J=6.7 Hz, 2H), 2.25 (s, 3H), 2.02 (q, J=5.5Hz, 2H), 1.75 (s, 3H), 1.61 (quin, J=7.1 Hz, 2H), 1.01 (s, 9H); LCMS (ESI, M+1): 575.6.

Example 55

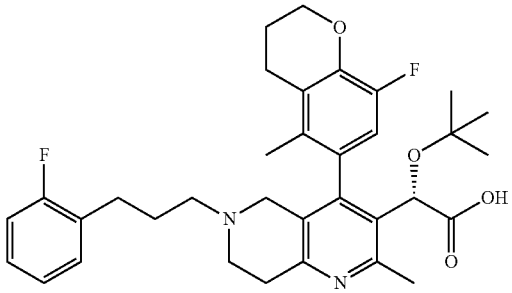

(2S)-2-(tert-Butoxy)-2-((R)-4-(8-fluoro-5-methylchroman-6-yl)-6-(3-(2-fluorophenyl)propyl)-2-methyl-5,6,7,8-tetrahydro-1,6-naphthyridin-3-yl)acetic acid $^1$H NMR (500 MHz, DMSO-d$_6$) δ 7.96 (s, 1H), 7.28 (dd, J=9.2, 7.3 Hz, 1H), 7.01-6.93 (m, 3H), 6.66 (d, J=11.3 Hz, 1H), 4.69 (s, 1H), 4.19 (t, J=4.9 Hz, 2H), 2.97 (d, J=15.3 Hz, 1H), 2.88-2.79 (m, 3H), 2.68 (t, J=5.6 Hz, 2H), 2.66-2.61 (m, 2H), 2.59-2.53 (m, 5H), 2.30 (t, J=6.6 Hz, 2H), 2.01 (d, J=4.9 Hz, 2H), 1.75 (s, 3H), 1.65 (quin, J=7.2 Hz, 2H), 1.01 (s, 9H); LCMS (ESI, M+1): 579.6.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of Formula I

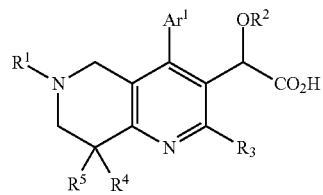

where:

R$^1$ is hydrogen, alkyl, cycloalkyl, haloalkyl, (Ar$^2$)alkyl, (Ar$^2$)cycloalkyl, Ar$^2$, alkylCO, cycloalkylCO, haloalkylCO, (Ar$^2$)alkylCO, ((Ar$^2$)cycloalkyl)alkylCO, (Ar$^2$)cycloalkylCO, Ar$^2$CO, (Ar$^2$)alkylCOCO, Ar$^2$COCO, alkylCO$_2$, haloalkylCO$_2$, (Ar$^2$)alkylCO$_2$, Ar$^2$CO$_2$, alkylCONH, haloalkylCONH, (Ar$^2$)alkylCONH, Ar$^2$CONH, alkylSO$_2$, cycloalkylSO$_2$, haloalkylSO$_2$, and Ar$^2$SO$_2$;

or R$^1$ is (PhCH$_2$O)PhCH$_2$CO,

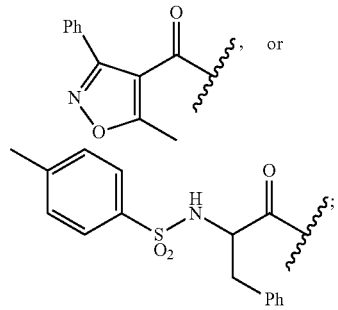

R$^2$ is alkyl or haloalkyl;
R$^3$ is alkyl;
R$^4$ is hydrogen or alkyl;
R$^5$ is hydrogen or alkyl;
Ar$^1$ is phenyl or chromanyl, and is substituted with 0-3 substituents selected from halo, alkyl, haloalkyl, alkoxy, and haloalkoxy; and
Ar$^2$ is phenyl, biphenyl, or indolyl, and is substituted with 0-3 substituents selected from halo, alkyl, haloalkyl, cycloalkyl, halocycloalkyl, alkoxy, and haloalkoxy;
or a pharmaceutically acceptable salt thereof.

2. A compound of claim 1 where:
R$^1$ is hydrogen, alkyl, cycloalkyl, haloalkyl, (Ar$^2$)alkyl, (Ar$^2$)cycloalkyl, Ar$^2$, alkylCO, cycloalkylCO, haloalkylCO, (Ar$^2$)alkylCO, (Ar$^2$)cycloalkylCO, Ar$^2$CO, (Ar$^2$)alkylCOCO, Ar$^2$COCO, alkylCO$_2$, haloalkylCO$_2$, (Ar$^2$)alkylCO$_2$, Ar$^2$CO$_2$, alkylCONH, haloalkylCONH, (Ar$^2$)alkylCONH, Ar$^2$CONH, alkylSO$_2$, cycloalkylSO$_2$, haloalkylSO$_2$, and Ar$^2$SO$_2$;

or R¹ is (PhCH₂O)PhCH₂CO,

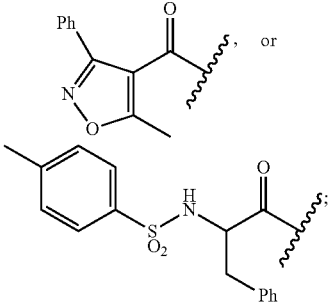

R² is alkyl or haloalkyl;
R³ is alkyl;
R⁴ is hydrogen or alkyl;
R⁵ is hydrogen or alkyl;
Ar¹ is phenyl or chromanyl, and is substituted with 0-3 substituents selected from halo, alkyl, haloalkyl, alkoxy, and haloalkoxy; and
Ar² is phenyl, biphenyl, or indolyl, and is substituted with 0-3 substituents selected from halo, alkyl, haloalkyl, cycloalkyl, and halocycloalkyl;
or a pharmaceutically acceptable salt thereof.

3. A compound of claim 1 where:
R¹ is hydrogen, (Ar²)alkyl, Ar², alkylCO, (Ar²)alkylCO, (Ar²)cycloalkylCO, Ar²CO, Ar²COCO, alkylO₂C, ((Ar²)alkoxyCO, (Ar²)alkylNHCO, and alkylSO₂;
or R¹ is (PhCH₂O)PhCH₂CO,

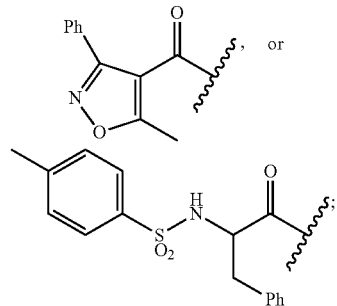

R² is alkyl;
R³ is alkyl;
R⁴ is hydrogen or alkyl;
R⁵ is hydrogen or alkyl;
Ar¹ is phenyl or chromanyl, and is substituted with 0-3 substituents selected from halo, alkyl, haloalkyl, alkoxy, and haloalkoxy; and
Ar² is phenyl, biphenyl, or indolyl, and is substituted with 0-3 substituents selected from halo, alkyl, haloalkyl, cycloalkyl, and halocycloalkyl;
or a pharmaceutically acceptable salt thereof.

4. A compound of claim 1 where:
R¹ is hydrogen, (Ar²)alkyl, Ar², alkylCO, (Ar²)alkylCO, (Ar²)cycloalkylCO, Ar²CO, Ar²COCO, alkylO₂C, ((Ar²)alkoxyCO, (Ar²)alkylNHCO, and alkylSO₂; R² is alkyl; R³ is alkyl; R⁴ is hydrogen or alkyl; R⁵ is hydrogen or alkyl; Ar¹ is phenyl substituted with 0-3 halo or alkyl substituents; and Ar² is phenyl, biphenyl, or indolyl, and is substituted with 0-3 halo substituents;
or a pharmaceutically acceptable salt thereof.

5. A compound of claim 1 where R¹ is hydrogen, (Ar²) alkyl, Ar², alkylCO, (Ar²)alkylCO, (Ar²)cycloalkylCO, Ar²CO, Ar²COCO, alkylO₂C, ((Ar²)alkoxyCO, (Ar²)alkyl-NHCO, and alkylSO₂.

6. A compound of claim 1 where R² is alkyl.

7. A compound of claim 1 where R³ is alkyl.

8. A compound of claim 1 where R⁴ is hydrogen or alkyl.

9. A compound of claim 1 where R⁵ is hydrogen or alkyl.

10. A compound of claim 1 where Ar¹ is phenyl substituted with 0-3 halo substituents.

11. A compound of claim 1 where Ar² is phenyl, biphenyl, or indolyl, and is substituted with 0-3 halo substituents.

12. A compound of claim 1 selected from the group consisting of
2-tert-Butoxy-2-(4-(4-fluorophenyl)-2-isopropyl-8,8-dimethyl-5,6,7,8-tetrahydro-1,6-naphthyridin-3-yl) acetic acid;
2-(6-Acetyl-4-(4-fluorophenyl)-2-isopropyl-8,8-dimethyl-5,6,7,8-tetrahydro-1,6-naphthyridin-3-yl)-2-tert-butoxyacetic acid;
2-(6-Benzoyl-4-(4-fluorophenyl)-2-isopropyl-8,8-dimethyl-5,6,7,8-tetrahydro-1,6-naphthyridin-3-yl)-2-tert-butoxyacetic acid;
2-tert-Butoxy-2-(6-(4-fluorobenzoyl)-4-(4-fluorophenyl)-2-isopropyl-8,8-dimethyl-5,6,7,8-tetrahydro-1,6-naphthyridin-3-yl)acetic acid;
2-(6-(2-(4-(Benzyloxy)phenyl)acetyl)-4-(4-fluorophenyl)-2-isopropyl-8,8-dimethyl-5,6,7,8-tetrahydro-1,6-naphthyridin-3-yl)-2-tert-butoxyacetic acid;
2-tert-Butoxy-2-(4-(4-fluorophenyl)-6-(2-((4-fluorophenyl)acetyl)-2-isopropyl-8,8-dimethyl-5,6,7,8-tetrahydro-1,6-naphthyridin-3-yl)acetic acid;
2-tert-Butoxy-2-(4-(4-fluorophenyl)-2-isopropyl-8,8-dimethyl-6-(2-phenylacetyl)-5,6,7,8-tetrahydro-1,6-naphthyridin-3-yl)acetic acid;
2-tert-Butoxy-2-O-(4-fluorophenyl)-2-isopropyl-8,8-dimethyl-6-((1R,2R)-2-phenylcyclopropanecarbonyl)-5,6,7,8-tetrahydro-1,6-naphthyridin-3-yl)acetic acid;
2-tert-Butoxy-2-(4-(4-fluorophenyl)-2-isopropyl-8,8-dimethyl-6-(4-phenylbutanoyl)-5,6,7,8-tetrahydro-1,6-naphthyridin-3-yl)acetic acid;
2-tert-Butoxy-2-(4-(4-fluorophenyl)-2-isopropyl-8,8-dimethyl-6-(2-((4-methylphenylsolfonamido)-3-phenylpropanoyl)-5,6,7,8-tetrahydro-1,6-naphthyridin-3-yl)acetic acid;
2-(6-(2-(1H-Indol-3-yl)-2-oxoacetyl)-4-(4-fluorophenyl)-2-isopropyl-8,8-dimethyl-5,6,7,8-tetrahydro-1,6-naphthyridin-3-yl)-2-tert-butoxyacetic acid;
2-tert-Butoxy-2-(4-(4-fluorophenyl)-2-isopropyl-8,8-dimethyl-6-(3-phenylpropanoyl)-5,6,7,8-tetrahydro-1,6-naphthyridin-3-yl)acetic acid;
2-(6-(Biphenylcarbonyl)-4-(4-fluorophenyl)-2-isopropyl-8,8-dimethyl-5,6,7,8-tetrahydro-1,6-naphthyridin-3-yl)-2-tert-butoxyacetic acid;
2-tert-Butoxy-2-(4-(4-fluorophenyl)-2-isopropyl-8,8-dimethyl-6-(5-methyl-3-phenylisoxazole-4-carbonyl)-5,6,7,8-tetrahydro-1,6-naphthyridin-3-yl)acetic acid;
2-tert-Butoxy-2-(4-(4-fluorophenyl)-2-isopropyl-8,8-dimethyl-6-phenyl-5,6,7,8-tetrahydro-1,6-naphthyridin-3-yl)acetic acid;
2-tert-Butoxy-2-(6-(4-fluorobenzyl)-4-(4-fluorophenyl)-2-isopropyl-8,8-dimethyl-5,6,7,8-tetrahydro-1,6-naphthyridin-3-yl)acetic acid;
2-(6-([1,1'-Biphenyl]-3-yl)-4-(4-fluorophenyl)-2-isopropyl-8,8-dimethyl-5,6,7,8-tetrahydro-1,6-naphthyridin-3-yl)-2-(tert-butoxy)acetic acid;

2-(6-([1,1'-Biphenyl]-4-yl)-4-(4-fluorophenyl)-2-isopropyl-8,8-dimethyl-5,6,7,8-tetrahydro-1,6-naphthyridin-3-yl)-2-(tert-butoxy)acetic acid;

2-(6-((Benzyloxy)carbonyl)-2-methyl-4-(p-tolyl)-5,6,7,8-tetrahydro-1,6-naphthyridin-3-yl)-2-(tert-butoxy)acetic acid;

2-(tert-Butoxy)-2-(2-methyl-4-(p-tolyl)-5,6,7,8-tetrahydro-1,6-naphthyridin-3-yl)acetic acid;

2-(6-Benzyl-2-methyl-4-(p-tolyl)-5,6,7,8-tetrahydro-1,6-naphthyridin-3-yl)-2-(tert-butoxy)acetic acid;

2-(tert-Butoxy)-2-(2-methyl-6-(methylsulfonyl)-4-(p-tolyl)-5,6,7,8-tetrahydro-1,6-naphthyridin-3-yl)acetic acid;

2-(tert-Butoxy)-2-(2,6-dimethyl-4-(p-tolyl)-5,6,7,8-tetrahydro-1,6-naphthyridin-3-yl)acetic acid;

2-(tert-Butoxy)-2-(2-methyl-6-phenethyl-4-(p-tolyl)-5,6,7,8-tetrahydro-1,6-naphthyridin-3-yl)acetic acid;

2-(6-Acetyl-2-methyl-4-(p-tolyl)-5,6,7,8-tetrahydro-1,6-naphthyridin-3-yl)-2-(tert-butoxy)acetic acid;

2-(tert-Butoxy)-2-(6-(methoxycarbonyl)-2-methyl-4-(p-tolyl)-5,6,7,8-tetrahydro-1,6-naphthyridin-3-yl)acetic acid;

2-(6-(Benzylcarbamoyl)-2-methyl-4-(p-tolyl)-5,6,7,8-tetrahydro-1,6-naphthyridin-3-yl)-2-(tert-butoxy)acetic acid;

2-(tert-Butoxy)-2-(2-methyl-6-(3-phenylpropanoyl)-4-(p-tolyl)-5,6,7,8-tetrahydro-1,6-naphthyridin-3-yl)acetic acid;

2-(tert-Butoxy)-2-(2-methyl-6-(3-phenylpropyl)-4-(p-tolyl)-5,6,7,8-tetrahydro-1,6-naphthyridin-3-yl)acetic acid;

2-(6-([1,1'-Biphenyl]-4-yl)-2-methyl-4-(p-tolyl)-5,6,7,8-tetrahydro-1,6-naphthyridin-3-yl)-2-(tert-butoxy)acetic acid;

2-(tert-Butoxy)-2-(2-methyl-6-phenyl-4-(p-tolyl)-5,6,7,8-tetrahydro-1,6-naphthyridin-3-yl)acetic acid; and 2-(tert-Butoxy)-2-(2-methyl-6-(2-(4-methylphenylsulfonamido)-3-phenylpropanoyl)-4-(p-tolyl)-5,6,7,8-tetrahydro-1,6-naphthyridin-3-yl)acetic acid;

or a pharmaceutically acceptable salt thereof.

13. A compound of claim 1 selected from the group consisting of (S)-2-(tert-Butoxy)-2-(6-(3-(4-methoxyphenyl)propyl)-2-methyl-4-(p-tolyl)-5,6,7,8-tetrahydro-1,6-naphthyridin-3-yl)acetic acid;

(S)-2-(tert-Butoxy)-2-(6-(3-(4-chlorophenyl)propyl)-2-methyl-4-(p-tolyl)-5,6,7,8-tetrahydro-1,6-naphthyridin-3-yl)acetic acid;

(2S)-2-(6-((Benzyloxy)carbonyl)-4-(8-fluoro-5-methylchroman-6-yl)-2,8,8-trimethyl-5,6,7,8-tetrahydro-1,6-naphthyridin-3-yl)-2-(tert-butoxy)acetic acid;

(2S)-2-(tert-Butoxy)-2-(6-(3-chlorobenzyl)-4-(8-fluoro-5-methylchroman-6-yl)-2,8,8-trimethyl-5,6,7,8-tetrahydro-1,6-naphthyridin-3-yl)acetic acid;

(S)-2-(6-((Benzyloxy)carbonyl)-4-(4-chlorophenyl)-2-methyl-5,6,7,8-tetrahydro-1,6-naphthyridin-3-yl)-2-(tert-butoxy)acetic acid;

(S)-2-(tert-Butoxy)-2-(6-(3-chlorobenzyl)-2-methyl-4-(p-tolyl)-5,6,7,8-tetrahydro-1,6-naphthyridin-3-yl)acetic acid;

(2S)-2-(test-Butoxy)-2-(4-(8-fluoro-5-methylchroman-6-yl)-2,8,8-trimethyl-6-(3-phenylpropyl)-5,6,7,8-tetrahydro-1,6-naphthyridin-3-yl)acetic acid;

(S)-2-(tert-Butoxy)-2-(6-(4-chlorobenzyl)-2-methyl-4-(p-tolyl)-5,6,7,8-tetrahydro-1,6-naphthyridin-3-yl)acetic acid;

(2S)-2-(tert-Butoxy)-2-((R)-4-(8-fluoro-5-methylchroman-6-yl)-2-methyl-6-(3-phenylpropyl)-5,6,7,8-tetrahydro-1,6-naphthyridin-3-yl)acetic acid;

(S)-2-(tert-Butoxy)-2-(2,8,8-trimethyl-6-(3-phenylpropyl)-4-(p-tolyl)-5,6,7,8-tetrahydro-1,6-naphthyridin-3-yl)acetic acid;

(2S)-2-(tert-Butoxy)-2-(6-(3-(4-chlorophenyl)propyl)-(R)-4-(8-fluoro-5-methylchroman-6-yl)-2-methyl-5,6,7,8-tetrahydro-1,6-naphthyridin-3-yl)acetic acid;

(S)-2-(tert-Butoxy)-2-((R)-4-(8-fluoro-5-methylchroman-6-yl)-6-(3-(4-fluorophenyl)propyl)-2-methyl-5,6,7,8-tetrahydro-1,6-naphthyridin-3-yl)acetic acid;

(S)-2-(6-(2-(1H-Indol-3-yl) ethyl)-2-methyl-4-(p-tolyl)-5,6,7,8-tetrahydro-1,6-naphthyridin-3-yl)-2-(tert-butoxy)acetic acid;

(2S)-2-(tert-Butoxy)-2-((R)-4-(8-fluoro-5-methylchroman-6-yl)-2-methyl-6-(3-(m-tolyl)propyl)-5,6,7,8-tetrahydro-1,6-naphthyridin-3-yl)acetic acid;

(2S)-2-(tert-Butoxy)-2-((R)-4-(8-fluoro-5-methylchroman-6-yl)-2-methyl-6-(3-(o-tolyl)propyl)-5,6,7,8-tetrahydro-1,6-naphthyridin-3-yl)acetic acid;

(S)-2-(tert-Butoxy)-2-((R)-4-(8-fluoro-5-methylchroman-6-yl)-6-(3-(3-fluorophenyl)propyl)-2-methyl-5,6,7,8-tetrahydro-1,6-naphthyridin-3-yl)acetic acid;

(2S)-2-(tert-Butoxy)-2-((R)-4-(8-fluoro-5-methylchroman-6-yl)-2-methyl-6-((2-phenylcyclopropyl)methyl)-5,6,7,8-tetrahydro-1,6-naphthyridin-3-yl)acetic acid;

(2S)-2-(tert-Butoxy)-2-(6-(3-(3-fluoro-4-methylphenyl)propyl)-(R)-4-(8-fluoro-5-methyl-3,4,4a,5-tetrahydro-2H-chromen-6-yl)-2-methyl-5,6,7,8-tetrahydro-1,6-naphthyridin-3-yl)acetic acid;

(2S)-2-(tert-Butoxy)-2-(6-(3-(4-fluoro-3-methylphenyl)propyl)-(R)-4-(8-fluoro-5-methylchroman-6-yl)-2-methyl-5,6,7,8-tetrahydro-1,6-naphthyridin-3-yl)acetic acid;

(2S)-2-(tert-Butoxy)-2-((R)-4-(8-fluoro-5-methyl-3,4,4a,5-tetrahydro-2H-chromen-6-yl)-2-methyl-6-(3-(3-(trifluoromethyl)phenyl)propyl)-5,6,7,8-tetrahydro-1,6-naphthyridin-3-yl)acetic acid;

(2S)-2-(tert-Butoxy)-2-(4-(8-fluoro-5-methylchroman-6-yl)-2-methyl-6-(3-(p-tolyl)propyl)-5,6,7,8-tetrahydro-1,6-naphthyridin-3-yl)acetic acid; and (2S)-2-(tert-Butoxy)-2-((R)-4-(8-fluoro-5-methylchroman-6-yl)-6-(3-(2-fluorophenyl)propyl)-2-methyl-5,6,7,8-tetrahydro-1,6-naphthyridin-3-yl)acetic acid or a pharmaceutically acceptable salt thereof.

14. A composition useful for treating HIV infection comprising a therapeutic amount of a compound of claim 1 and a pharmaceutically acceptable carrier.

15. A method for treating HIV infection comprising administering a therapeutically effective amount of a compound of claim 1, or a pharmaceutically acceptable salt thereof, to a patient in need thereof.

* * * * *

UNITED STATES PATENT AND TRADEMARK OFFICE
CERTIFICATE OF CORRECTION

PATENT NO.         : 8,629,276 B2
APPLICATION NO.    : 13/766587
DATED              : January 14, 2014
INVENTOR(S)        : Michael A. Walker et al.

It is certified that error appears in the above-identified patent and that said Letters Patent is hereby corrected as shown below:

In the Claims:

Claim 3:

Column 63, line 31, change "$((Ar^2)$alkoxyCO," to -- $(Ar^2)$alkoxyCO, --.

Claim 4:

Column 63, line 62, change "$((Ar^2)$alkoxyCO," to -- $(Ar^2)$alkoxyCO, --.

Claim 5:

Column 64, line 3, change "$((Ar^2)$alkoxyCO," to -- $(Ar^2)$alkoxyCO, --.

Claim 12:

Column 64, lines 31 and 32, change "-((4-fluorophenyl)" to -- -(4-fluorophenyl) --.

Column 64, line 37, change "-O-(4-fluorophenyl)" to -- -(4-(4-fluorophenyl) --.

Column 64, line 44, change "-((4-methylphenylsolfonamido)-" to -- -(4-methylphenylsulfonamido)- --.

Claim 13:

Column 66, line 1, change "-(test-Butoxy)-" to -- -(tert-Butoxy)- --.

Signed and Sealed this
Seventh Day of April, 2015

Michelle K. Lee
*Director of the United States Patent and Trademark Office*